US012558191B2

(12) United States Patent
Hongo et al.

(10) Patent No.:  US 12,558,191 B2
(45) Date of Patent:      Feb. 24, 2026

(54) MEDICAL ARM DEVICE

(71) Applicant: Sony Group Corporation, Tokyo (JP)

(72) Inventors: Kazuo Hongo, Tokyo (JP); Jun Arai, Tokyo (JP)

(73) Assignee: SONY GROUP COPRORATION, Tokyo (JP)

( * ) Notice: Subject to any disclaimer, the term of this patent is extended or adjusted under 35 U.S.C. 154(b) by 565 days.

(21) Appl. No.: 17/999,707

(22) PCT Filed: Jun. 30, 2021

(86) PCT No.: PCT/JP2021/024852
§ 371 (c)(1),
(2) Date: Nov. 23, 2022

(87) PCT Pub. No.: WO2022/009756
PCT Pub. Date: Jan. 13, 2022

(65) Prior Publication Data
US 2023/0210630 A1      Jul. 6, 2023

(30) Foreign Application Priority Data

Jul. 9, 2020     (JP) ................................. 2020-118525

(51) Int. Cl.
A61B 90/50          (2016.01)
A61B 34/00          (2016.01)

(52) U.S. Cl.
CPC .............. A61B 90/50 (2016.02); A61B 34/71 (2016.02)

(58) Field of Classification Search
CPC ... A61B 90/50; A61B 90/10–11; A61B 34/71; A61B 34/70; A61B 34/37;
(Continued)

(56) References Cited

U.S. PATENT DOCUMENTS 6,394,998 B1 *    5/2002   Wallace ................. A61B 34/35
                                                                  901/29
6,902,560 B1 *    6/2005   Morley .................. A61B 34/30
                                                                  606/1
(Continued)

FOREIGN PATENT DOCUMENTS

JP           2006-305717 A       11/2006
JP           2008-114339 A        5/2008
(Continued)

OTHER PUBLICATIONS

International Search Report and Written Opinion mailed on Aug. 24, 2021, received for PCT Application PCT/JP2021/024852, filed on Jun. 30, 2021, 8 pages including English Translation.

*Primary Examiner* — Brigid K Byrd
(74) *Attorney, Agent, or Firm* — XSENSUS LLP

(57)                ABSTRACT

A medical arm device to support a medical instrument has a tip part with a structure in which three rotation axes are disposed in order of a rotation axis around a longitudinal axis of the medical instrument, a yaw axis that rotates the medical instrument left and right with respect to a tip of a link, and a pitch axis that rotates the medical instrument up and down with respect to the tip of the link, and a first wire for rotation transmission of the yaw axis, a second wire for rotation transmission of the roll axis, a first rerouting pulley that reroutes the first wire between the pitch axis and the yaw axis, a second rerouting pulley that reroutes the second wire between the pitch axis and the yaw axis, and a third rerouting pulley that reroutes the second wire between the yaw axis and the roll axis.

20 Claims, 32 Drawing Sheets

(58) Field of Classification Search
CPC .. A61B 34/30; A61B 2034/305; B25J 18/007;
B25J 17/02–0291
See application file for complete search history.

(56)                     References Cited

U.S. PATENT DOCUMENTS

| | | | | |
|---|---|---|---|---|
| 2007/0089557 A1* | 4/2007 | Solomon | ............... | A61B 34/71 |
| | | | | 74/490.01 |
| 2007/0288044 A1* | 12/2007 | Jinno | .................... | A61B 17/29 |
| | | | | 606/174 |
| 2008/0046122 A1* | 2/2008 | Manzo | .................. | A61B 90/98 |
| | | | | 700/245 |
| 2009/0112229 A1* | 4/2009 | Omori | ................... | A61B 34/70 |
| | | | | 606/205 |
| 2009/0163929 A1 | 6/2009 | Yeung | | |
| 2011/0213384 A1 | 9/2011 | Jeong | | |
| 2015/0150635 A1 | 6/2015 | Kilroy | | |
| 2019/0168389 A1* | 6/2019 | Shino | ................... | B25J 13/088 |

FOREIGN PATENT DOCUMENTS

| | | | |
|---|---|---|---|
| JP | 2016-518160 A | 6/2016 | |
| JP | 2018-075121 A | 5/2018 | |
| WO | 2016/152255 A1 | 9/2016 | |
| WO | WO-2021049286 A1 | 3/2021 | |

* cited by examiner

MOTOR 2200

MOTOR BODY 2201

ROTATION AXIS

BRAKE
2202

SPEED REDUCER
2203

ENCODER
2204

TORQUE SENSOR
2205

CIRCUIT UNIT
2206

FOURTH LINK 104

TIP PART SIDE                                                              ROOT SIDE

FIRST MOTOR
2301
(FOR ROLL AXIS ROTATION)

SECOND MOTOR
2302
(FOR YAW AXIS ROTATION)

THIRD MOTOR
2303
(FOR PITCH AXIS ROTATION)

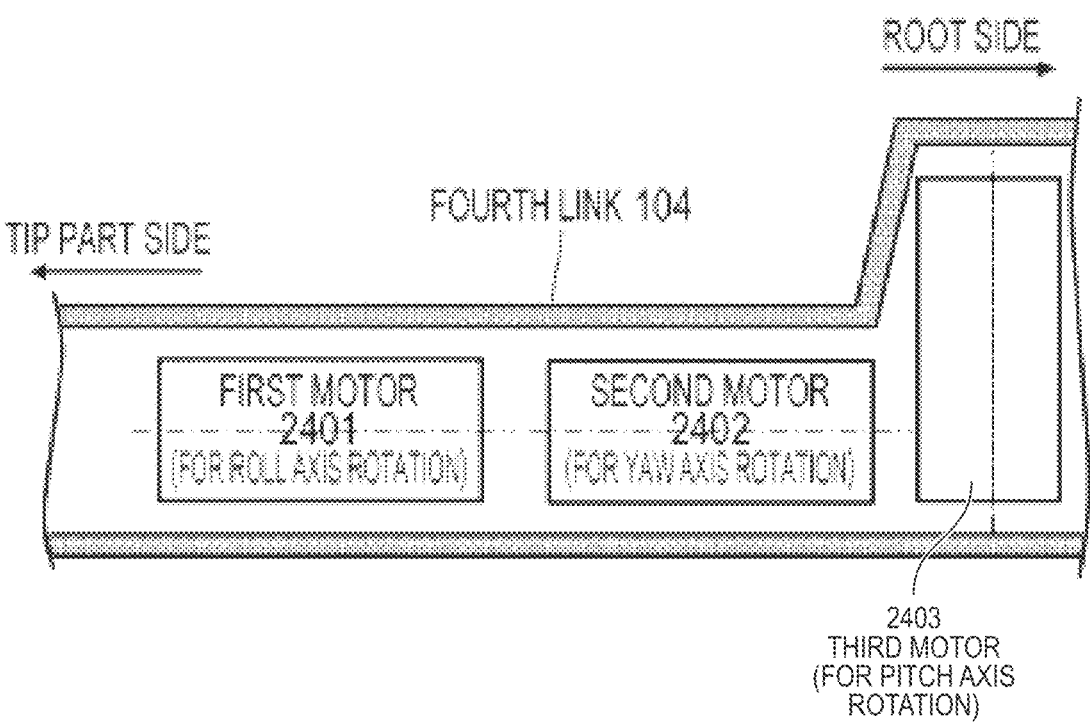
FIG. 24
FIG. 25
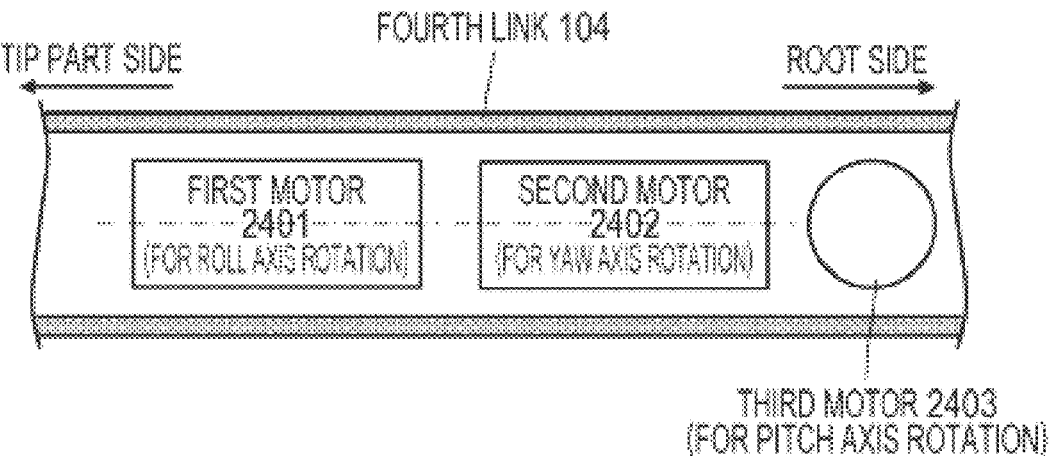

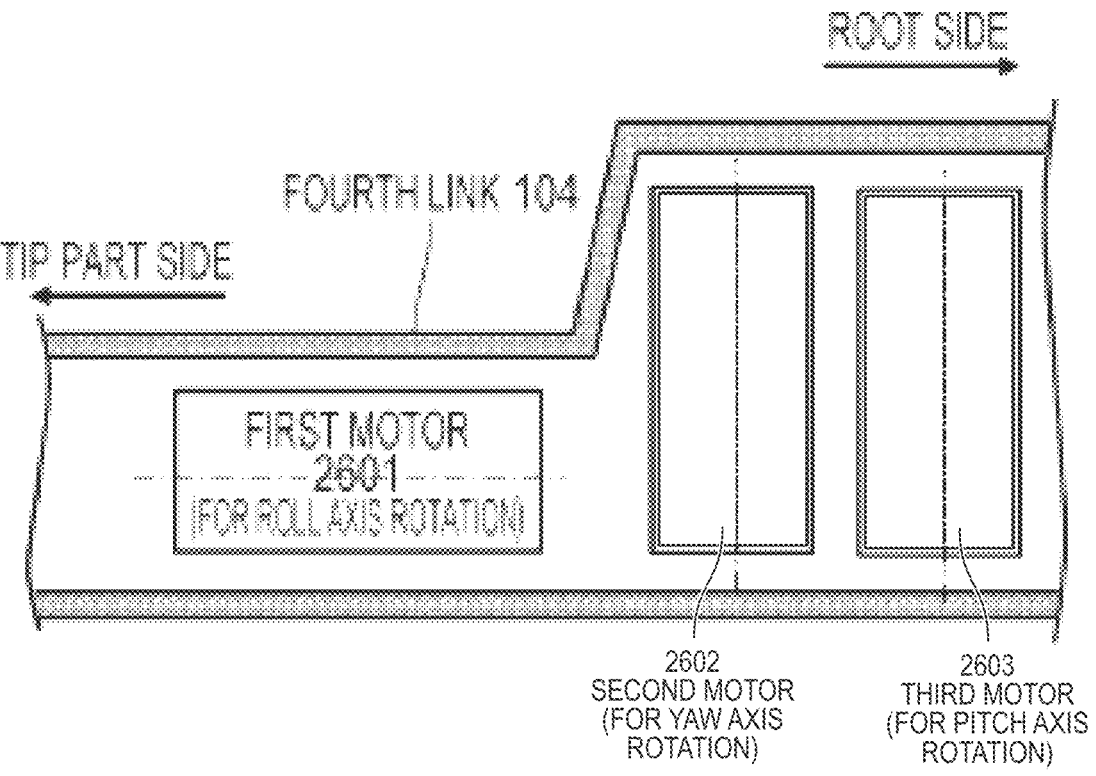
FIG. 26
*FIG. 27*
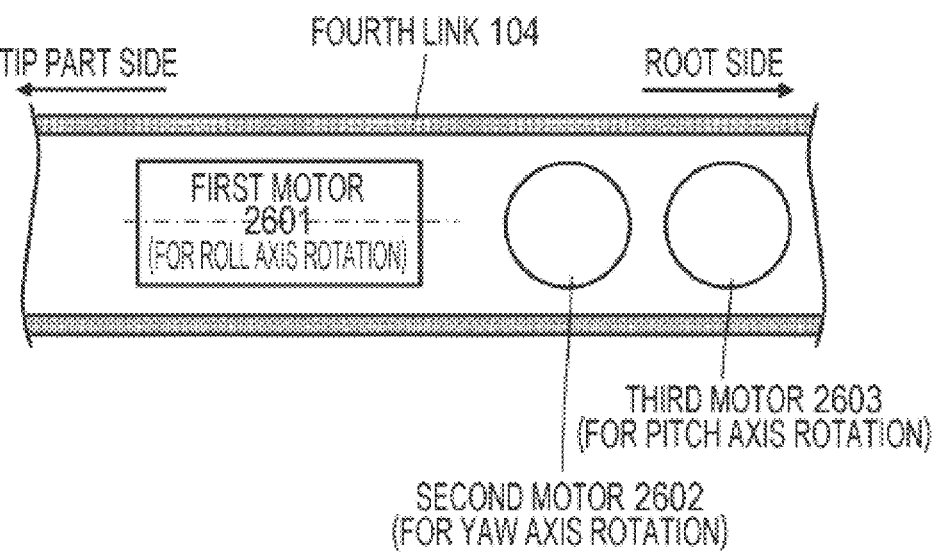

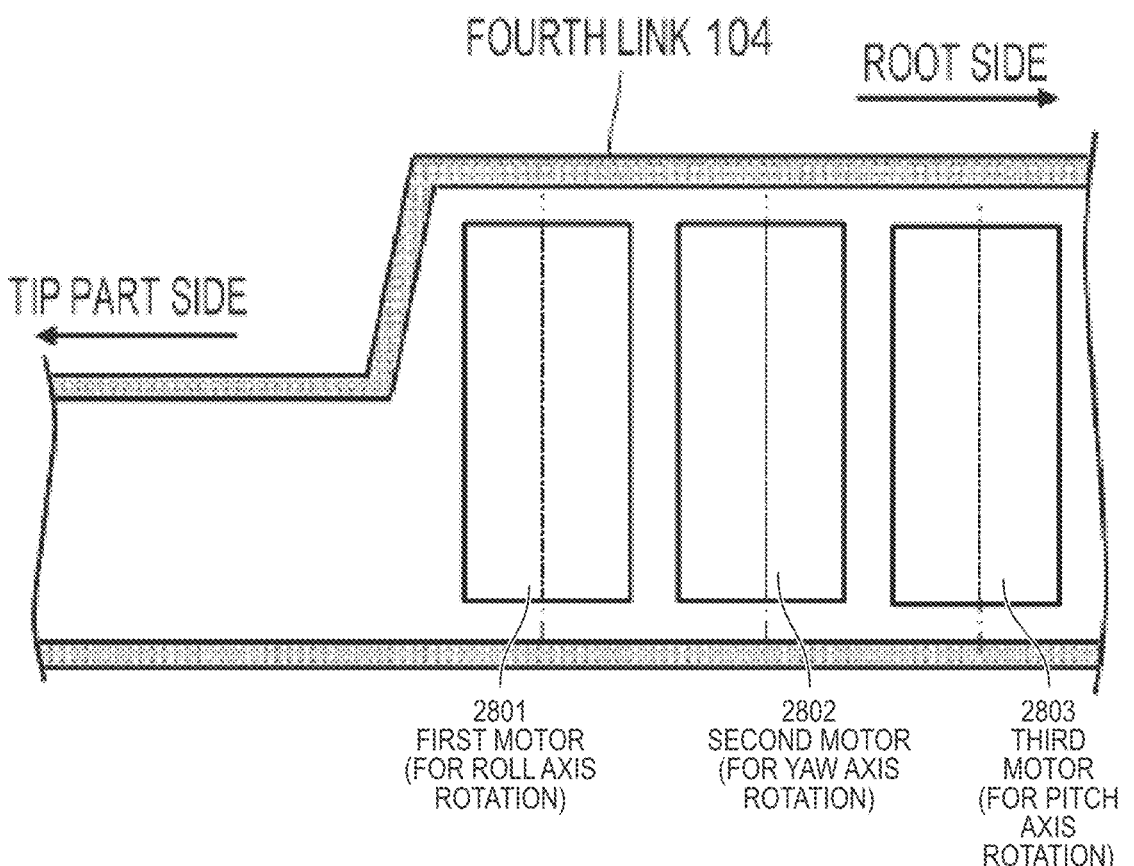
FOURTH LINK 104
ROOT SIDE
TIP PART SIDE
2801
FIRST MOTOR
(FOR ROLL AXIS
ROTATION)
2802
SECOND MOTOR
(FOR YAW AXIS
ROTATION)
2803
THIRD
MOTOR
(FOR PITCH
AXIS
ROTATION)
FIG. 28
*FIG. 29*
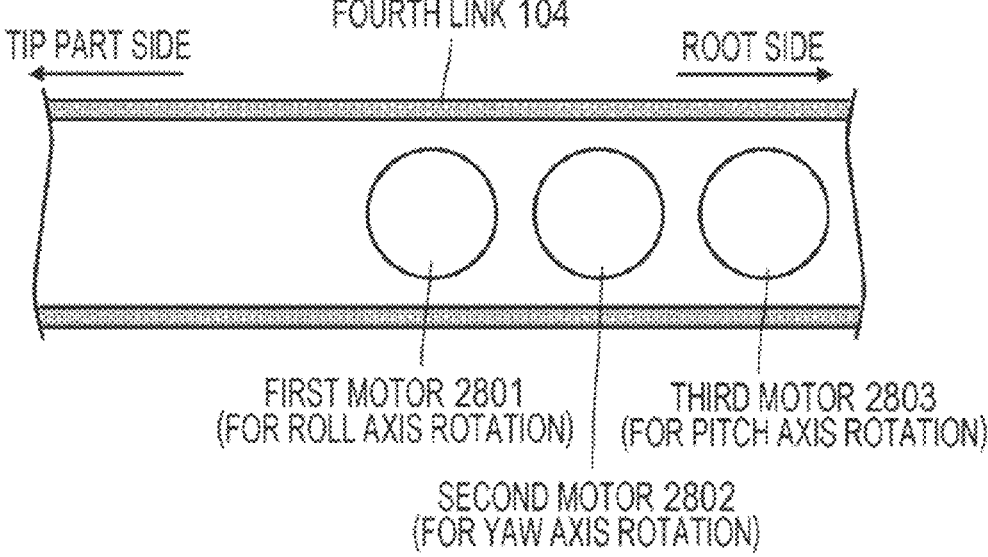
FOURTH LINK 104
TIP PART SIDE
ROOT SIDE
FIRST MOTOR 2801
(FOR ROLL AXIS ROTATION)
THIRD MOTOR 2803
(FOR PITCH AXIS ROTATION)
SECOND MOTOR 2802
(FOR YAW AXIS ROTATION)

FIG. 32

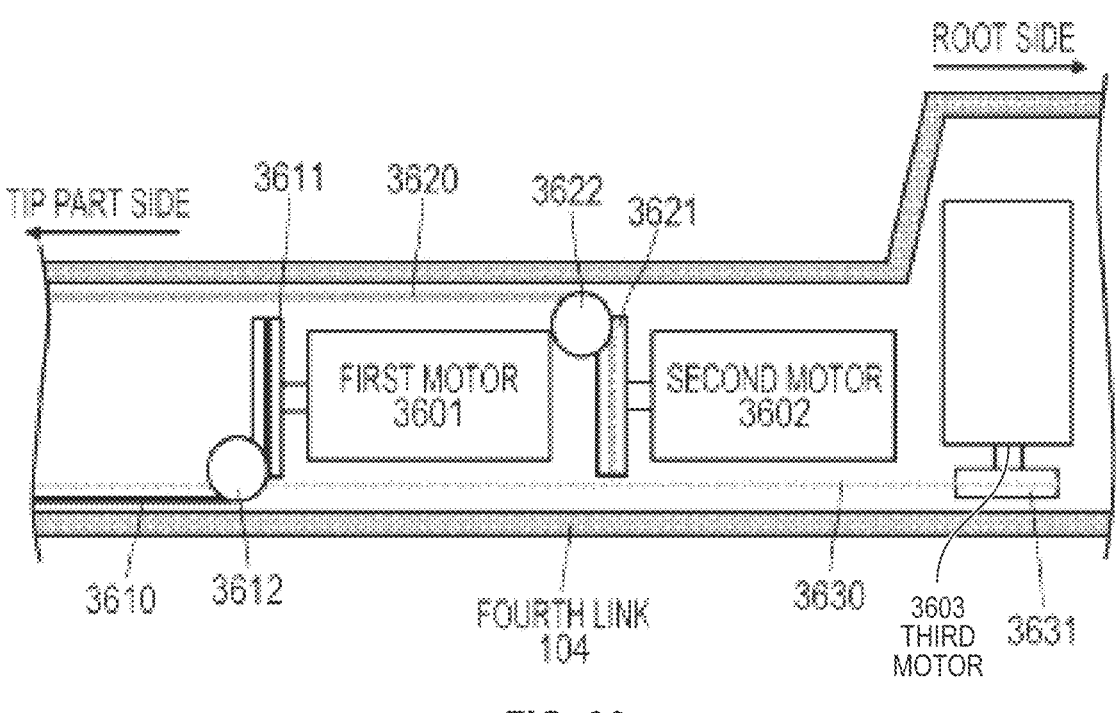
FIG. 36
*FIG. 37*
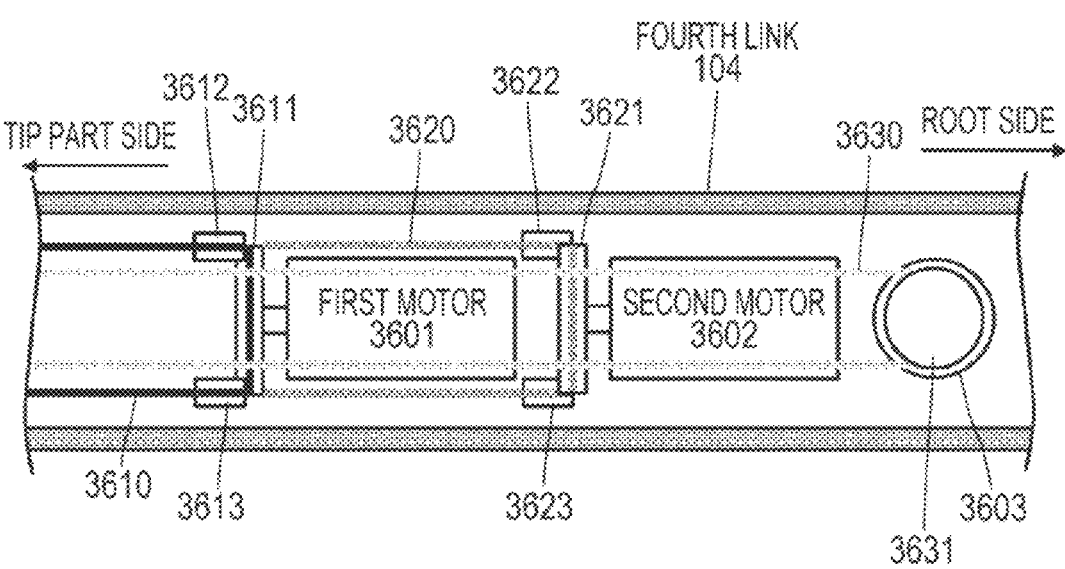

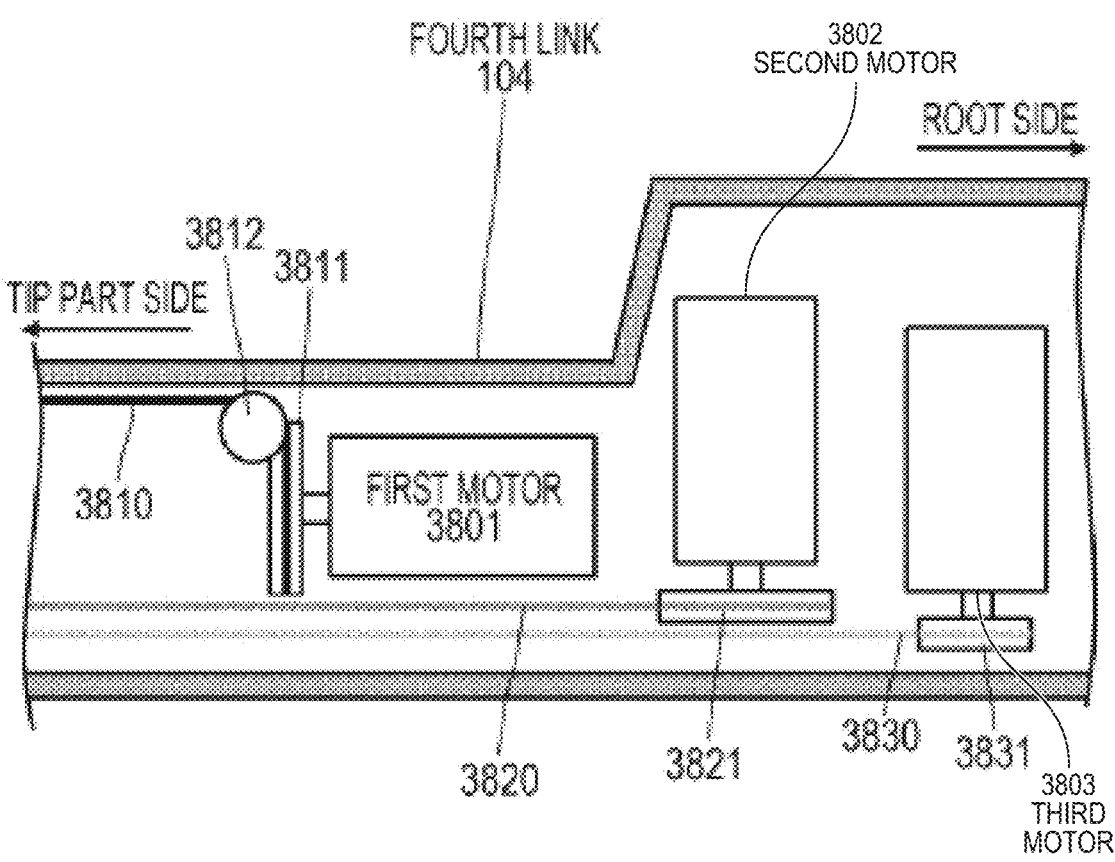
FIG. 38
FIG. 39
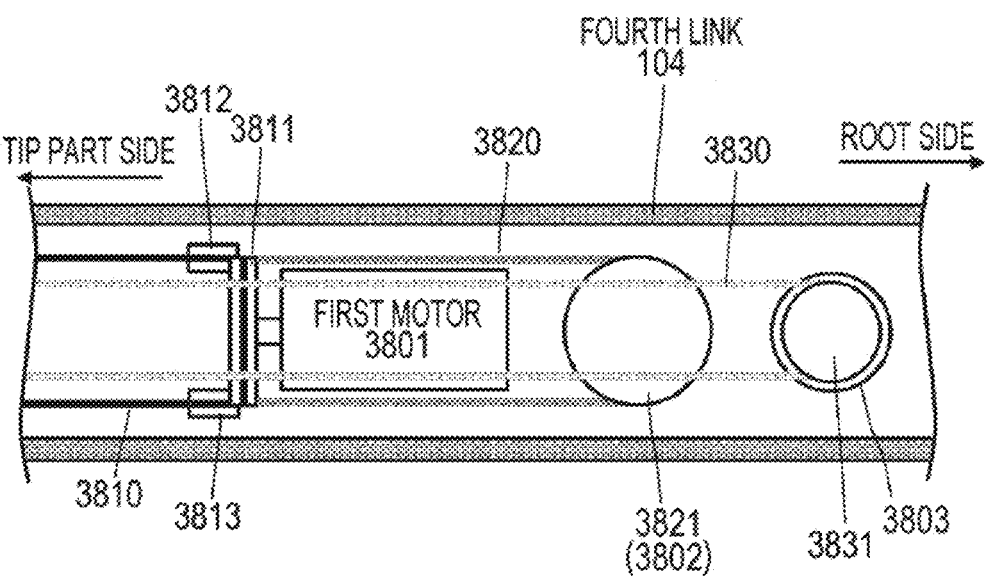

MEDICAL ARM DEVICE

CROSS-REFERENCE TO RELATED APPLICATIONS

The present application is based on PCT filing PCT/JP2021/024852, filed Jun. 30, 2021, which claims priority to Japanese Application No. 2020-118525, filed Jul. 9, 2020, the entire contents of each are incorporated herein by reference.

TECHNICAL FIELD

The technology disclosed in the present specification (hereinafter, "the present disclosure") relates to a medical arm device used, for example, for supporting a medical instrument.

BACKGROUND ART

Laparoscopic surgery is widely performed because it does not require laparotomy, imposes a small burden on a patient, and provides quick recovery after the surgery. In the laparoscopic surgery, visual field adjustment of an endoscope affects the progress of the surgery, but a control technique is not constant for each operator (surgeon, scopist). Therefore, by introducing a medical arm device (See, for example, Patent Document 1.) that supports an endoscope, cost reduction such as labor cost of an operator, high accuracy of a control technique of the endoscope, and improvement of safety are achieved.

In the laparoscopic surgery, it is necessary to image the vicinity of a medical instrument such as forceps operated by a surgeon with an endoscope, and parts holding the endoscope and the medical instrument respectively move in the vicinity. If a tip part of the medical arm device that supports the endoscope is large, an operation of the medical instrument by the surgeon is hindered. On the other hand, in order to image a periphery of an affected area at a wide angle, it is necessary to operate the endoscope as wide as possible. Therefore, it is preferable to condense a multi-degree-of-freedom active joint having such a high torque that the endoscope can be held while a tip of the medical arm device is as thin and compact as possible.

Conventionally, a manipulator having a structure in which a small-diameter tip part is driven using a wire or a gear has been proposed (See, for example, Patent Documents 2 and 3.). If the gear is used, an infinite rotation structure is easily realized, but backlash is easily generated in a transmission part. In a case where a long structure such as an endoscope is supported, if there is backlash, the structure greatly swings, so that a drive mechanism using a gear is not appropriate.

CITATION LIST

Patent Document

Patent Document 1: Japanese Patent Application Laid-Open No. 2018-75121
Patent Document 2: Japanese Patent Application Laid-Open No. 2006-305717
Patent Document 3: Japanese Patent Application Laid-Open No. 2008-114339

SUMMARY OF THE INVENTION

Problems to be Solved by the Invention

An object of the present disclosure is to provide a medical arm device that is compact and includes a tip part in which a multi-degree-of-freedom active joint is condensed with a high torque so as to be able to hold a medical instrument such as an endoscope.

Solutions to Problems

The present disclosure has been made in view of the problems described above, and is a medical arm device including:

a first arm part including a tip part that holds a medical instrument and a link that supports the tip part; and
a second arm part that supports the first arm part,
in which the tip part includes
a structure in which three rotation axes are disposed in order of a rotation axis around a longitudinal axis of the medical instrument, a yaw axis that rotates the medical instrument left and right with respect to a tip of the link, and a pitch axis that rotates the medical instrument up and down with respect to the tip of the link in order from a most tip part, and
a first wire for rotation transmission of the yaw axis, a second wire for rotation transmission of the roll axis, a first rerouting pulley that reroutes the first wire between the pitch axis and the yaw axis, a second rerouting pulley that reroutes the second wire between the pitch axis and the yaw axis, and a third rerouting pulley that reroutes the second wire between the yaw axis and the roll axis are disposed on the link.

At least one of the first rerouting pulley or the second rerouting pulley includes a set of rerouting pulleys having different diameters disposed on an identical axis on an opposite side of a structure body rotating around the pitch axis.

In the medical arm device according to the present disclosure, a shaft constituting an identical axis of the first rerouting pulley or the second rerouting pulley includes an interference avoidance part with a yaw axis pulley around which the first wire is wound to rotate around the yaw axis. The interference avoidance part includes a small diameter part or a D-cut structure part in a central part of the shaft.

Furthermore, the medical arm device according to the present disclosure includes an interference avoidance structure that avoids interference between the second rerouting pulley and the third rerouting pulley during rotation around the yaw axis. The interference avoidance structure includes a set of rerouting pulleys constituting the second rerouting pulley and disposed such that rotation axes of the rerouting pulleys cross each other, and a structure in which a plurality of pulleys constituting the third rerouting pulley is disposed in a predetermined region in a concentrated manner.

Effects of the Invention

According to the present disclosure, it is possible to provide a medical arm device that is small and light, and includes a tip part having a structure in which orthogonal rotation axes of three degrees of freedom that determine an attitude of an endoscope are disposed in a concentrated manner.

Note that the effects described in the present specification are merely examples, and the effects brought by the present disclosure are not limited thereto. Furthermore, the present disclosure may further provide additional effects in addition to the effects described above.

Still other objects, features, and advantages of the present disclosure will become apparent from a more detailed description based on embodiments as described later and the accompanying drawings.

BRIEF DESCRIPTION OF DRAWINGS

FIG. 24 is a diagram illustrating an arrangement example (2) of each motor that drives each rotation mechanism of the arm tip part.

FIG. 25 is a diagram illustrating an arrangement example (2) of each motor that drives each rotation mechanism of the arm tip part.

FIG. 26 is a diagram illustrating an arrangement example (3) of each motor that drives each rotation mechanism of the arm tip part.

FIG. 27 is a diagram illustrating an arrangement example (3) of each motor that drives each rotation mechanism of the arm tip part.

FIG. 28 is a diagram illustrating an arrangement example (4) of each motor that drives each rotation mechanism of the arm tip part.

FIG. 29 is a diagram illustrating an arrangement example (4) of each motor that drives each rotation mechanism of the arm tip part.

FIG. 32 is a diagram illustrating an arrangement example (6) of each motor that drives each rotation mechanism of the arm tip part.

FIG. 36 is a diagram illustrating a configuration example of a wire transmission mechanism corresponding to the arrangement example (2) of the motor.

FIG. 37 is a diagram illustrating a configuration example of the wire transmission mechanism corresponding to the arrangement example (2) of the motor.

FIG. 38 is a diagram illustrating a configuration example of a wire transmission mechanism corresponding to the arrangement example (3) of the motor.

FIG. 39 is a diagram illustrating a configuration example of the wire transmission mechanism corresponding to the arrangement example (3) of the motor.

MODE FOR CARRYING OUT THE INVENTION

Hereinafter, the technology according to the present disclosure will be described in the following order with reference to the drawings.

A. Overview

B. Configuration of medical arm device

C. Endoscope holding structure

D. Regarding control of tip part

E. Another structure (1) of tip part

F. Another structure (2) of tip part

G. Regarding increase in torque

H. Regarding load reduction of actuator by weight reduction of tip part

I. Arrangement of actuators

J. Regarding two-groove pulley accommodating pitch axis rotation

K. Regarding two-groove pulley coaxial with pitch axis

L. Regarding pulley for driving roll axis

M. Regarding maximization of yaw axis driving pulley

N. Effects

O. Regarding actuator arrangement

A. Overview

The present disclosure is a medical arm device capable of supporting an endoscope at a tip part having an active joint with three degrees of freedom, and determining an attitude of the endoscope by wire-driving each active joint. The present disclosure realizes a medical arm device that satisfies each of the following requirements, suppresses an increase in size of the device, and realizes a higher degree of freedom of an arm and a wider movable range.

(1) The tip part has a high torque enough to hold the endoscope.

(2) By making the tip part small and lightweight, interference between other medical instruments in an abdominal cavity such as forceps and the tip part and collision between the arm and the surgeon's hand or arm are avoided.

(3) By making the tip part small and lightweight, a load of the motor that drives the active joint of the tip part is reduced, and a total weight, cost, and power consumption of the device are reduced.

(4) Drive active joints of three degrees of freedom of the tip part without backlash.

B. Configuration of Medical Arm Device

Figure 1:
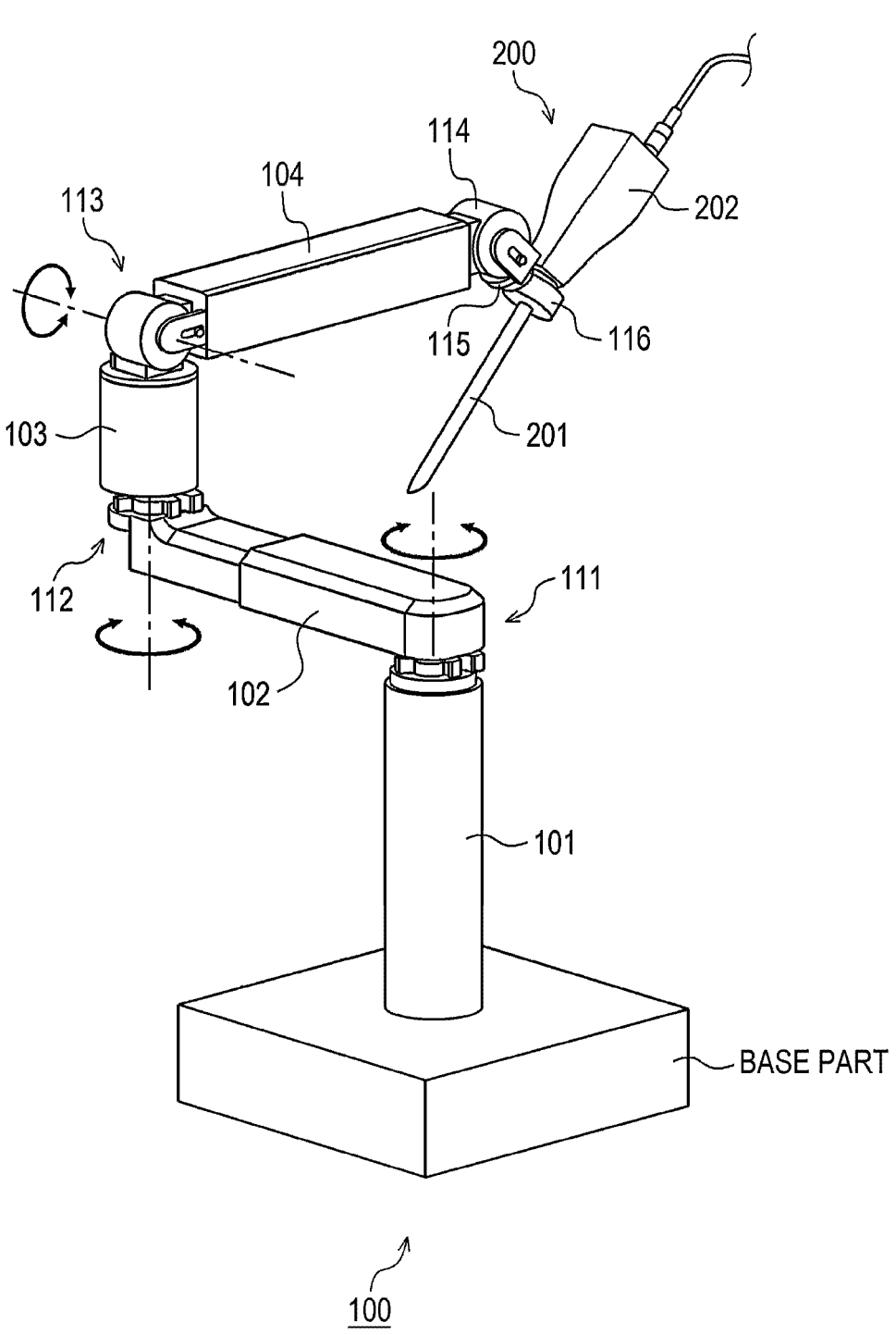
FIG. 1 is a diagram illustrating an appearance configuration example of a medical arm device 100.

FIG. 1 illustrates an appearance configuration example of a medical arm device 100 applied to laparoscopic surgery. The illustrated medical arm device 100 has a structure in which an arm having a multi-link structure supports an endoscope at a tip part, and orthogonal rotation axes of three degrees of freedom for determining an attitude of the endoscope are intensively disposed.

Specifically, the medical arm device 100 includes: a first link 101 attached substantially vertically to a base part; a first joint part 111 having a degree of freedom around a horizontal rotation axis (alternatively, a longitudinal axis of the first link 101) at a tip of the first link 101; a second link 102 attached horizontally to a tip of the first link 101 via the first joint part 111; a second joint part 112 having a degree of freedom around a horizontal rotation axis (or an axis orthogonal to the longitudinal axis of the second link 102) at a tip of the second link 102; a third link 103 attached substantially vertically to a tip of the second link 102 via the second joint part 112; a third joint part 113 having a degree of freedom around a vertical rotation axis (or an axis orthogonal to a longitudinal axis of the third link 103) orthogonal to the horizontal rotation axis at a tip of the third link 103, a fourth link 104 attached to the tip of the third link 103 via the third joint part 113, and a tip part supporting an endoscope at a tip of the fourth link 104. Note that the base part may be attached to, for example, a frame of an operating bed, may be installed on a floor surface of an operating room, or may be installed on a ceiling.

The tip part supporting an endoscope 110 at a distal end of the fourth link 104 has a structure in which orthogonal rotation axes of three degrees of freedom for determining the attitude of the endoscope 110 are intensively arranged. The structure in which the orthogonal rotation axes of three degrees of freedom of the tip part are intensively disposed corresponds to, for example, a structure in which three orthogonal rotation axes are connected without interposing a link, or a structure in which each of joint members corresponding to the three rotation axes is directly connected, and more specifically, a member connecting the three joint parts is not a link that gains an arm length but only a component that connects the joint parts. Note that the tip part that supports the endoscope 200 and the fourth link 104 having the tip part are referred to as a first arm part. Furthermore, a link part (the first link 101 and the second link) including two horizontal rotation axes (the first joint part 111 and the second joint part 112) is defined as a second arm part. In the medical arm device 100 illustrated in FIG. 1, the second arm part is connected by the third joint part 113 having a degree of freedom around the vertical rotation axis.

Figure 2:
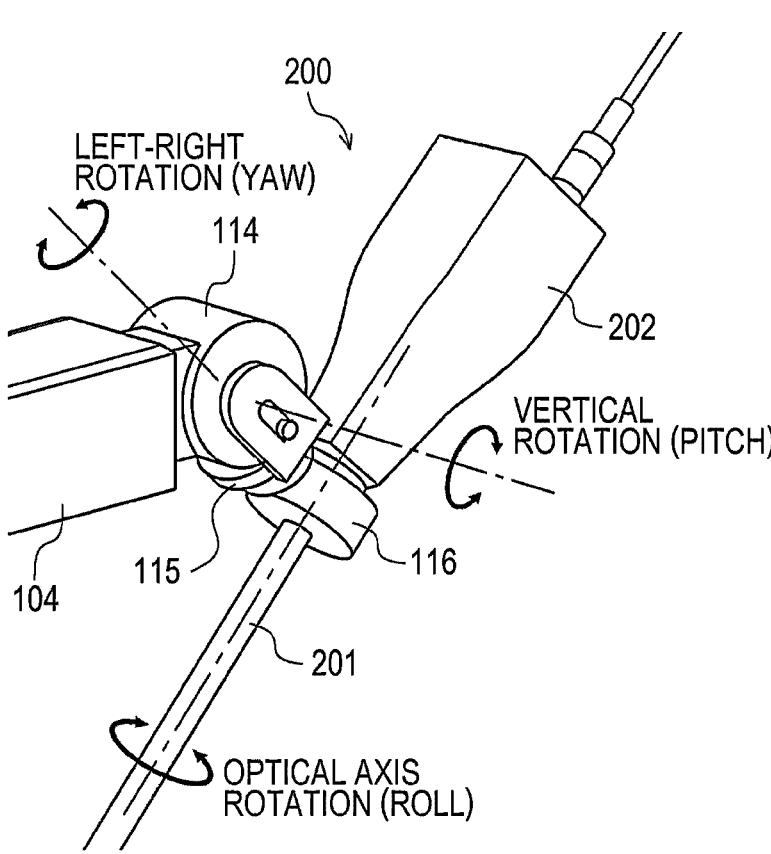
FIG. 2 is an enlarged diagram illustrating a structure of a tip part of the medical arm device 100 that supports an endoscope 200.

FIG. 2 illustrates an enlarged structure of the tip part of the medical arm device 100 that supports the endoscope 200. The endoscope 200 includes a lens barrel 201 inserted into a body cavity of a patient at a tip, and a camera head 202 connected to a proximal end of the lens barrel 201. The lens barrel 201 may be either a rigid mirror including a rigid lens barrel or a flexible mirror including a flexible lens barrel. An optical system and an imaging element (both not illustrated) are disposed in the camera head 202. Reflected light (observation light) from an observation target such as a surgical site is imaged on the imaging element by the optical system. Of course, the tip part of the medical arm device 100 may support a medical instrument other than the endoscope 200.

As illustrated in FIG. 2, the tip part of the medical arm device 100 includes a vertical rotation axis part 114 having a degree of freedom around a vertical rotation axis (or an axis orthogonal to a longitudinal axis of the fourth link 104) of the tip of the fourth link 104 and swinging the endoscope 200 in a vertical direction, a left-right rotation axis part 115 that is adjacent to the vertical rotation axis part 114, has a degree of freedom around a left-right rotation axis orthogonal to the vertical rotation axis, and swings the endoscope 200 in a left-right direction, and an optical axis rotation axis part 116 having a degree of freedom around an optical axis of the endoscope 200 (or the lens barrel 201 of the endoscope 200). Therefore, the orthogonal rotation axes of three degrees of freedom that determine the attitude of the endoscope 200 have a structure in which the optical axis rotation axis of the endoscope 200, the left-right rotation axis, and the vertical rotation axis are disposed in this order from the most tip part.

Note that the left-right rotation axis part 115 can be referred to as a pan axis that changes an observation direction of the endoscope 200, and the vertical rotation axis part 114 can be referred to as a tilt axis. Alternatively, in a case where the optical axis rotation axis part 116 is a roll axis, the left-right rotation axis part 115 can be referred to as a yaw axis, and the vertical rotation axis part 114 can be referred to as a pitch axis. If a combined volume of the joint parts corresponding to these three axes is smaller than a combined volume of human wrist and hand, there is an advantage of using the medical arm device 100 instead of the scopist. The optical axis rotation axis part 116 desirably minimizes a length to grip the endoscope 200 in an axial direction so as not to reduce an effective length of the endoscope 200. Furthermore, a distance between the vertical rotation axis part 114 and the optical axis rotation axis part 116 is desirably set to a length that avoids self-interference of the arm.

The structure in which the rotation axes orthogonal to each other with three degrees of freedom are intensively disposed as illustrated in FIG. 2 is a structure in which the joint members corresponding to the rotation axes with three degrees of freedom are directly connected or a structure in which a distance between the joint corresponding to the rotation axis around the longitudinal axis and the joint corresponding to the pitch axis has a distance that does not cause interference when rotating around the pitch axis. Therefore, it is possible to reduce a space affected by the movement of the tip part, and it is possible to suppress interference with a work space of the surgeon. Incidentally, in a case where the vertical rotation axis part 114 is disposed closer to a root side, it is assumed that the movement on a surgeon's hand side becomes large when the vertical rotation axis part 114 is operated.

Figure 3:
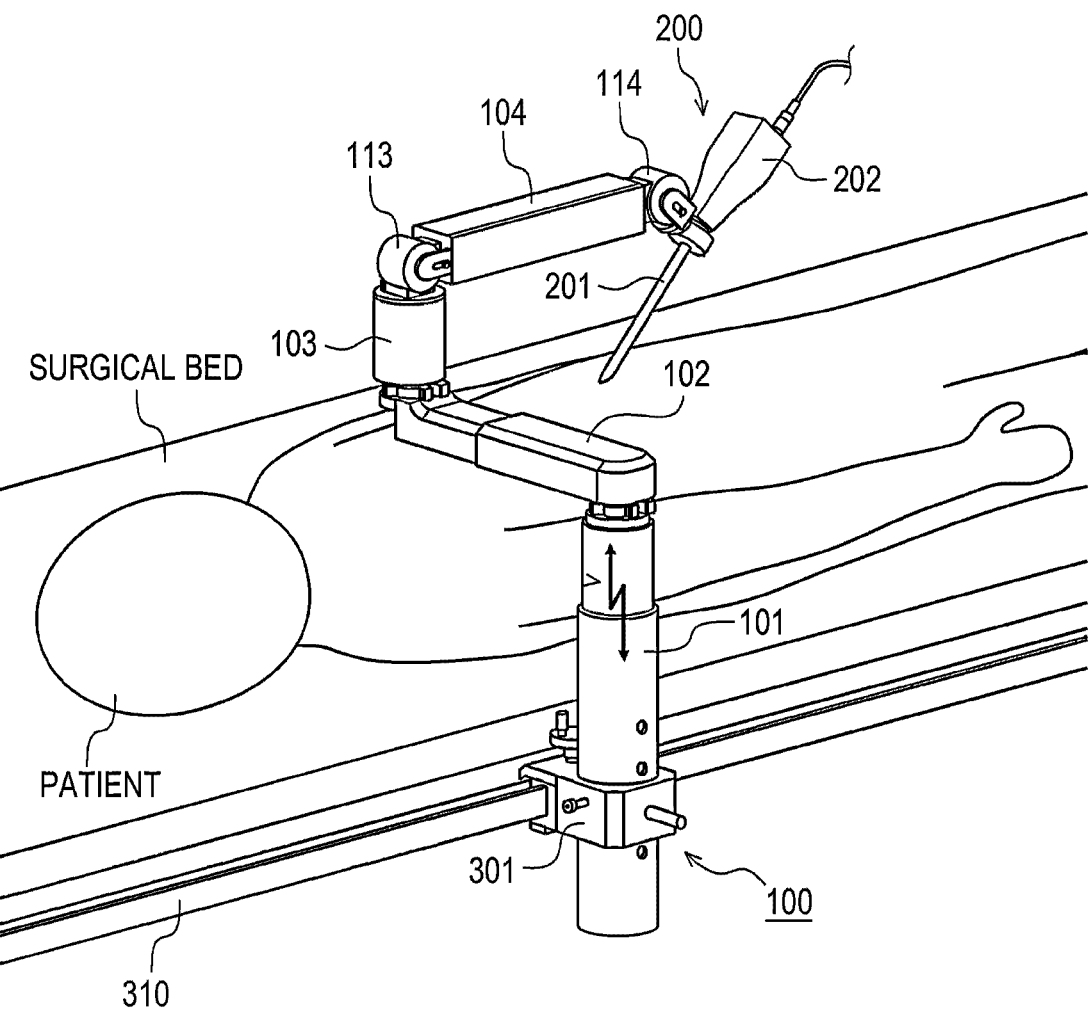
FIG. 3 is a diagram illustrating an example in which the medical arm device 100 is used for laparoscopic surgery.

FIG. 3 illustrates an example in which the medical arm device 100 is used for laparoscopic surgery. However, in FIG. 3, the base part of the medical arm device 100 includes an attachment structure part 301 attached to a bed rail 310 provided along a length direction on a side part of a surgical bed.

By moving and fixing the attachment structure part 301 along the bed rail 310, an arrangement position of the medical arm device 100 can be adjusted according to an affected part position of a patient. When the inclination of the surgical bed is adjusted during surgery, a relative positional relationship between the patient and the medical arm device 100 can be maintained. During surgery, the surgical bed may be tilted by, for example, about 30 deg. Even in such a case, the medical arm device 100 according to the present disclosure can be used.

Furthermore, the medical arm device 100 can access a free space at hand of the surgeon from an opposite side of the surgeon across the patient (or the operating bed). In this manner, it is possible to avoid interference between the surgeon's hand or arm and the arm tip part by access from the surgeon's face.

C. Endoscope Holding Structure

Next, a structure for holding the endoscope 200 at the tip part of the medical arm device 100 will be described in more detail. As also illustrated in FIG. 2, the tip part of the medical arm device 100 includes the vertical rotation axis part 114 having a degree of freedom around the vertical rotation axis and swinging the endoscope 200 in the vertical direction, the left-right rotation axis part 115 adjacent to the vertical rotation axis part 114 and having a degree of freedom around the left-right rotation axis orthogonal to the vertical rotation axis and swinging the endoscope 200 in the left-right direction, and the optical axis rotation axis part 116 having a degree of freedom around the optical axis of the endoscope 200. Hereinafter, the optical axis rotation axis part 116 will be referred to as a roll axis, the left-right rotation axis part 115 will be referred to as a yaw axis, and the vertical rotation axis part 114 will be referred to as a pitch axis.

Figure 4:
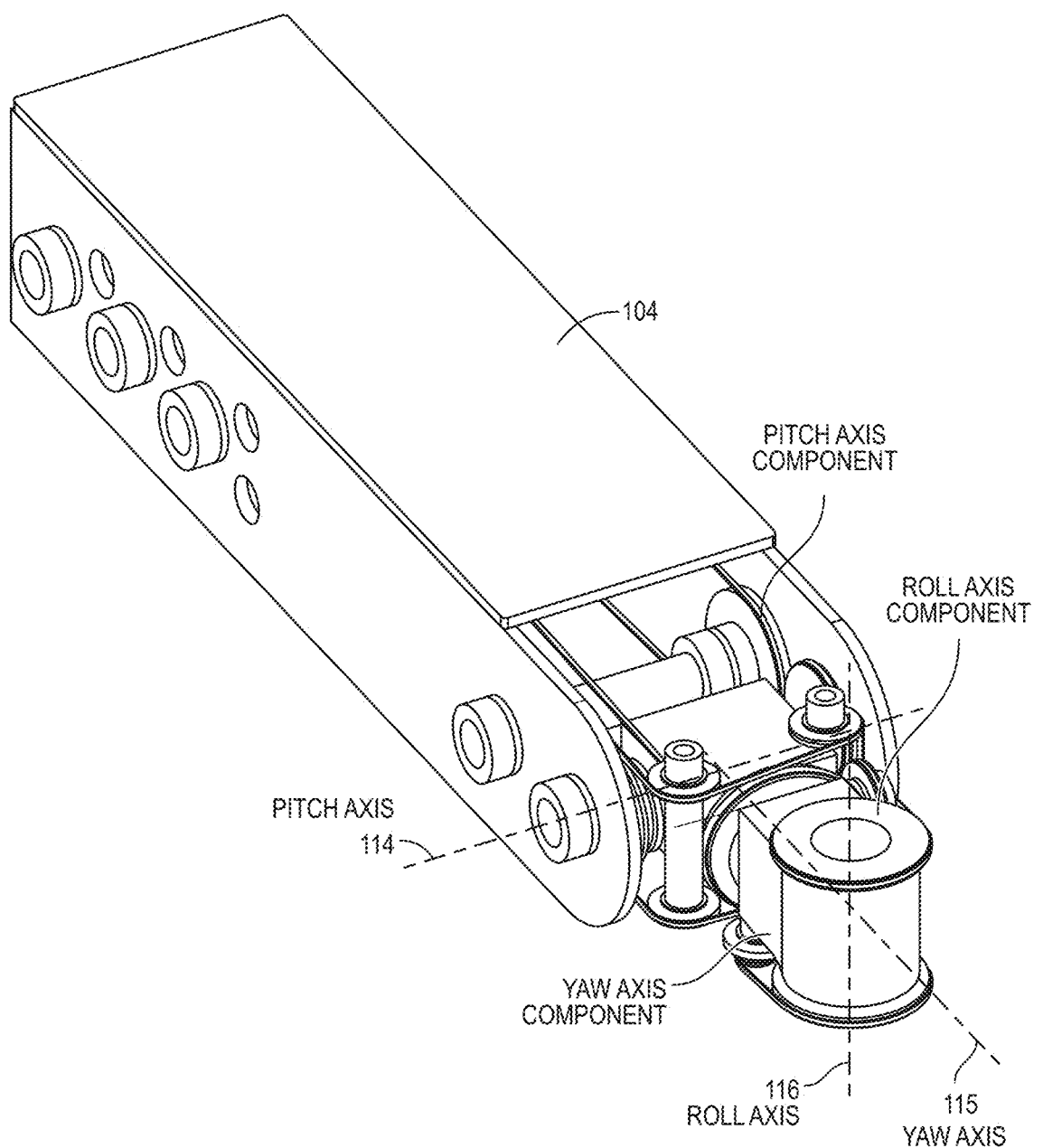
FIG. 4 is a diagram illustrating a specific structure of three axes of the tip part of the medical arm device 100.
Figure 5:
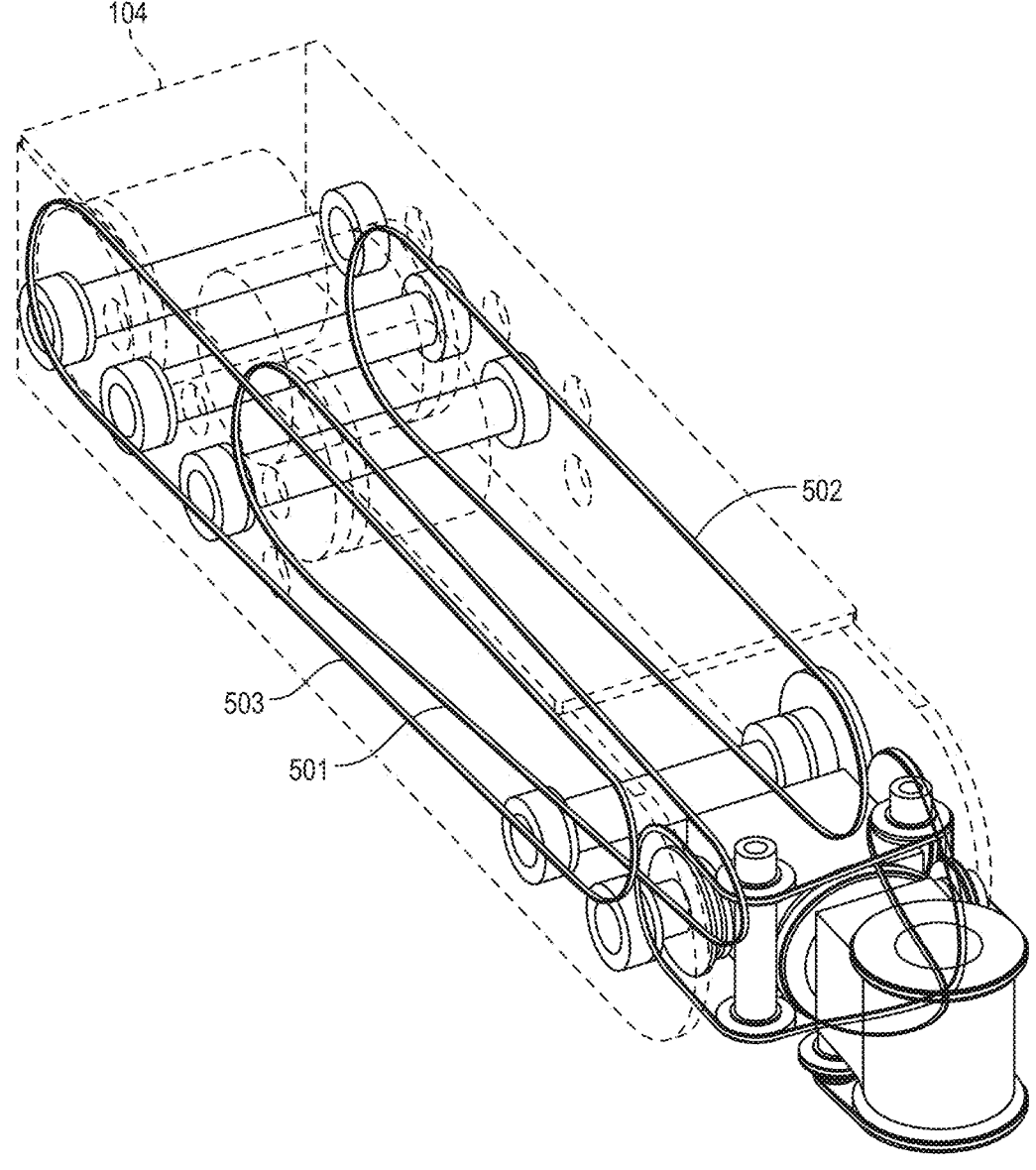
FIG. 5 is a diagram illustrating a structure of each of wires 501 to 503 pulling three axes of the tip part of the medical arm device 100.

FIG. 4 illustrates an example in which components of the roll axis 116, the yaw axis 115, and the pitch axis 114 are disposed at the tip of the fourth link 104. These three axes are active axes, but a driving system using a wire is applied in order to reduce a size of the tip. That is, motors that drive each of the axes of the roll axis 116, the yaw axis 115, and the pitch axis 114 are disposed on a root side (proximal end side) of the fourth link 104, and a driving force by an output of each motor is transmitted using a wire and a pulley. FIG. 5 illustrates structures of a pitch axis wire 501, a yaw axis wire 502, and a roll axis wire 503 that tow the components of the pitch axis 114, the yaw axis 115, and the roll axis 116, respectively. Furthermore, FIG. 6 illustrates a state where a pitch axis motor 601, a yaw axis motor 602, and a roll axis motor 603 that drive the pitch axis 114, the yaw axis 115, and the roll axis 116, respectively, are disposed at a base of the fourth link 104.

Figure 6:
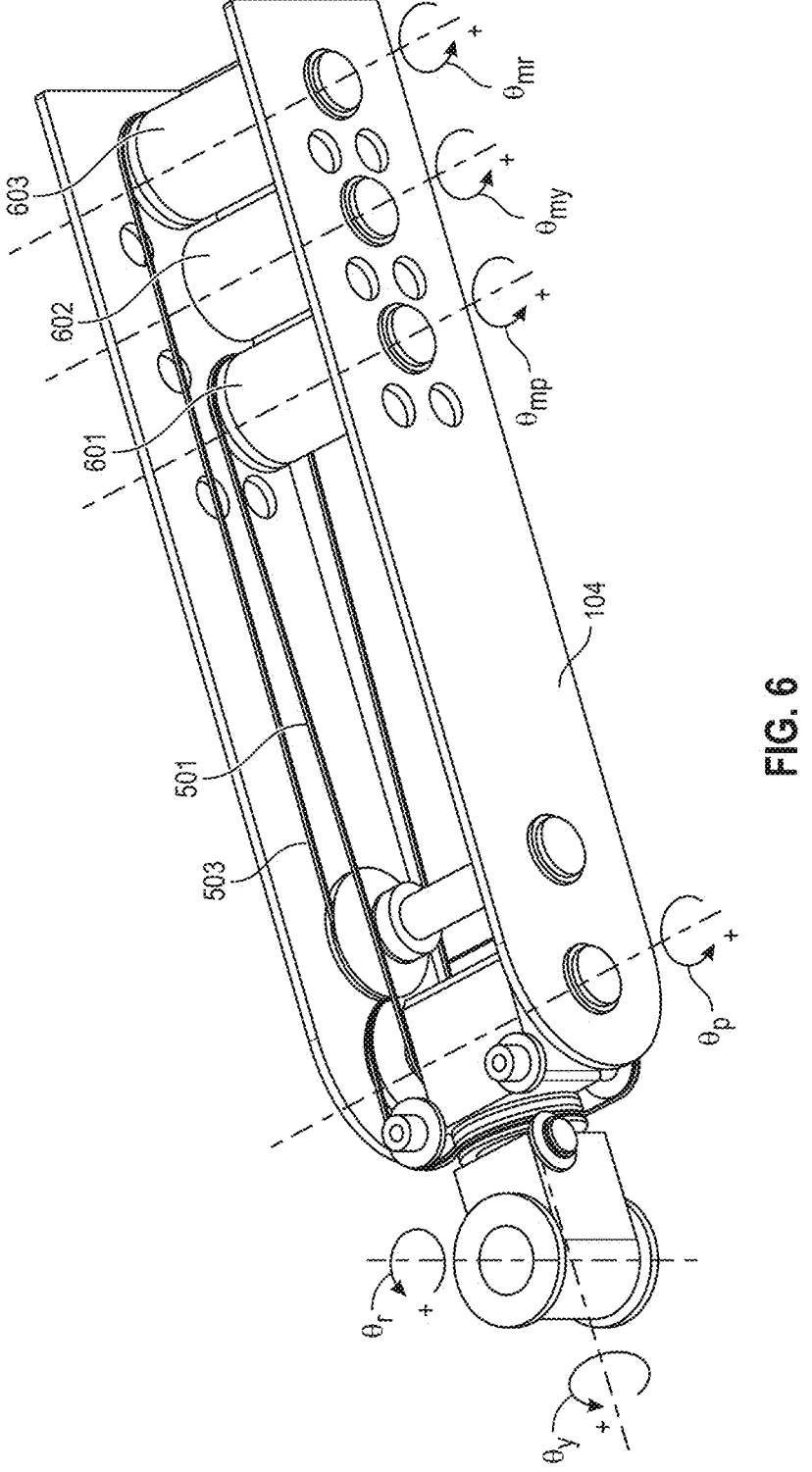
FIG. 6 is a diagram illustrating an arrangement example of a pitch axis motor 601, a yaw axis motor 602, and a roll axis motor 603.

As illustrated in FIG. 6, the motors 601 to 603 for each axis are disposed on the root side of the fourth link 104. Each of the motors 601 to 603 is fixed such that its rotation axis is parallel to the pitch axis 114. Then, as also illustrated in FIG. 5, the wires 501 to 503 are extended from output axis pulleys 611 to 613 of the motors 601 to 603 toward the tip part, respectively. The fourth link 104 extending each of the wires 501 to 503 long in a straight line corresponds to an "arm", and the three axes of the tip part of the fourth link correspond to a "wrist". If a site from the arm to the wrist can be configured to be thin as a whole, it is effective in avoiding interference between other medical instruments in an abdominal cavity and the tip part and collision between the arm and the surgeon's hand or arm. Therefore, as illustrated in FIG. 6, the motors 601 to 603 for each axis are preferably disposed in a line along a longitudinal direction of the arm, that is, the fourth link 104.

Furthermore, by disposing the motors 601 to 603 on the root side of the fourth link 104, a torque of a motor group (for example, a motor that drives the third joint part 113) further supporting the fourth link 104 is reduced. Therefore, it is preferable to dispose the motors 601 to 603 for each axis on the root side of the fourth link 104 as close as possible to each other.

C-1. Structure Around Pitch Axis

Figure 7:
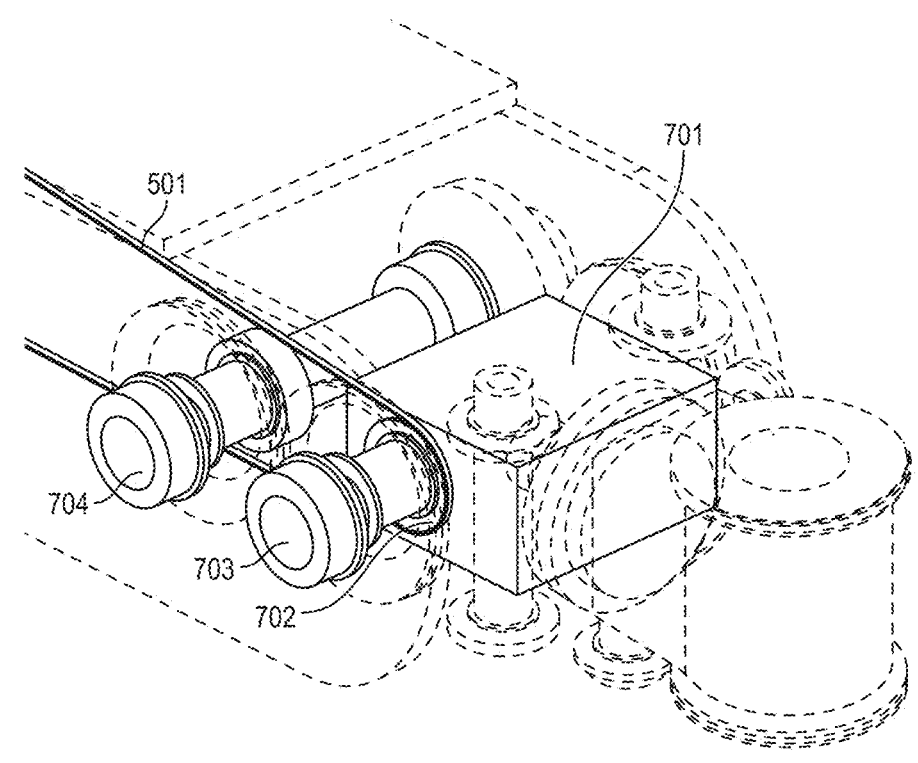
FIG. 7 is a diagram illustrating an extracted structure for realizing a rotational degree of freedom around a pitch axis 114 in the tip part of the medical arm device 100.

The pitch axis 114 corresponds to a tilt axis that vertically rotates the lens barrel 201 of the endoscope 200. In FIG. 7, a structure for realizing a rotational degree of freedom around the pitch axis 114 in the tip part of the medical arm device 100 is extracted and illustrated. Furthermore, in FIG. 7, an outline of other parts such as the fourth link 104 is indicated by a dotted line.

Near the tip of the fourth link 104, a pitch axis component 701 is supported by a shaft 703 coaxial with the pitch axis 114 so as to be rotatable around the pitch axis 114. Furthermore, as illustrated in FIG. 6, since the pitch axis motor 601 is disposed such that the output axis is parallel to the pitch axis 114, the other end of the pitch axis wire 501 wound around the output axis pulley 611 of the pitch axis motor 601 is wound around a pulley 702 integrated with the pitch axis component 701, so that the tip parts of the pitch axis component 701 and the subsequent parts can be rotationally driven around the pitch axis 114. In the example illustrated in FIG. 7, the pitch axis wire 501 is directly wound around the output axis of the pitch axis motor 601 and the pulley 702 without interposing other pulleys. However, the pitch axis wire 501 may be wound around the pulley 702 after a path is adjusted using other pulleys as necessary.

The pitch axis 114 (alternatively, the pitch axis component 701) can structurally have a rotation movable range of about ±120 deg. However, the pitch axis 114 is a tilt axis of the endoscope 200, and if considering holding the endoscope 200, a rotation movable range of about ±90 deg is sufficient. Rather, if the rotation movable range around the pitch axis 114 is too large, the endoscope 200 may collide with an arm such as the fourth link 104. As a structural design, in a case where the rotation movable range of the pitch axis 114 may be less than ±90 deg, the pulley 702 is only required to be a single-groove pulley as illustrated in FIG. 7. In a case where a rotation movable range of the pitch axis 114 of ±90 deg or more is required, the pitch axis wire 501 may be wound around different grooves in a forward path and a backward path with the pulley 702 as a two-groove pulley.

The structure for realizing the rotational degree of freedom around the pitch axis 114 illustrated in FIG. 7 is a simple structure in which an output torque of the pitch axis motor 601 disposed in parallel to the pitch axis 114 is transmitted to the pulley 702 by the pitch axis wire 501. It is easy to replace the output torque of the pitch axis motor 601 with a transmission mechanism such as a link mechanism or a gear mechanism other than the pitch axis wire 501 to form a structure for realizing the rotational degree of freedom around the pitch axis 114. Furthermore, the pitch axis 114 may be directly rotationally driven by the pitch axis motor 601 without using the transmission mechanism.

C-2. Structure Around Yaw Axis

Figure 8:
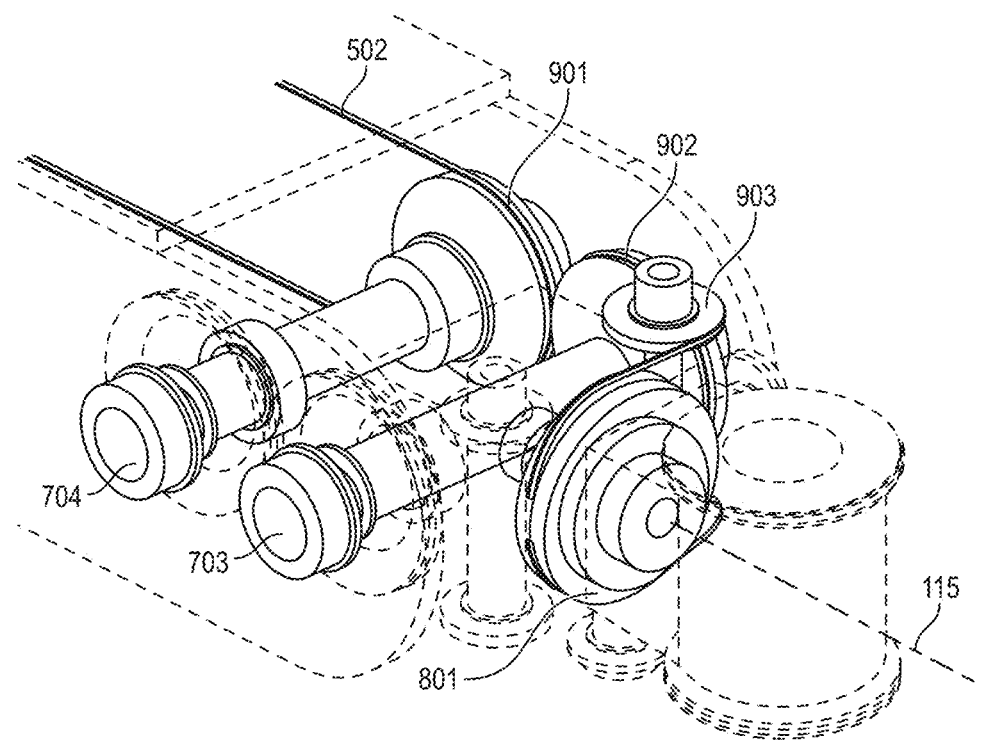
FIG. 8 is a diagram illustrating a structure for realizing a rotational degree of freedom around a yaw axis 115 in the tip part of the medical arm device 100.
Figure 9:
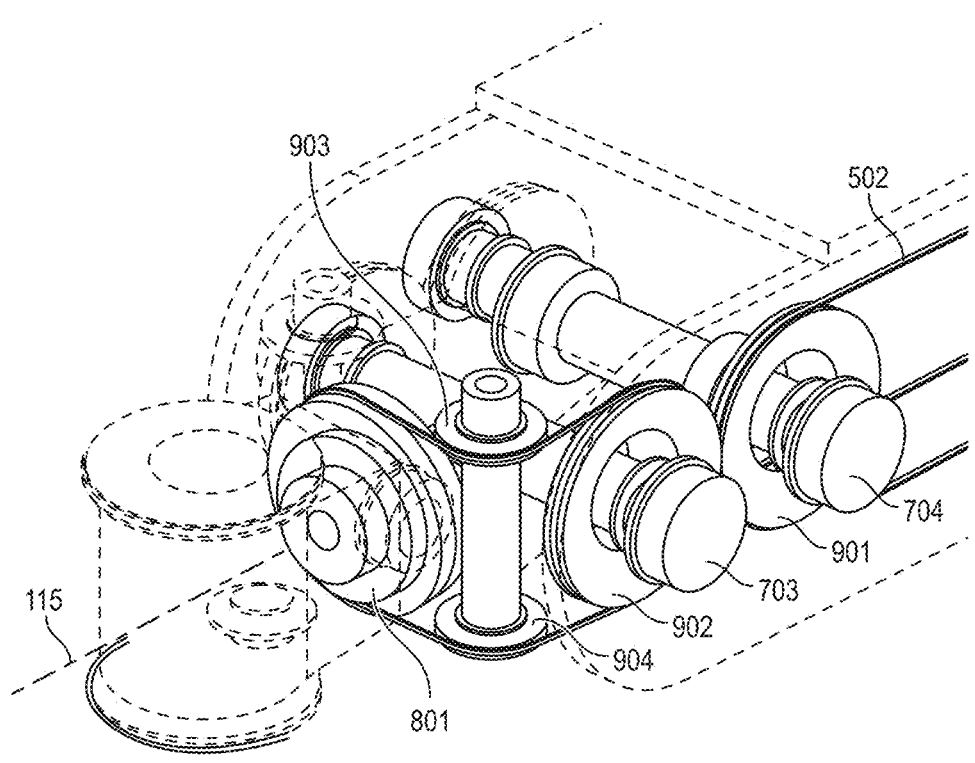
FIG. 9 is a diagram illustrating a structure for realizing a rotational degree of freedom around the yaw axis 115 in the tip part of the medical arm device 100.

The yaw axis 115 corresponds to a pan axis that changes the observation direction of the endoscope 200. In FIGS. 8 and 9, a structure for realizing the rotational degree of freedom around the yaw axis 115 in the tip part of the medical arm device 100 is extracted and illustrated. Furthermore, in FIGS. 8 and 9, an outline of other components such as the fourth link 104 is indicated by a dotted line.

A yaw axis pulley 801 is supported on a tip surface of the pitch axis component 701 (not illustrated in FIGS. 8 and 9) so as to be rotatable coaxially with the yaw axis 115. Furthermore, as illustrated in FIG. 6, the yaw axis motor 602 is disposed on the root side of the fourth link 104 such that the rotation axis is parallel to the pitch axis 114 together with the pitch axis motor 601 and the roll axis motor 603. Then, by winding the yaw axis wire 502 wound around the output axis pulley 612 of the yaw axis motor 602 around the yaw axis pulley 801 while adjusting the path via each of pulleys 901, 902, 903, and 904, the tip part of the yaw axis pulley 801 and the subsequent parts can be rotationally driven around the yaw axis 115.

A structure in which the yaw axis wire 502 is wound around the yaw axis pulley 801 will be specifically described. As a winding structure of the yaw axis wire 502, the two-groove pulley 901 that is rotatable around a rotation axis parallel to the pitch axis 114 on the root side of the pitch axis 114 and corresponds to rotation around the pitch axis 114, the two-groove pulley 902 that is rotatable around the pitch axis 114 and changes the path along the pitch axis 114, and the two rerouting pulleys 903 and 904 that change the path of the yaw axis wire 502 between the pitch axis and the yaw axis are used.

Figure 10:
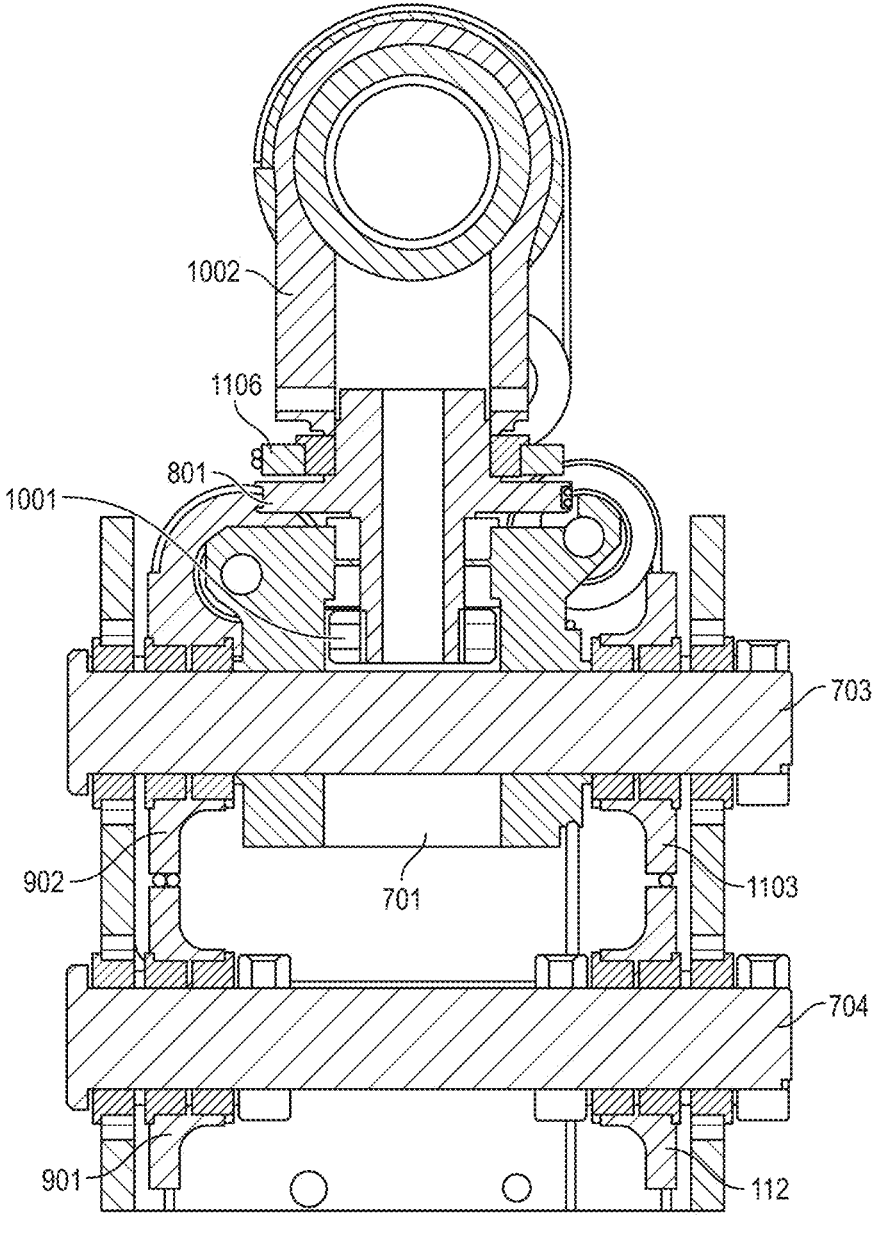
FIG. 10 is a diagram illustrating a cross section of the tip part of the medical arm device 100.

The two-groove pulley 901 is rotatably supported around a rotation axis parallel to the pitch axis 114 by the shaft 704 on the root side of the pitch axis 114, and the two-groove pulley 902 is rotatably supported around the pitch axis 114 by the shaft 703 coaxial with the pitch axis 114 (See the above and FIG. 10.). Furthermore, the rerouting pulleys 903 and 904 are supported on side surfaces on an opposite side of the pitch axis component 701 (not illustrated in FIGS. 8 and 9) so as to be rotatable on the identical axis around an axis orthogonal to the pitch axis 114 and the yaw axis 115.

On a forward path side, when the yaw axis wire 502 comes out of the output axis pulley 612 (not illustrated in FIGS. 8 and 9) of the yaw axis motor 602, the yaw axis wire is wound around the two-groove pulley 901 on the root side and the two-groove pulley 902 coaxial with the pitch axis 114 in this order from the longitudinal direction (or the pitch axis direction) of the fourth link 104 to change the path along the pitch axis, then wound around the rerouting pulley 903 to change the path from the pitch axis direction to the yaw axis direction, and wound around the yaw axis pulley 801.

Furthermore, on a backward path side, when the yaw axis wire 502 is wound around the rerouting pulley 904 immediately after coming out of the yaw axis pulley 801 and rerouted from the yaw axis direction to the pitch axis direction, the yaw axis wire is wound around the two-groove pulley 902 coaxial with the pitch axis 114 and the two-groove pulley 901 on the root side in this order to change the route along the pitch axis, and then wound around the output axis pulley 612 (not illustrated in FIGS. 8 and 9) of the yaw axis motor 602.

Next, a method of fixing the yaw axis pulley 801 and the yaw axis wire 502 will be considered. The yaw axis pulley 801 is a two-groove pulley, and the forward path and the backward path of the yaw axis wire 502 are fixed to different grooves, so that the yaw axis 115 can have a rotation movable range of ±90 deg or more. However, in the present embodiment, as a basic structure, the rotation movable range around the yaw axis 115 is ±80 deg. The larger a diameter of the yaw axis pulley 801 is, the larger a transmission torque can be handled, which is preferable. It is important for simplification of the structure that the diameter of each groove of the two-groove pulley used for the yaw axis pulley 801 is the same.

In the configuration example illustrated in FIGS. 8 and 9, two rerouting pulleys 903 and 904 are used to reroute the yaw axis wire 502 between the pitch axis and the yaw axis. If the rerouting pulleys 903 and 904 are configured by disposing two pulleys having different diameters on the identical axis in order to reduce the number of parts and simplify the structure, the yaw axis wire 502 can be smoothly rerouted with good compatibility with the two-groove pulley 902. In the example illustrated in FIG. 9, a diameter of the rerouting pulley 904 is larger than that of the rerouting pulley 903. Therefore, on the forward path side of the yaw axis wire 502, the path is changed from the pitch axis direction to the yaw axis direction by the rerouting pulley 903 while being wound around a groove inside the two-groove pulley 902, and on the backward path side of the yaw axis wire 502, the path is changed from the yaw axis direction to the pitch axis direction by the rerouting pulley 904, and then the yaw axis wire is wound around a groove outside the two-groove pulley 902.

Furthermore, in order to change the path of the yaw axis wire 502 along the pitch axis direction, it is important that the diameter of each groove of the two-groove pulley 902 coaxial with the pitch axis 114 is the same, and it is further preferable that the diameter is the same as a diameter of the yaw axis pulley 801 in terms of design.

Furthermore, the diameter of each groove of the two-groove pulley 901 on the root side of the pitch axis 114 is not necessarily the same. From the viewpoint of weight reduction, the two-groove pulley 901 is preferably small.

FIG. 10 is a cross-sectional view of the tip part of the medical arm device 100 taken along a plane (alternatively, a plane orthogonal to the roll axis) parallel to the pitch axis and the yaw axis. As illustrated in the figure, a first connection part 1001 connected to the pitch axis component 701 is disposed on the root side (or proximal end side) of the yaw axis pulley 801. Furthermore, a second connection part 1002 connected to a roll axis component (roll axis pulley) as described later is disposed on a tip side (alternatively, a distal end side) of the yaw axis pulley 801. The yaw axis pulley 801, and the first connection part 1001 and the second connection part 1002 are integrally fastened by a fixing method such as a screw to constitute a yaw axis component. Therefore, when the yaw axis pulley 801 is rotated around the yaw axis, the first connection part 1001 and the second connection part 1002 are also interlocked. The roll axis component also rotates around the yaw axis 115 following the second connection part 1002.

Note that FIG. 10 also illustrates an arrangement of a bearing. In FIG. 10, a bearing part is filled with a dot pattern. The yaw axis component is supported at the first connection part 1001 via the bearing to be rotatable around the yaw axis 115 relative to the pitch axis component 701. Furthermore, the yaw axis component supports a roll axis component (described later) (not illustrated) via the bearing so as to be rotatable around the roll axis 116 at the second connection part 1002.

The two-groove pulley 901 for accommodating rotation around the pitch axis 114 is supported by the shaft 704 having a rotation axis parallel to the pitch axis 114 via a bearing, and is rotatable coaxially with the shaft 704. The two-groove pulley 902 for rerouting along the pitch axis 114 is supported by the shaft 703 coaxial with the pitch axis 114 via the bearing, and is rotatable coaxially with the shaft 703, that is, around the pitch axis 114.

Furthermore, as will be described later, a two-groove pulley 1102 for accommodating rotation around the pitch axis 114 and a two-groove pulley 1103 for changing the path along the pitch axis 114 are used as components for realizing the rotational degree of freedom around the roll axis. The two-groove pulley 1102 is supported by the shaft 704 having a rotation axis parallel to the pitch axis 114 via the bearing, and is rotatable coaxially with the shaft 704. The two-groove pulley 1103 is supported by the shaft 703 coaxial with the pitch axis 114 via the bearing, and is rotatable coaxially with the shaft 703, that is, around the pitch axis 114.

C-3. Structure Around Roll Axis

Figure 11:
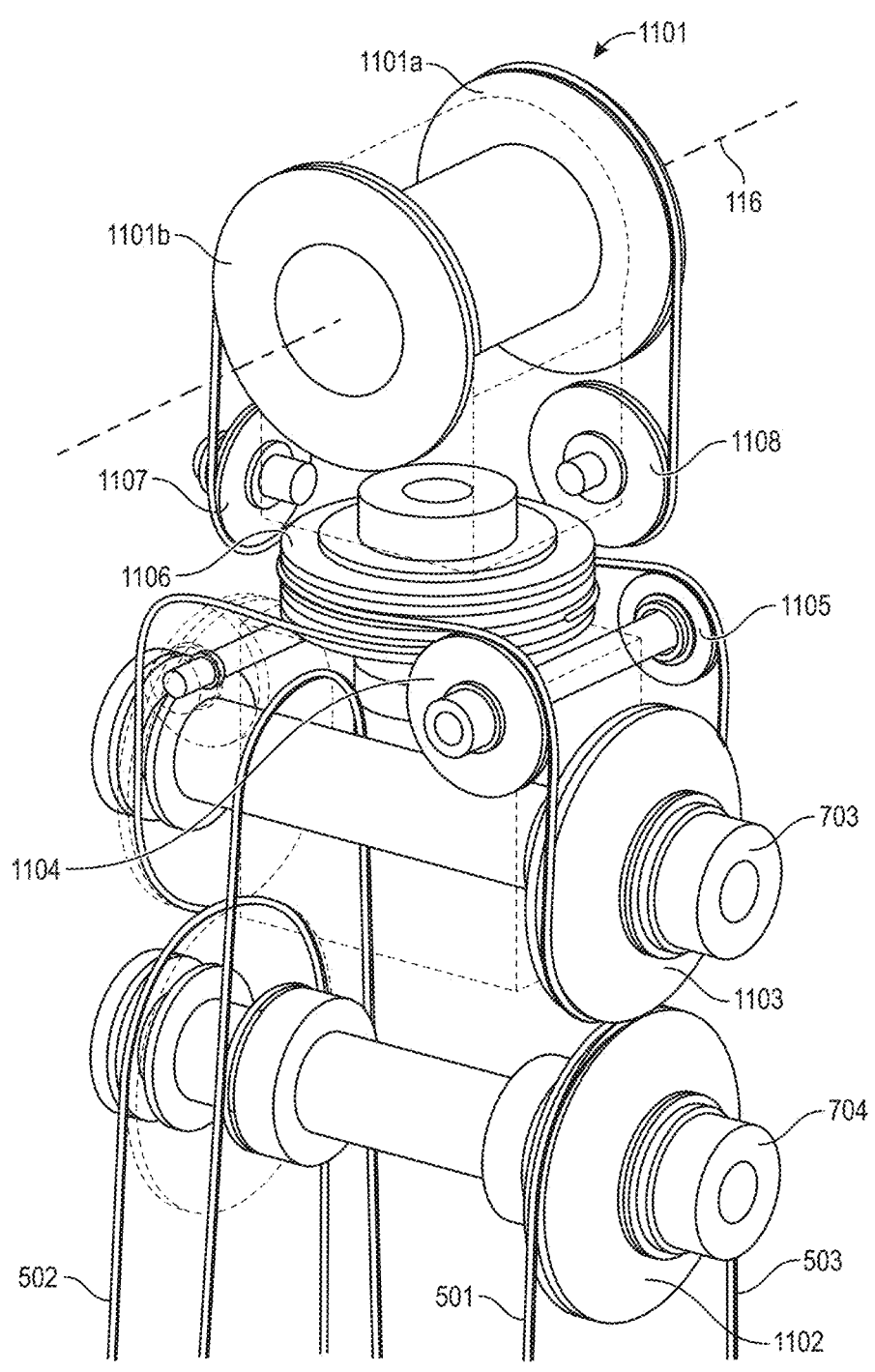
FIG. 11 is a diagram illustrating a structure for realizing a rotational degree of freedom around a roll axis 116 in the tip part of the medical arm device 100.
Figure 12:
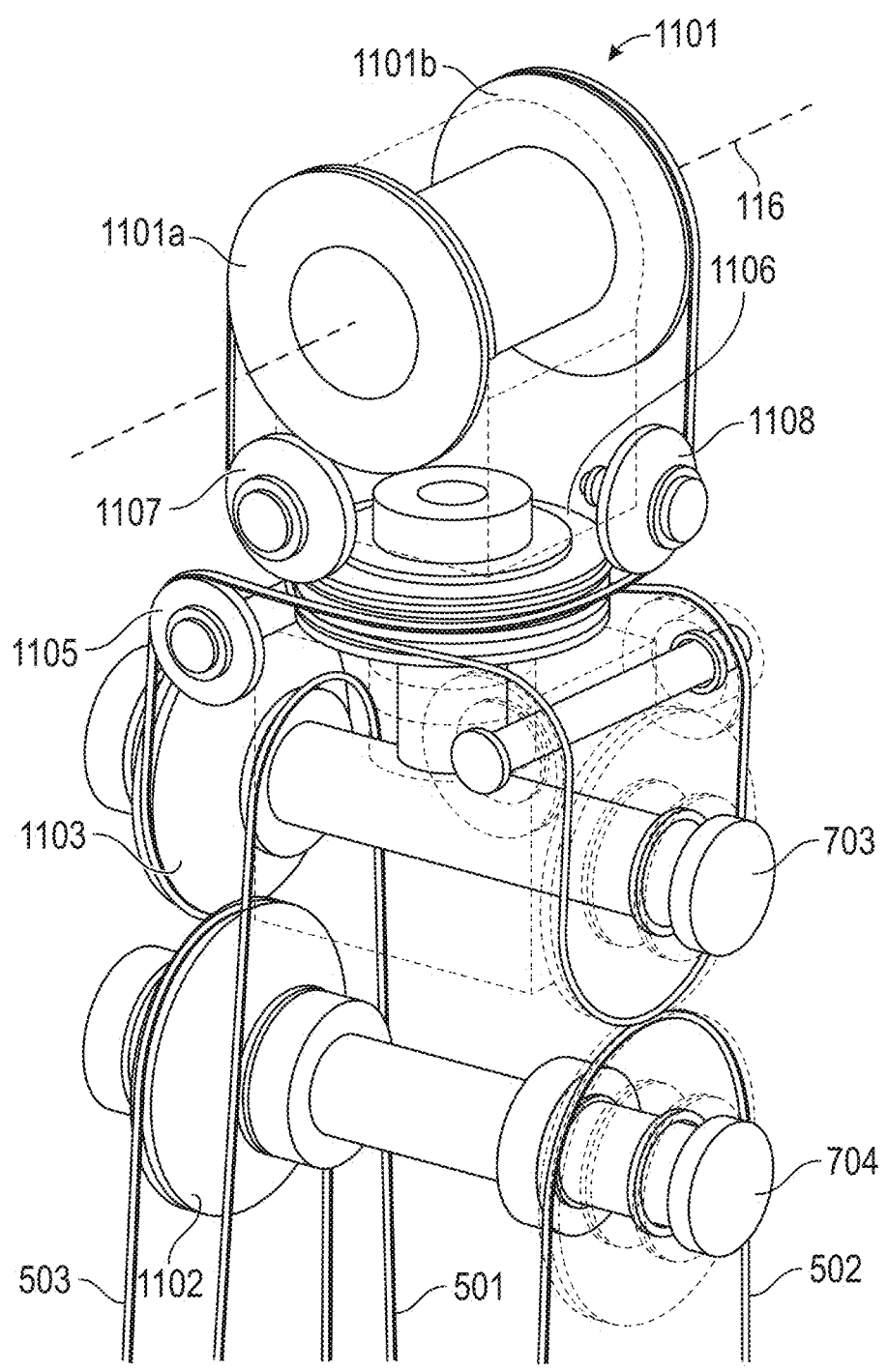
FIG. 12 is a diagram illustrating a structure for realizing a rotational degree of freedom around the roll axis 116 in the tip part of the medical arm device 100.

The roll axis 116 corresponds to an optical axis of the lens barrel 201 of the endoscope 200. In FIGS. 11 and 12, a structure for realizing the rotational degree of freedom around the roll axis 116 in the tip part of the medical arm device 100 is extracted and illustrated. Furthermore, in FIGS. 11 and 12, an outline of other components such as the fourth link 104 is indicated by a dotted line.

The roll axis pulley 1101 is supported by the tip part of the second connection part 1002 via a bearing so as to be rotatable around the roll axis 116 (see FIG. 10). The roll axis pulley 1101 is a structure body including a hollow cylinder, and includes pulleys 1101a and 1101b for winding a set of a forward path and a backward path of the roll axis wire 503 around both ends of the cylinder. One set of the pulleys 1101a and 1101b is integrally fastened so as to rotate around the roll axis 116 to constitute the pulley 1101. Although not illustrated in FIGS. 11 and 12, the endoscope 200 is attached inside a cylinder of the roll axis pulley 1101. Furthermore, as illustrated in FIG. 6, the roll axis motor 603 is disposed on the root side of the fourth link 104 such that the rotation axis is parallel to the pitch axis 114 together with the pitch axis motor 601 and the yaw axis motor 602. Then, both ends of the roll axis wire 503 wound around the output axis pulley 613 of the roll axis motor 603 are respectively wound around the set of pulleys 110a1 and 1101b of the roll axis pulley 1101 via a plurality of the pulleys 1102, 1103, . . . , so that the endoscope 200 (or the lens barrel 201) attached to the roll axis pulley 1101 can be rotationally driven around the roll axis 116.

A structure in which the roll axis wire 503 is wound around the roll axis pulley 1101 will be specifically described. As the winding structure of the roll axis wire 503, the two-groove pulley 1102 that is rotatable around a rotation axis parallel to the pitch axis 114 on the root side of the pitch axis 114 and accommodates rotation around the pitch axis 114, the two-groove pulley 1103 that is rotatable around the pitch axis 114 and changes the path along the pitch axis 114, two rerouting pulleys 1104 and 1105 that change the path of the roll axis wire 503 between the pitch axis and the yaw axis, a two-groove pulley 1106 coaxial with the yaw axis 115 that changes the path along the yaw axis 115, and two rerouting pulleys 1107 and 1108 that change the path of the roll axis wire 503 between the yaw axis and the roll axis are used.

The two-groove pulley 1102 is rotatably supported around a rotation axis parallel to the pitch axis 114 by the shaft 704 on the root side of the pitch axis 114, and the two-groove pulley 1103 is rotatably supported around the pitch axis 114 by the shaft 703 coaxial with the pitch axis 114 (See the above and FIG. 10.). The rerouting pulleys 1104 and 1105 are respectively supported on side surfaces on an opposite side of the pitch axis component 701 (not illustrated in FIGS. 8 and 9) so as to be rotatable on the identical axis around an axis orthogonal to the pitch axis 114 and the yaw axis 115. The two-groove pulley 1106 is supported on a tip surface of the pitch axis component 701 via a bearing so as to be rotatable around the yaw axis 115 (See FIG. 10.). The rerouting pulley 1107 is supported on a side surface of the second connection part 1002 (not illustrated in FIGS. 11 and 12) so as to be rotatable around an axis parallel to the roll axis 116. Furthermore, the reroute 1108 is supported on a side surface of the second connection part 1002 (not illustrated in FIGS. 11 and 12) so as to be rotatable around an axis orthogonal to the roll axis 116.

On the forward path side, when the roll axis wire 503 comes out of the output axis pulley 613 (not illustrated in FIGS. 11 and 12) of the roll axis motor 603, the roll axis wire is wound around the rerouting pulley to change the route along the pitch axis by winding the two-groove pulley 1102 on the root side and the two-groove pulley 1103 coaxial with the pitch axis 114 in this order from the longitudinal direction (or the pitch axis direction) of the fourth link 104, then wound around the rerouting pulley 1104 to change the path from the pitch axis direction to the yaw axis direction, then wound around the two-groove pulley 1106 to change the path along the yaw axis, further wound around the rerouting pulley 1107 to change the path from the yaw axis direction to the roll axis direction, and wound around one pulley 1101a of the roll axis pulley 1101.

Furthermore, on the backward path side, the roll axis wire 503 is wound around the rerouting pulley 1108 immediately after coming out of the other pulley 1101b of the roll axis pulley 1101 to change the path from the roll axis direction to the yaw axis direction, then wound around the two-groove pulley 1106 to change the path along the yaw axis, further wound around the rerouting pulley 1105 to change the path from the yaw axis direction to the pitch axis direction, then wound around the two-groove pulley 1103 coaxial with the pitch axis 114 and the two-groove pulley 1102 on the root side in this order to change the path along the pitch axis, and then wound around the output axis pulley 613 (not illustrated in FIGS. 11 and 12) of the roll axis motor 603.

Next, a method of fixing the roll axis pulley 1101 and the roll axis wire 503 will be considered. The roll axis pulley 1101 includes a set of pulleys 1101a and 1101b, but may be a two-groove pulley similarly to the yaw axis. In the present embodiment, as a basic structure, the rotation movable range around the roll axis 116 is ±170 deg. A diameter of the set of pulleys 1101a and 1101b of the roll axis pulley 1101 needs to be the same. It is preferable that these diameters are larger because a larger transmission torque can be handled.

In the example illustrated in FIGS. 11 and 12, the two rerouting pulleys 1107 and 1108 that reroute the roll axis wire 503 between the yaw axis and the roll axis are used, but one of the pulleys interferes with the two rerouting pulleys 1104 and 1105 that reroute the roll axis wire 503 between the pitch axis and the yaw axis. In order to avoid such interference between the pulleys, as described above, the rotation movable range around the yaw axis 115 is ±80 deg.

In order to change the path along the pitch axis, the two-groove pulley 1102 on the root side of the pitch axis 114 and the two-groove pulley 1103 coaxial with the pitch axis 114 are used, but it is important that these two-groove pulleys 1102 and 1103 have the same diameter as each other. Further, it is preferable in design that these two-groove pulleys 1102 and 1103 have the same diameter as the roll axis pulley 1101.

In the examples illustrated in FIGS. 11 and 12, the two rerouting pulleys 1104 and 1105 that reroute the roll axis wire 503 between the pitch axis and the yaw axis are used. However, in order to reduce the number of parts and simplify the structure, when the rerouting pulleys 1104 and 1105 are configured by disposing two pulleys having different diameters on the identical axis, the roll axis wire 503 can be smoothly rerouted with good compatibility with the two-groove pulley 1103. In the example illustrated in FIGS. 11 and 12, a diameter of the rerouting pulley 1104 is larger than that of the rerouting pulley 1105. Therefore, on the forward path side of the roll axis wire 503, the path is changed from the yaw axis direction to the pitch axis direction by the rerouting pulley 1104 while being wound around a groove inside the two-groove pulley 1103, and on the backward path side of the roll axis wire 503, the path is changed from the pitch axis direction to the yaw direction by the rerouting pulley 1105, and then the roll axis wire is wound around the outside of the two-groove pulley 1104.

Furthermore, in order to change the path of the roll axis wire 503 along the pitch axis direction, it is important that the diameter of each groove of the two-groove pulley 1103 coaxial with the pitch axis 114 is the same, and it is further preferable that the diameter is the same as that of the yaw axis pulley 801 in terms of design.

Furthermore, the diameter of each groove of the two-groove pulley 1102 on the root side of the pitch axis 114 is not necessarily the same. From the viewpoint of weight reduction, the two-groove pulley 1102 is preferably small.

As described with reference to FIGS. 4 to 12, the basic structure has a structure in which the motors 601 to 603 for three-axis drive are disposed as close as possible to each other, and the tip part can be driven by wire drive.

Note that regarding the drive of the pitch axis 114, only the rotation between two parallel axes, that is, the pitch axis 114 and the output axis of the pitch axis motor 501 is transmitted. Therefore, it is possible to replace the transmission method with any transmission method such as a belt, a gear, or a link mechanism.

D. Regarding Control of Tip Part

Next, a method of controlling the tip part described in section C described above will be described. First, symbols used in the following description will be described.

Radius of pulley 702 for driving pitch axis 114: $R_p$
Rotation angle of pitch axis 114: $\theta_p$
Radius of yaw axis pulley 801 for driving yaw axis 115: $R_y$
Rotation angle of yaw axis 115: $\theta_y$

14

Radius of roll axis pulley 1101 for driving roll axis 116: $R_r$
Rotation angle of roll axis 116: $\theta_r$
Radius of pulley 902 coaxial with pitch axis 114 for driving yaw axis 115: $R_{py}$
Radius of pulley 1103 coaxial with pitch axis 114 for driving roll axis 116: $R_{pr}$
Radius of pulley 1103 coaxial with yaw axis 115 for driving roll axis 116: $R_{yr}$
Rotation angle of output axis of pitch axis motor 601: $\theta_{mp}$
Radius of output axis pulley 611 of pitch axis motor 601: $R_{mp}$
Rotation angle of output axis of yaw axis motor 602: $\theta_{my}$
Radius of output axis pulley 612 of yaw axis motor 602: $R_{my}$
Rotation angle of output axis of roll axis motor 603: $\theta_{mr}$
Radius of output axis pulley 613 of roll axis motor 603: $R_{mr}$ Furthermore, the definitions of the positive and negative directions of the rotation of the pitch axis 114, the yaw axis 115, the roll axis 116, and the output axes of the motor 601 to 603 for each axis are as illustrated in FIG. 6.

Inverse kinematics is obtained on the basis of the conditions described above. The rotation angles $\theta_{mp}$, $\theta_{my}$, and $\theta_{mr}$ of the output axes of the motors 601 to 603 for driving each axis are derived as in the following formulas (1) to (3) on the basis of the respective rotation angles $\theta_p$, $\theta_y$, and $\theta_r$ of the pitch axis 114, the yaw axis 115, and the roll axis 116 at the tip part.

[Mathematical formula 1]

$$\theta_{mp} = \theta_p \frac{R_p}{R_{mp}} \tag{1}$$

[Mathematical formula 2]

$$\theta_{my} = -\theta_y \frac{R_y}{R_{my}} - \theta_p \frac{R_{py}}{R_{my}} \tag{2}$$

[Mathematical formula 3]

$$\theta_{mr} = -\theta_r \frac{R_r}{R_{mr}} + \theta_y \frac{R_{yr}}{R_{mr}} - \theta_p \frac{R_{pr}}{R_{mr}} \tag{3}$$

Here, the rotation angle $\theta_{mp}$, $\theta_{my}$, or $\theta_{mr}$ of the output axis of each of the motors 601 to 603 can be measured by an encoder attached to the output axis of each of the motors 601 to 603.

In a case where each of the rotation angles $\theta_p$, $\theta_y$, and $\theta_r$ of the pitch axis 114, the yaw axis 115, and the roll axis 116 of the tip part is obtained by forward kinematics, it is only necessary to arrange the simultaneous equations (1) to (3) described above with respect to each of the rotation angles $\theta_p$, $\theta_y$, and Gr, and the rotation angles $\theta_p$, $\theta_y$, and Gr are obtained as the following formulas (4) to (6).

[Mathematical formula 4]

$$\theta_p = \theta_{mp} \frac{R_{mp}}{R_p} \tag{4}$$

[Mathematical formula 5]

$$\theta_y = -\theta_{my} \frac{R_{my}}{R_y} - \theta_{mp} \frac{R_{mp}R_{py}}{R_pR_y} \tag{5}$$

15

-continued

[Mathematical formula 6]

$$\theta_r = -\theta_{mr}\frac{R_{mr}}{R_r} - \theta_{my}\frac{R_{my}R_{yr}}{R_yR_r}$$
$$-\theta_{mp}\frac{R_{mp}R_{py}R_{yr}}{R_pR_yR_r} - \theta_{mp}\frac{R_{mp}R_{pr}}{R_pR_r} \quad (6)$$

By using the above formulas (1) to (6), it is possible to derive a rotation movable range that needs to be adaptable to each motor and each pulley.

First, the rotation movable range of each of the joint angles $\theta_p$, $\theta_y$, and $\theta_r$ of the pitch axis 114, the yaw axis 115, and the roll axis 116 is set in a range represented by the following formula (7), (8), or (9), as described above.

[Mathematical formula 7]

$$-90 \leq \theta_p \leq 90 \text{ deg} \quad (7)$$

[Mathematical formula 8]

$$-80 \leq \theta_y \leq 80 \text{ deg} \quad (8)$$

[Mathematical formula 9]

$$-170 \leq \theta_r \leq 170 \text{ deg} \quad (9)$$

By setting $R_y = R_{py}$ and $R_r = R_{pr} = R_{yr}$ in terms of a mechanical design, it is possible to generate the path of the wires 501 to 503 simply, at low cost, and smoothly. By substituting the values described above in consideration of this, the rotation angle $\theta_{mp}$, $\theta_{ray}$, or $\theta_{mr}$ of the output axis of each motor 601, 602, or 603 necessary for realizing the rotation movable range of each joint shown in the above formula (7), (8), or (9) can be simply calculated as in the following formula (10), (11), or (12).

[Mathematical formula 10]

$$\theta_{mp} = \pm 90 \frac{R_p}{R_{mp}} \quad (10)$$

[Mathematical formula 11]

$$\theta_{my} = \pm 170 \frac{R_y}{R_{my}} \quad (11)$$

[Mathematical formula 12]

$$\theta_{mr} = \pm 340 \frac{R_r}{R_{mr}} \quad (12)$$

Strictly speaking, although it depends on the design, rotation movable ranges in which the rotation angle $\theta_{mp}$ of the output axis of the pitch axis motor 601 is about half rotation, the rotation angle $\theta_{my}$ of the output axis of the yaw axis motor 602 is about one rotation, and the rotation angle $\theta_{mr}$ of the output axis of the roll axis motor 603 is about two rotations are required. Therefore, the wire 503 is spirally wound around the output axis pulley 613 of the roll axis motor 603 so as to be rotatable by two or more rotations.

Incidentally, one rotation is insufficient for an absolute encoder mounted on an output axis of a motor requiring a rotation movable range exceeding one rotation. Therefore, it is necessary to mount a multi-rotation absolute encoder or mount an absolute encoder in a joint part (for example, the roll axis pulley 1101).

A multi-rotation absolute encoder generally needs to hold what rotation it is, and examples thereof include a method of mounting a battery and electrically holding the absolute encoder or a method of mechanically holding the absolute encoder using a structure such as a screw, but there is a problem that the number of parts and weight increase in any method. On the other hand, in a case where the absolute encoder is mounted in the joint part, there is a problem that the number of wires to the tip part of the arm increases, and it is necessary to devise wiring, and the weight of the tip part increases, so that the load of each of the motor 601 to 603 also increases.

Therefore, in the present disclosure, a method of deriving the number of rotations from a measurement value of the one-rotation absolute encoder is used for the output axis of the roll axis motor 603.

The rotation angle $\theta_{mp}$, $\theta_{my}$, or $\theta_{mr}$ of the output axis of the motor 601, 602, or 603 for each axis corresponding to each of the target angles $\theta_p$, $\theta_y$, and $\theta_r$ of the pitch axis 114, the yaw axis 115, and the roll axis 116 was derived using the inverse kinematics shown in the above formulas (1) to (3) so as to cover all the attitudes of the tip part. As a result, it has been found that the rotation angles $\theta_{mp}$, $\theta_{my}$, and $\theta_{mr}$ of the output axes of the motors 601 to 603 for each axis vary within the ranges of the following formulas (13) to (15), respectively, which are consistent with the results of the simple calculation shown in the above formulas (10) to (12).

[Mathematical formula 13]

$$-90 \leq \theta_{mp} \leq 90 \text{ deg} \quad (13)$$

[Mathematical formula 14]

$$-180 \leq \theta_{my} \leq 180 \text{ deg} \quad (14)$$

[Mathematical formula 15]

$$-360 \leq \theta_{mr} \leq 360 \text{ deg} \quad (15)$$

Here, it is assumed that a one-rotation absolute encoder is mounted on the roll axis 116, and the rotation angle $\theta_r$ of the roll axis 116 can be measured in a range of 0 to 360 deg. Then, a value obtained by converting the rotation angle $\theta_{mr}$ of the output axis of the roll axis motor 603 so as to fall within this angle range is set as a pseudo roll axis motor output rotation angle $\theta_{mr\_1}$.

Therefore, it is sufficient that the forward kinematics calculation shown in the above formulas (4) to (6) is performed using this value $\theta_{mr\_1}$ instead of the original rotation angle $\theta_{mr}$ of the motor output axis, and the attitude of the tip part can be derived similarly.

When each of the target angles $\theta_p$, $\theta_y$, and $\theta_r$ of the pitch axis 114, the yaw axis 115, and the roll axis 116 is calculated by the forward kinematics calculation using the value $\theta_{mr\_1}$ so as to cover all the attitudes of the tip part, it can be confirmed that a value matching the original target value (that is, when calculated using the original value $\theta_{mr}$) can be derived for each of the target angles $\theta_p$ and $\theta_y$ of the pitch axis 114 and the yaw axis 115. On the other hand, with respect to the target angle $\theta_{r\_1r}$ of the roll axis 116 derived using an alternative value $\theta_{mr\_1r}$, it has been confirmed that the value is divided into two groups, and one group is lower than −170 deg that is a rotation movable range limit of the roll axis 116. This is because, by using a one-rotation absolute encoder for the output axis of the roll axis motor 603, a numerical value such as −10 deg is originally measured as 350 deg. Therefore, in the present disclosure, the forward kinematics described in the above formulas (4) to (6) is corrected to the following formulas (16) to (19).

17

[Mathematical formula 16]

$$\theta_p = \theta_{mp} \frac{R_{mp}}{R_p} \tag{16}$$

[Mathematical formula 17]

$$\theta_y = -\theta_{my} \frac{R_{my}}{R_y} - \theta_{mp} \frac{R_{mp}R_{py}}{R_p R_y} \tag{17}$$

[Mathematical formula 18]

$$\theta_{r\_1r} = -\theta_{mr} \frac{R_{mr}}{R_r} - \theta_{my} \frac{R_{my}R_{yr}}{R_y R_r} \tag{18}$$
$$-\theta_{mp} \frac{R_{mp}R_{py}R_{yr}}{R_p R_y R_r} - \theta_{mp} \frac{R_{mp}R_{pr}}{R_p R_r}$$

[Mathematical formula 19]

$$\theta_r = \theta_{r\_1r} \tag{19}$$

(However, when $\theta_{r\_1r} > 180 \ deg$)

[Mathematical formula 20]

$$\theta_r = -(\theta_{mr} - 360deg) \frac{R_{mr}}{R_r} - \theta_{my} \frac{R_{my}R_{yr}}{R_y R_r} \tag{20}$$
$$-\theta_{mp} \frac{R_{mp}R_{py}R_{yr}}{R_p R_y R_r} - \theta_{mp} \frac{R_{mp}R_{pr}}{R_p R_r}$$

(However, when $\theta_{r\_1r} \leq 180 \ deg$)

It could be confirmed that the original attitude of the tip part could be derived using the forward kinematics represented by the above formulas (16) to (20). Therefore, by introducing the correction calculation using the above formulas (19) and (20), it can be seen that the attitude of the tip part can be easily derived using the forward kinematics represented by the above formulas (16) to (20) only by mounting the one-rotation absolute encoder on the output axis of the motors 601 to 603 for each axis.

However, in order to establish the correction calculation using the above formulas (19) and (20), it is required that the radius $R_{mr}$ of the output axis pulley 611 of the roll axis motor 603 is larger than the radius $R_r$ of the roll axis pulley 1101, that is, the following formula (21) is satisfied. Therefore, the rotation movable range of the rotation angle $\theta_{mr}$ of the output axis of the roll axis motor 603 can be suppressed to within two rotations.

[Mathematical formula 21]

$$R_r \leq R_{mr} \tag{21}$$

Note that in terms of safely transmitting a large torque, the radius $R_p$ of the pulley 702 for driving the pitch axis 114, the radius $R_y$ of the yaw axis pulley 801, and the radius of the roll axis pulley 1101 may each be as large as possible. It is preferable to select a larger diameter of the pulley within a range in which the arm and the wrist of the medical arm device 100 can be sufficiently downsized.

E. Another Structure (1) of Tip Part

In the endoscope holding structure described in section C described above, the two rerouting pulleys 1107 and 1108 that reroute the roll axis wire 503 between the yaw axis and the roll axis are used (See FIGS. 11 and 12.). Among them, the rerouting pulley 1107 is supported on the side surface of the second connection part 1002 so as to be rotatable around an axis parallel to the roll axis 116, and the reroute 1108 is supported on the side surface of the second connection part

18

Figure 13:
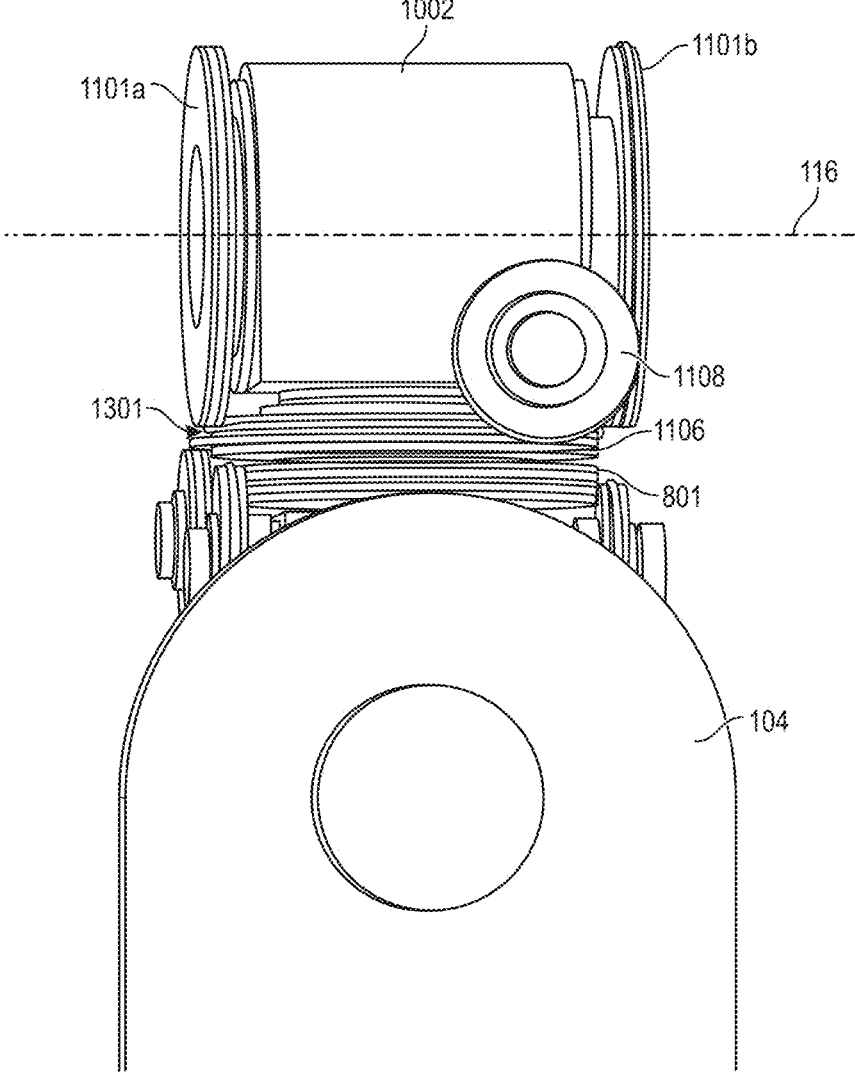
FIG. 13 is a diagram illustrating a structure (second structure) for realizing a rotational degree of freedom around the roll axis 116 in the tip part of the medical arm device 100.
Figure 14:
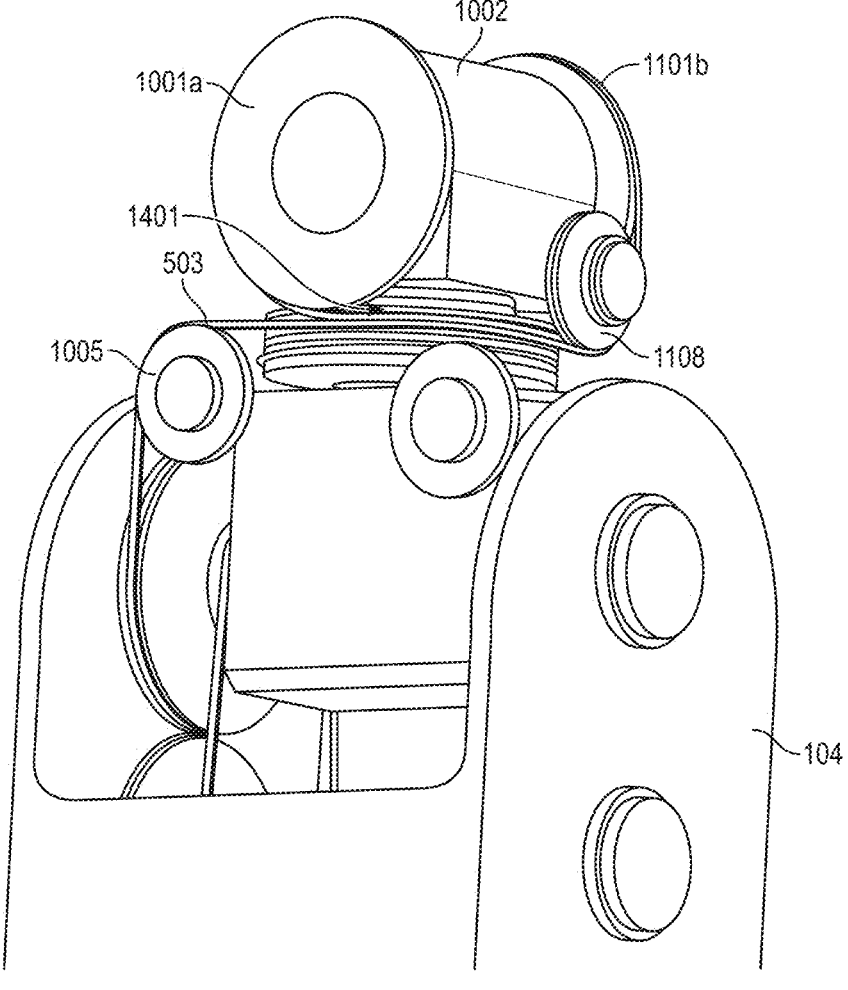
FIG. 14 is a diagram illustrating a structure (second structure) for realizing a rotational degree of freedom around the roll axis 116 in the tip part of the medical arm device 100.

1002 so as to be rotatable around an axis orthogonal to the roll axis 116. On the other hand, in a second endoscope holding structure, the rerouting pulley 1107 is reduced to reduce the number of components and the total length of the wire 503. In FIGS. 13 and 14, a structure for realizing a rotational degree of freedom around the roll axis 116 in the second endoscope holding structure is extracted and illustrated.

As described above, the rerouting pulley 1107 plays a role of rerouting the roll axis wire 503 on the forward path side from the yaw axis direction to the roll axis direction. On the other hand, in the second endoscope holding structure, as illustrated in FIGS. 13 and 14, the path of the roll axis wire 503 is changed from the yaw axis direction to the roll axis direction without using the rerouting pulley 1107 by directly winding the roll axis wire 503 from the two-groove pulley 1106 to the pulley 1101a. In FIGS. 13 and 14, positions where the roll axis wire 503 is passed from the two-groove pulley 1106 to the pulley 1101a are indicated by reference numerals 1301 and 1401, respectively. By shortening a distance between the yaw axis pulley 801 and the roll axis 116, the wire 503 can be directly passed from the two-groove pulley 1106 to the roll axis pulley 1101a, and the rerouting pulley 1107 can be reduced.

In the second endoscope holding structure, there is an advantage that the number of components and the total length of the wire 503 are shortened by the reduction of the pulley 1107. However, since the path is changed from the yaw axis direction to the roll axis direction by directly passing the wire 503 from the two-groove pulley 1106 to the roll axis pulley 1101a, attention should be paid to wear of the wire 503, increased resistance during rotation, and derailment of the wire 503.

Note that, in the second endoscope holding structure illustrated in FIGS. 13 and 14, the same kinematics as that of the endoscope holding structure described in section C described above (See section D described above.) can be applied.

F. Another Structure (2) of Tip Part

Figure 15:
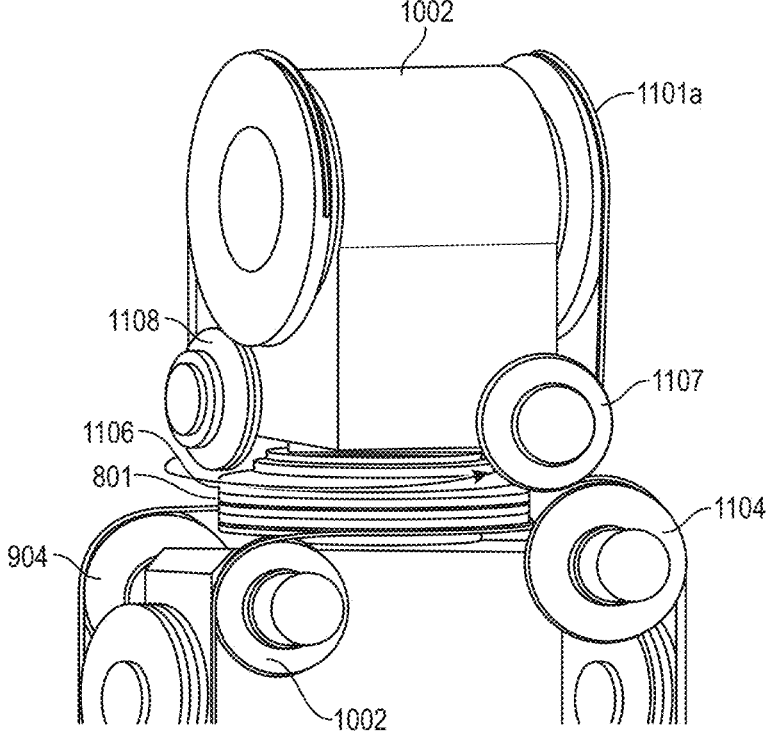
FIG. 15 is a diagram illustrating a state where rerouting pulleys interfere with each other.

In the endoscope holding structure described in section C described above, when the endoscope holding structure rotates around the yaw axis 115, interference occurs between the rerouting pulley 1107 that reroutes from the yaw axis direction to the roll axis direction and the rerouting pulley 1104 that reroutes from the pitch axis direction to the yaw axis direction (See FIG. 15.). Therefore, the rotation movable range on one side around the yaw axis 115 is limited to about 80 deg.

Figure 16:
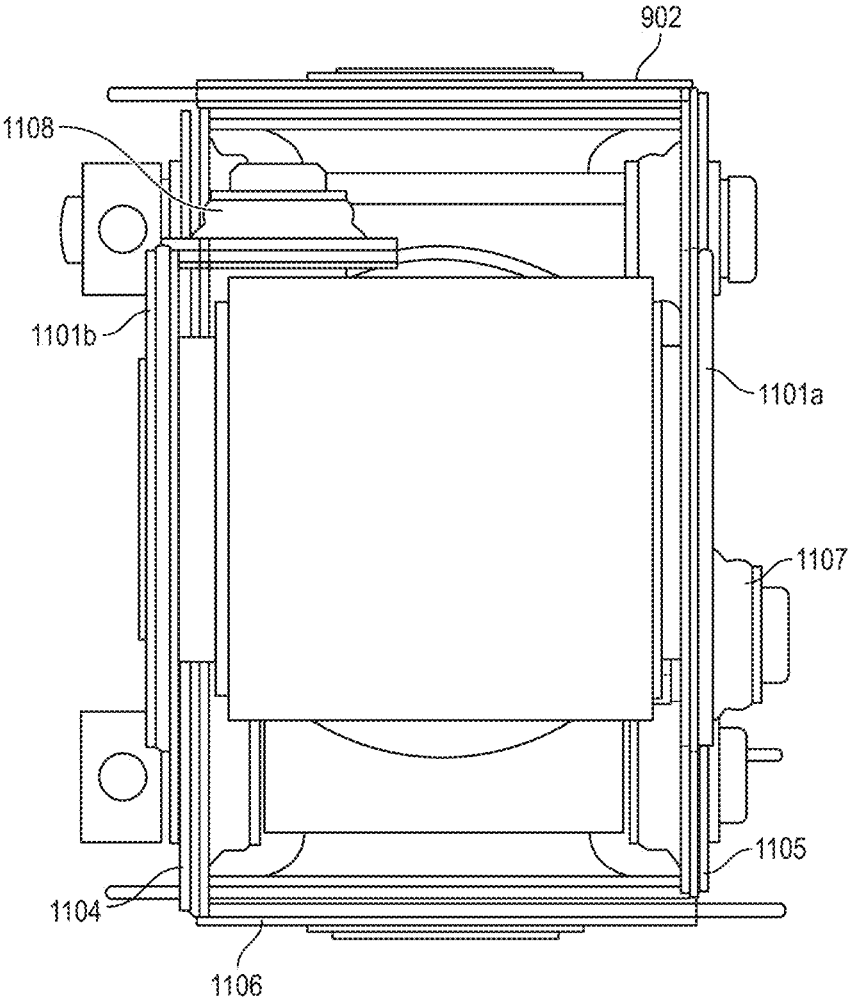
FIG. 16 is a diagram of an endoscope holding structure (the tip part of the medical arm device 100) viewed from above.

The interference between the rerouting pulleys will be described in detail. FIG. 16 illustrates the endoscope holding structure (tip part of the medical arm device 100) described in section C described above as viewed from above. It can be seen from FIG. 16 that the rerouting pulley 1107 that reroutes from the yaw axis direction to the roll axis direction and the rerouting pulley 1108 from the roll axis direction to the yaw axis direction are dispersedly disposed on the side surface of the second connection part 1002 facing the roll direction and the side surface orthogonal thereto. Furthermore, from FIG. 16, the rerouting pulley 1104 that reroutes from the pitch axis direction to the yaw axis direction and the rerouting pulley 1105 that reroutes from the yaw axis direction to the pitch axis direction are supported on the side surface of the pitch axis component 701 so as to be rotatable around a common (or parallel to each other.) axis orthogonal to the pitch axis 114. In such arrangement of each of the rerouting pulleys 1104 to 1108, as described with reference to FIG. 15, when the rotation movable range around the yaw axis 115 is increased, there is a risk that the rerouting pulleys interfere with each other in the vicinity of the yaw axis pulley 801.

Figure 17:
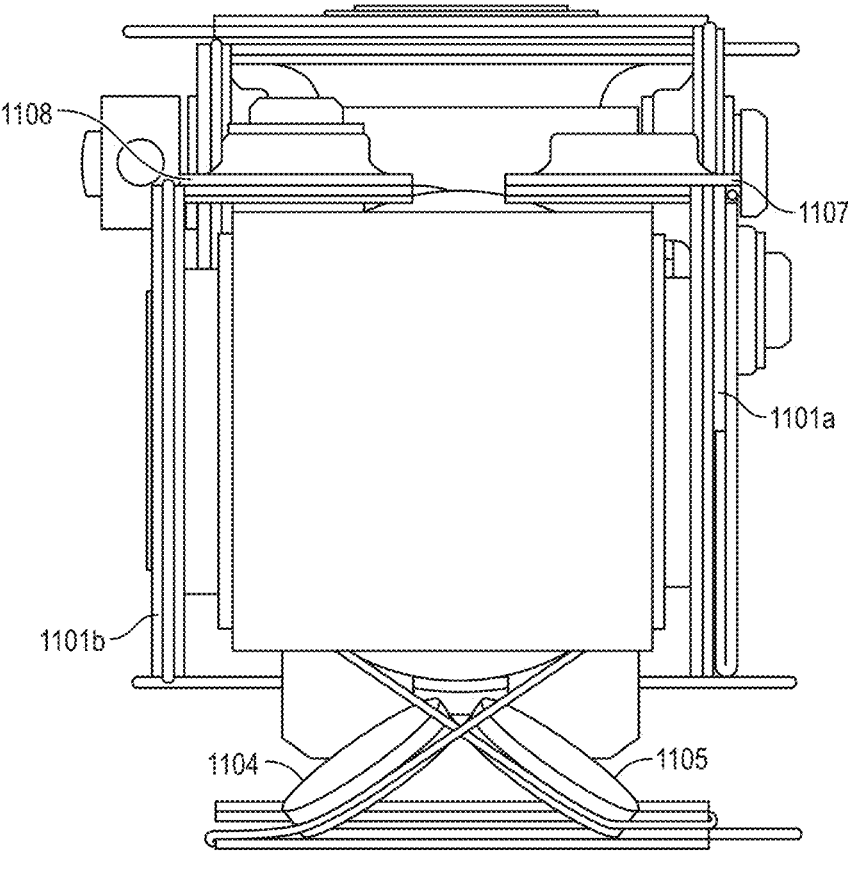
FIG. 17 is a diagram of a third endoscope holding structure (the tip part of the medical arm device 100) as viewed from above.

On the other hand, in a third endoscope holding structure, the two rerouting pulleys 1104 and 1105 for rerouting the wire 503 between the pitch axis and the yaw axis and the two rerouting pulleys 1107 and 1108 for rerouting the wire 503 between the yaw axis and the roll axis are collected and disposed in as narrow ranges as possible, thereby reducing the risk of interference between the rerouting pulleys as much as possible. FIG. 17 illustrates the endoscope holding structure (tip part of the medical arm device 100) described in section C described above as viewed from above.

Specifically, in the third endoscope holding structure, the two rerouting pulleys 1104 and 1105 that reroute the wire 503 between the pitch axis and the yaw axis are disposed such that the rotation axes thereof cross each other, thereby minimizing a region where each of the rerouting pulleys 1104 and 1105 is in contact with the yaw axis pulley 801.

Furthermore, in the third endoscope holding structure, the two rerouting pulleys 1107 and 1108 that reroute the wire 503 between the yaw axis and the roll axis are collectively disposed on the side surface of the second connection part 1002 facing a direction orthogonal to the roll axis 116, so that a region where each of the rerouting pulleys 1107 and 1108 is in contact with the yaw axis pulley 801 is minimized. As can be seen by comparing FIG. 17 with FIG. 16, the rerouting pulley 1107 is disposed to move from the side surface of the second connection part 1002 facing the roll axis 116 to the side surface of the second connection part 1002 facing a direction orthogonal to the roll axis 116.

As described above, by minimizing the regions where each of the rerouting pulleys 1104 and 1105 and the rerouting pulleys 1107 and 1108 is in contact with the yaw axis pulley 801, it is possible to suppress the risk of interference between the rerouting pulleys when the roll axis component greatly rotates around the yaw axis 115.

Figure 18:
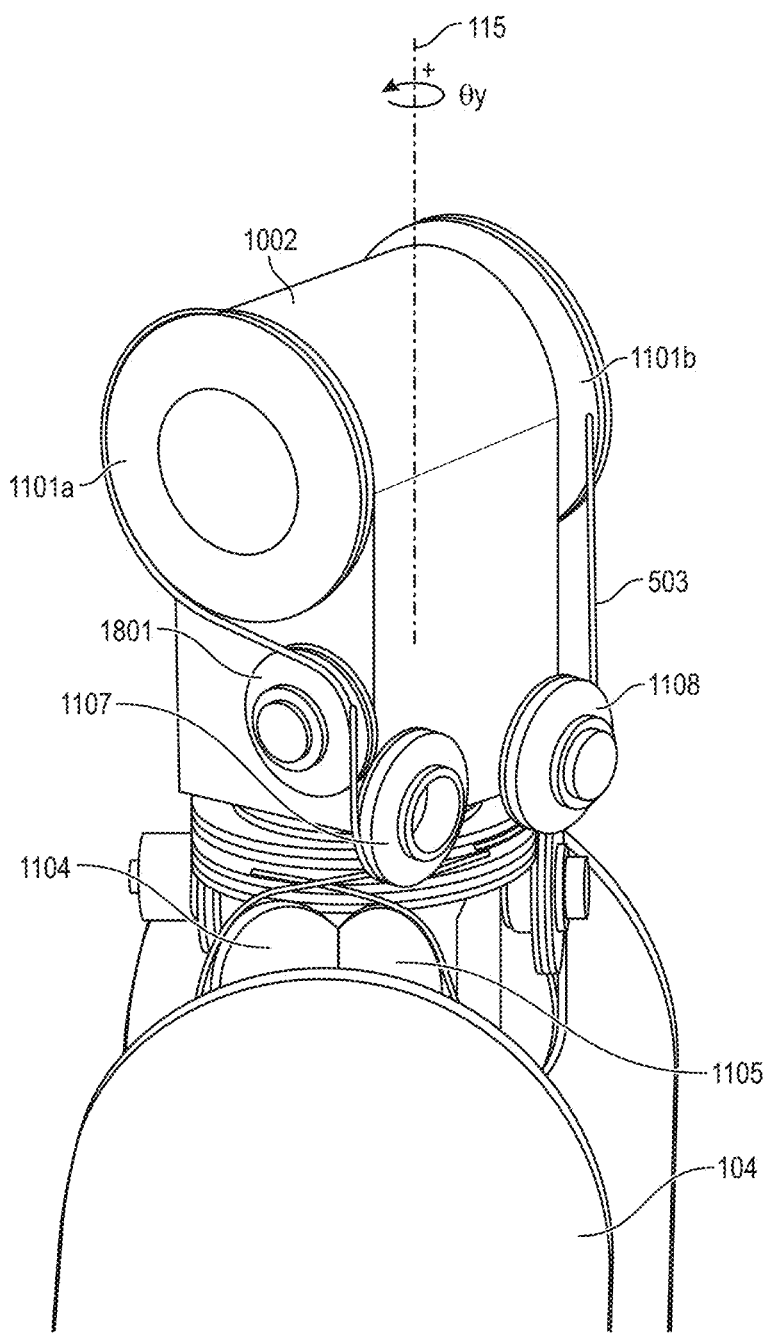
FIG. 18 is a diagram illustrating a state where the third endoscope holding structure is rotated in a positive direction of the yaw axis 115.
Figure 19:
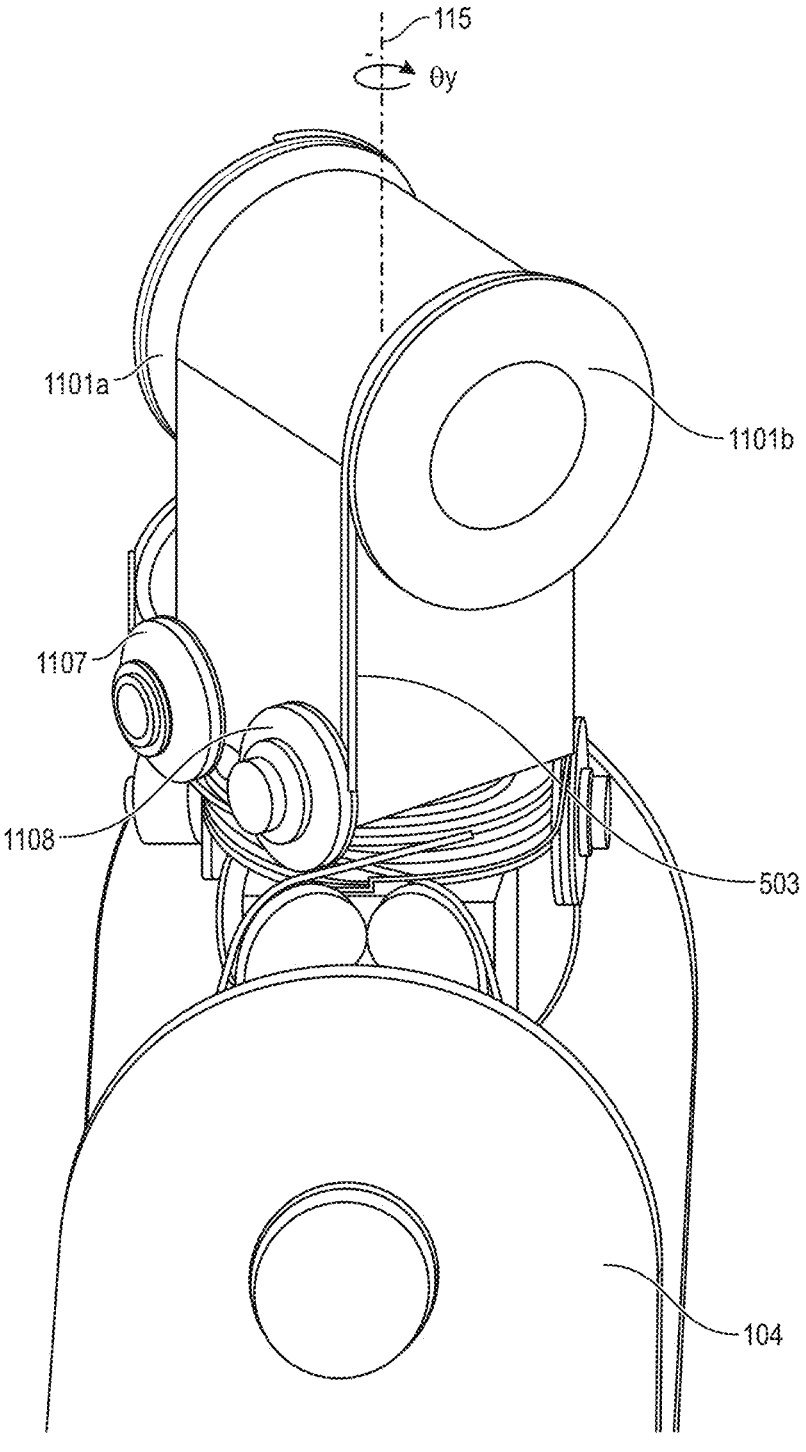
FIG. 19 is a diagram illustrating a state where the third endoscope holding structure is rotated in a negative direction of the yaw axis 115.

FIG. 18 illustrates a state where the third endoscope holding structure is rotated in a positive direction of the yaw axis 115. Furthermore, FIG. 19 illustrates a state where the third endoscope holding structure is rotated in a negative direction of the yaw axis 115. It can be understood from FIGS. 18 and 19 that interference between the rerouting pulleys can be avoided when the rotation is performed around the yaw axis 115. According to the third endoscope holding structure, a rotation movable range of about ±120 deg around the yaw axis 115 can be realized.

Note that, referring to FIG. 18, on the forward path side, the roll axis wire 503 is wound around the two-groove pulley 1106 along the yaw axis, then wound around the rerouting pulley 1107 to change the path from the yaw axis direction to a direction orthogonal to the roll axis, further wound around the rerouting pulley 1801 to change the path from the direction orthogonal to the roll axis to the roll axis direction, and then wound around one pulley 1101*a* of the roll axis pulley 1101. Since the rerouting pulley 1107 is disposed by moving to the side surface of the second connection part 1002 facing the direction orthogonal to the roll axis 116 (described above), the rerouting pulley 1801 for rerouting the wire 503 from the direction orthogonal to the roll axis to the roll axis direction is required. The rerouting pulley 1801 is disposed at a high position on the side surface of the second connection part 1002 so as to avoid interference with the other rerouting pulleys 1104 and 1105 during rotation around the yaw axis 115.

Furthermore, in a case where the roll axis part (the roll axis pulley 1101) is allowed to become slightly larger, or in a case where it is desired to wind the roll axis wire 503 around one of the set of pulleys 1101*a* and 1101*b*, the two rerouting pulleys 1107 and 1108 for changing the route of the wire 503 between the yaw axis and the roll axis may also be disposed such that the rotation axes thereof cross each other (not illustrated).

G. Regarding Increase in Torque

In the endoscope holding structure described above, in a case where a stainless wire rope or the like is used as the wires 501 to 503 for driving each axis, it is possible to generate a torque sufficient to support the endoscope 200 at the tip part of the medical arm device 100.

H. Regarding Load Reduction of Actuator by Weight Reduction of Tip Part

FIG. 6 illustrates that the motors 601 to 603 for each axis are disposed on the root side of the fourth link 104 as close as possible to each other. It is computationally known that a moment can be suppressed to about ⅔ compared to a case where these actuators are disposed at the distal end of the arm, such as the tip side of the fourth link 104. Therefore, the arrangement of the motors 601 to 603 for each axis illustrated in FIG. 6 can reduce the weight of the tip part and reduce the load on the motors 601 to 603 for each axis.

I. Arrangement of Actuators

FIG. 6 illustrates an example in which the pitch axis motor 601, the yaw axis motor 602, and the roll axis motor 603 are disposed in this order from the tip side, but the order of disposing these motors may be changed. However, it is preferable to dispose the heavy motors in this order from the root side (or the proximal end side) because the output required for driving the three degrees of freedom of the tip part can be reduced.

On the other hand, since a high torque is required for driving around the pitch axis 114, as illustrated in FIG. 5, disposing each component such that the pulley group (See, for example, FIGS. 5 and 7.) of the pitch axis wire 501 is located inside the pulley group (See, for example, FIGS. 8 and 9.) for driving around the yaw axis 115 and the pulley group (See, for example, FIGS. 10 and 11.) for driving around the roll axis 116 can contribute to downsizing and high torque.

Furthermore, since the roll axis 116 is used for the optical axis rotation of the endoscope 200 (See FIG. 2.), a small torque is sufficient, and there is no problem in design even if the group of pulleys for driving around the roll axis 116 is disposed on the outermost side.

To sum up, as illustrated in FIG. 6, it can be said that it is ideal to dispose the pitch axis motor 601, the yaw axis motor 602, and the roll axis motor 603 in this order from the tip side.

J. Regarding Two-Groove Pulley Accommodating Pitch Axis Rotation

As described in section C-2 described above, the two-groove pulley 901 is used on a front side (proximal end side) of the pitch axis 114 in order to make the yaw axis wire 502 accommodate the rotation around the pitch axis 114. Furthermore, as described in section C-3 described above, the two-groove pulley 1102 is used on the front side (proximal end side) of the pitch axis 114 in order to make the roll axis wire 503 accommodate the rotation around the pitch axis 114.

Both of these two two-groove pulleys 901 and 1102 are supported by the shaft 704 parallel to the pitch axis 114. The two-groove pulleys 901 and 1102 accommodating the pitch axis rotation are preferably close to the two-groove pulleys 902 and 1103 coaxial with the pitch axis, respectively, but may be slightly separated from each other. In the examples illustrated in FIGS. 7, 9, and 11, the two-groove pulleys 901 and 1102 accommodating the pitch axis rotation are disposed close to the two-groove pulleys 902 and 1103 coaxial with the pitch axis, respectively.

These two-groove pulleys 901 and 1102 for accommodating the pitch axis rotation may not be of the same diameter.

In the embodiment illustrated in FIGS. 4 to 12, the two-groove pulleys 901 and 1102 for accommodating the pitch axis rotation are both rotatably supported by the shaft 702 that is coaxial with the pitch axis 114, but may also be supported by shafts that are different from each other. Furthermore, the shaft supporting the two-groove pulley 901 and the shaft supporting the two-groove pulley 1102 may not have the identical axis. In a case where the shaft supporting the two-groove pulley 901 and the shaft supporting the two-groove pulley 1102 are separated, there is an advantage that the layout of the wiring to the tip is easily designed.

K. Regarding Two-Groove Pulley Coaxial with Pitch Axis

As described in section C-2 described above, the two-groove pulley 902 is used to change the path of the yaw axis wire 502 along the pitch axis 114. Furthermore, as described in section C-3 described above, the two-groove pulley 1103 is used to change the path of the roll axis wire 503 along the pitch axis 114. Both of these two two-groove pulleys 902 and 1103 are supported by the shaft 703 coaxial with the pitch axis 114.

These two-groove pulleys 902 and 1103 for accommodating the pitch axis rotation may not be of the same diameter. Furthermore, none of these two-groove pulleys 902 and 1103 for accommodating the pitch axis rotation may have the same diameter as the pulley 702 for driving the pitch axis.

Note that the pulley is generally a component with two flanges and a groove drilled between the two flanges along an outer periphery of a disk, and is used for transmission of a tensile force by a wire and change of a path (direction of force) of the wire by being hooked on the groove of the outer periphery of the disk so as not to deviate from a flexible string like a wire. Furthermore, the two-groove pulley is a pulley provided with two grooves on the outer periphery of the disk, but may be configured by coaxially integrating pulleys of one groove.

L. Regarding Pulley for Driving Roll Axis

Referring to FIG. 5 and the like, the forward path and the backward path of the roll axis wire 503 are respectively wound around the set of pulleys 1101a and 1101b rotatably attached around the roll axis 116 at both ends of the structure body 1101 including a hollow cylinder. As a modification example thereof, a two-groove pulley may be attached to one side of the hollow cylindrical structure body 1101, and the forward path and the backward path of the roll axis wire 503 may be wound around each groove of the two-groove pulley.

M. Regarding Maximization of Yaw Axis Driving Pulley

The yaw axis 115 corresponds to a pan axis that changes the observation direction of the endoscope 200 (described above). In order to improve the driving torque around the yaw axis 115 (increase the torque), it is preferable to maximize a diameter of the yaw axis pulley 801 while keeping the entire structure from the arm to the wrist thin (Specifically, a dimension of the fourth link 104 is not increased.).

Figure 20:
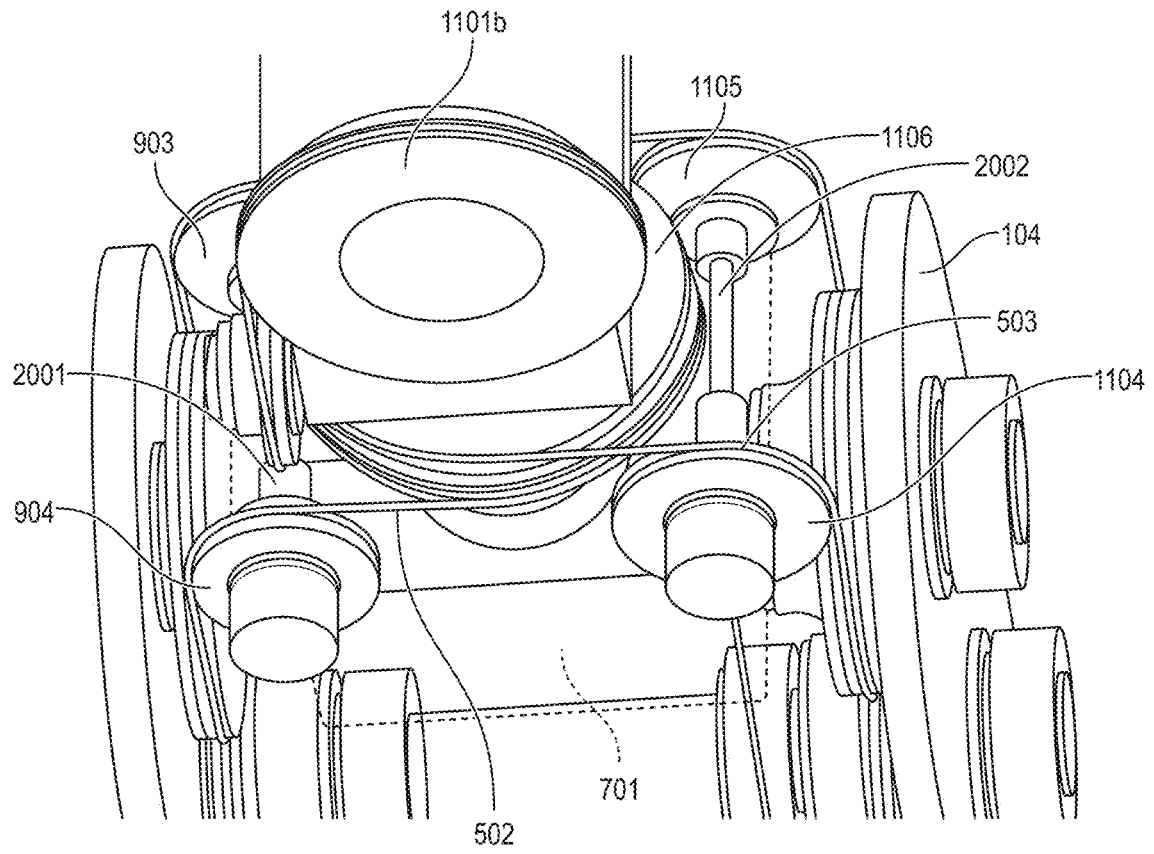
FIG. 20 is a diagram illustrating a structure for realizing a rotational degree of freedom around the yaw axis 115 in the tip part of the medical arm device 100.

FIG. 20 illustrates an enlarged structure for realizing the rotational degree of freedom around the yaw axis 115 in the tip part of the medical arm device 100. The yaw axis pulley 801 is supported on a tip surface of the pitch axis component 701 so as to be rotatable coaxially with the yaw axis 115. Furthermore, the two-groove pulley 1106 and the yaw axis pulley 801 are supported on the tip surface of the pitch axis component 701 so as to be rotatable coaxially with the yaw axis 115.

On the other hand, a pair of the rerouting pulleys 903 and 904 for rerouting the pitch axis wire 501 between the yaw axis and the pitch axis is supported on the side surface of the pitch axis component 701. The two rerouting pulleys 903 and 904 having different diameters are disposed on the identical axis in order to smoothly reroute the yaw axis wire 502 and wind the yaw axis wire around the yaw axis pulley 801 compatible with the two-groove pulley 902 rotating around the pitch axis 114. As illustrated in FIG. 20, the two rerouting pulleys 903 and 904 are rotatably supported by a shaft 2001 constituting the identical axis.

Furthermore, a pair of the rerouting pulleys 1104 and 1105 for rerouting the roll axis wire 503 between the yaw axis and the pitch axis are supported on side surfaces on an opposite side of the pitch axis component 701. Similarly, the two rerouting pulleys 1104 and 1105 having different diameters are disposed on the identical axis in order to smoothly reroute the roll axis wire 503 and wind the wire around the two-groove pulley 1106 which is compatible with the two-groove pulley 1103 rotating around the pitch axis 114. As illustrated in FIG. 20, the two rerouting pulleys 1104 and 1105 are rotatably supported by a shaft 2002 constituting the identical axis.

In a case where a diameter of the yaw axis pulley 801 is increased while the entire structure from the arm to the wrist is kept small, the shaft 2001 or the shaft 2002 may interfere with the yaw axis pulley 801 near the center. Therefore, as illustrated in FIG. 20, the diameter of the yaw axis pulley 801 may be maximized by forming the central parts of the shaft 2001 and the shaft 2002 to be thin or forming the central parts to have a D-cut structure.

N. Effects of Endoscope Holding Structure

In this section N, effects brought by the endoscope holding structure and the wire driving method according to the present disclosure will be summarized.

(1) The medical arm device according to the present disclosure includes an actively drivable three-degree-of-freedom wrist joint having a high torque enough to hold an endoscope.

(2) According to the present disclosure, the tip part having the active joint of three degrees of freedom can have a small and lightweight structure. Therefore, the medical arm device that supports the endoscope at the tip part can access a free space at the hand of the surgeon from an opposite side of the surgeon across the patient (or the operating bed) while avoiding interference with the hands and arms of the surgeon.

(3) According to the present disclosure, the tip part having the active joint of three degrees of freedom can have a small and lightweight structure. Therefore, the load of the actuator that drives each active joint can be reduced, and the weight, cost, and power consumption of the entire device can be reduced.

(4) According to the present disclosure, since each active joint of the tip part with three degrees of freedom can be driven by the wire driving method, backlash or the like does not occur. Therefore, the medical arm device that supports the endoscope at the tip part can determine the position and attitude of the endoscope and the optical axis rotation with high accuracy.

(5) According to the present disclosure, it is possible to have a wide rotation movable range around each rotation axis of the tip part with three degrees of freedom. In particular, as described in section F described above (See FIGS. 18 and 19.), the interference between the rerouting pulleys is avoided by the arrangement of the rerouting pulleys, so that the rotation movable range around the yaw axis can be expanded.

(6) According to the present disclosure, since the actuators that drive the active joints of the tip part with three degrees of freedom can be disposed, for example, on the root side (or proximal end side) of the fourth link 104 in a concentrated manner, the brakes of the actuators can also be easily disposed. Furthermore, wiring for the actuator, the encoders, and the brakes may be up to the root side of the fourth link 104. Therefore, wiring to the tip part can be reduced, and control disturbance can be reduced.

O. Regarding Actuator Arrangement

Figure 21:
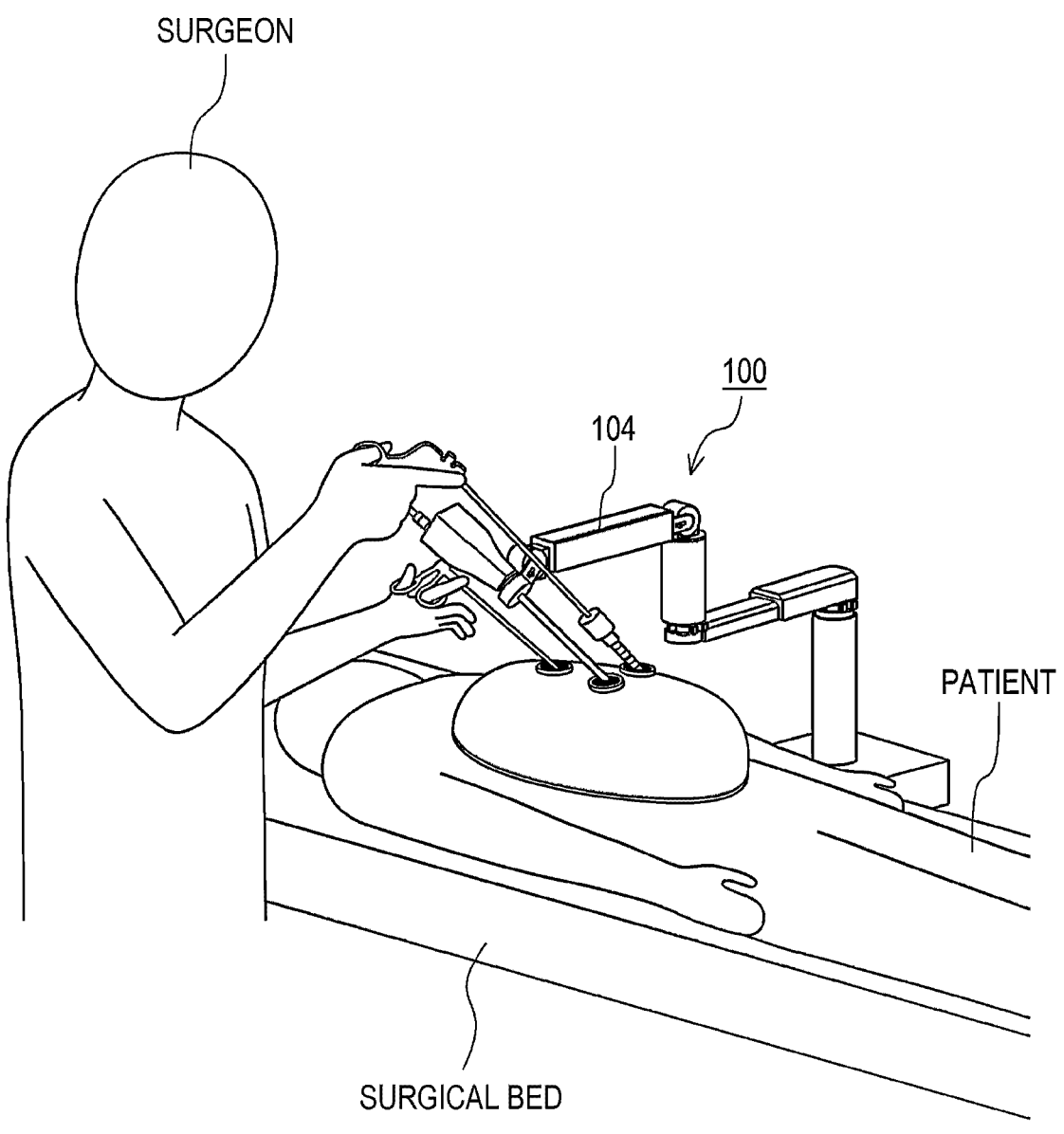
FIG. 21 is a diagram illustrating an example of a surgical procedure of the medical arm device 100.

FIG. 21 illustrates an example of how the medical arm device 100 illustrated in FIG. 1 corresponds to a surgical procedure. In the example illustrated in FIG. 21, the medical arm device 100 is installed on an opposite side of the surgeon across a surgical bed. Then, the surgeon performs laparoscopic surgery on a patient on the surgical bed while observing the state of a surgical site in an abdominal cavity observed using an endoscope (not illustrated) held at the tip of the medical arm device 100.

As described above, in the medical arm device 100 to which the present disclosure is applied, the tip part can realize a small and lightweight structure by intensively disposing orthogonal rotation axes of three degrees of freedom that determine the attitude of the endoscope, and can avoid interference with the surgeon's hand or arm. However, referring to FIG. 21, not only the tip part with three degrees of freedom but also the fourth link 104 supporting the tip part is in an interference region with the surgeon's hand or arm. Therefore, it can be said that it is desirable to design the fourth link 104 with a reduced diameter in order to avoid collision with the surgeon's hand or arm.

FIG. 4 illustrates an example in which the components of the roll axis 116, the yaw axis 115, and the pitch axis 114 are disposed at the tip of the fourth link 104. Furthermore, FIG. 5 illustrates the structures of the pitch axis wire 501, the yaw axis wire 502, and the roll axis wire 503 that tow the components of the pitch axis 114, the yaw axis 115, and the roll axis 116, respectively. FIG. 6 illustrates an example in which the pitch axis motor 601, the yaw axis motor 602, and the roll axis motor 603 are disposed at the root of the fourth link 104.

Figure 22:
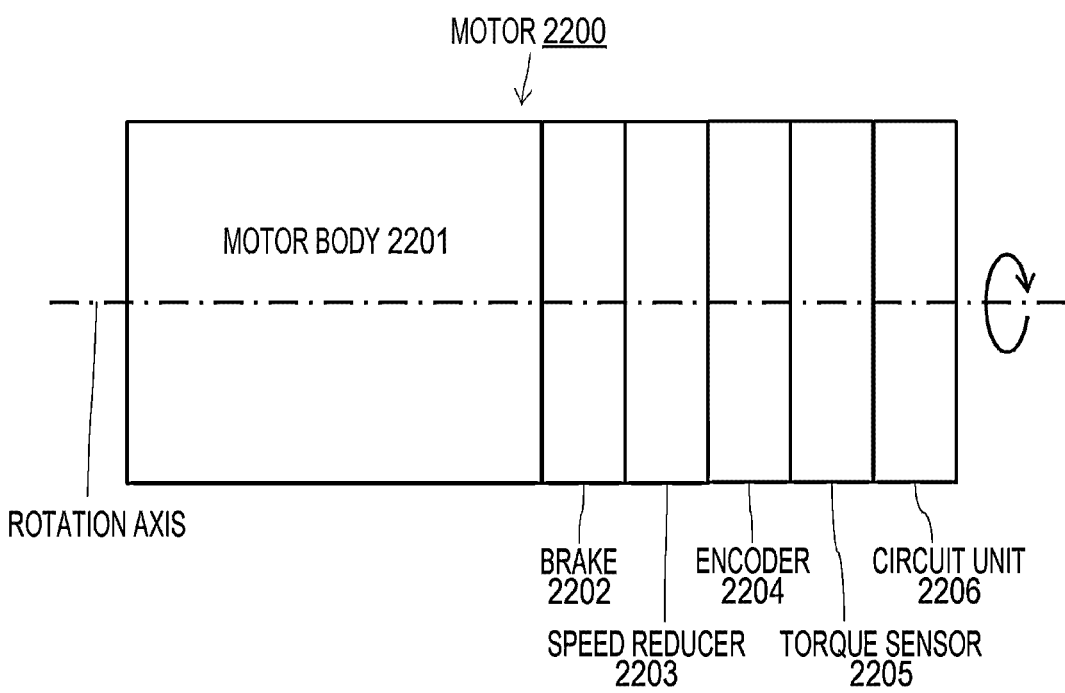
FIG. 22 is a diagram illustrating an appearance configuration of a motor 2200.

Here, FIG. 22 schematically illustrates an appearance configuration of a motor 2200 used for the pitch axis motor 601, the yaw axis motor 602, and the roll axis motor 603. However, the motors 601 to 603 are all assumed to be cylindrical electromagnetic actuators. In general, on an output axis of a rotary motor body 2201, a brake 2202, a speed reducer 2203, an encoder 2204 for detecting a rotational position, a torque sensor 2205 for detecting an external force acting on the output axis, and a circuit unit 2206 are disposed. The brake 2202, the speed reducer 2203, the encoder 2204, and the torque sensor 2205 basically need to be attached in an output axis direction of the motor body 2201, and a dimension in the output axis direction of the entire motor 2200 is expanded. Therefore, the rotary motor 2200 has a cylindrical shape having a small diameter and long in the output axis direction. Note that the circuit unit 2206 includes a printed wired board (PWB) on which a circuit chip that performs signal processing of a sensor signal and a drive signal and the like is mounted, but an arrangement position is not particularly limited. As illustrated in FIG. 22, in a case where the circuit unit 2206 is also disposed in the output axis direction of the motor body 2201, an outer shape of the motor 2200 further expands in the output axis direction while maintaining the small diameter.

FIG. 6 illustrates an example in which the pitch axis motor 601, the yaw axis motor, and the roll axis motor 603 that drive the tip part are disposed on the root side of the fourth link 104 so that the output axes are all parallel to the pitch axis 114, in other words, aligned in a direction orthogonal to the longitudinal direction of the fourth link 104. In such an arrangement of the motors 601 to 603, since a thickness of the fourth link 104 is larger than or equal to a dimension in an output axis direction of the motors 601 to 603, it is difficult to realize the reduction in diameter of the fourth link.

Therefore, in this section O, an actuator arrangement method is proposed in which at least one of the pitch axis motor 601, the yaw axis motor, or the roll axis motor 603 that drive the tip part is disposed with the output axis direction aligned with the longitudinal direction of the fourth link 104, thereby realizing the reduction in diameter of the fourth link 104.

Note that the encoder 2204 used for the motor 2200 is assumed to be an absolute encoder. Furthermore, in a case where the motor 2200 is used for a roll axis, the method of deriving the rotation number from the measurement value of the one-rotation absolute encoder for the output axis (See the section D described above.) is adopted.

O-1. Arrangement Example (1) of Actuators

Figure 23:
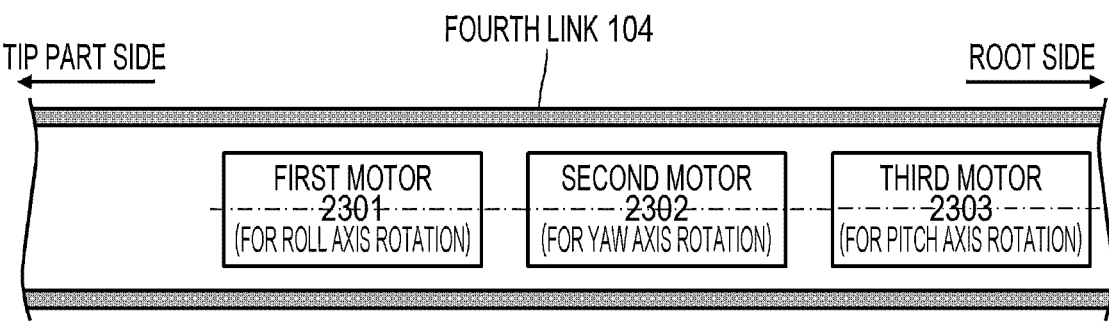
FIG. 23 is a diagram illustrating an arrangement example (1) of each motor that drives each rotation mechanism of the arm tip part.

FIG. 23 illustrates an example in which all three motors 2301 to 2303 that drive the respective rotation mechanisms of the tip part having the three rotation mechanisms are disposed with the output axis direction aligned with the longitudinal direction of the fourth link 104. As illustrated in FIG. 23, the fourth link 104 has a hollow cylindrical shape. Then, the first motor 2301, the second motor 2302, and the third motor 2303 are disposed in this order in the hollow cylinder of the fourth link 104 from a tip part side toward a root side. However, it is assumed that all of the three motors 2301 to 2303 are electromagnetic actuators configured in a cylindrical shape elongated in the output axis direction as illustrated in FIG. 22.

As already described with reference to FIG. 4, the tip part includes the vertical rotation axis (pitch axis) part 114 that swings the endoscope 200 in the vertical direction, the left-right rotation axis (yaw axis) part 115 that is adjacent to the vertical rotation axis part 114, has a degree of freedom around the left-right rotation axis orthogonal to the vertical rotation axis, and swings the endoscope 200 in the left-right direction, and the optical axis rotation axis (roll axis) part 116 having a degree of freedom around the optical axis of the endoscope 200. Which axial rotational drive the first motor 2301, the second motor 2302, and the third motor 2303 are used is arbitrary. However, in order to reduce the moment of inertia around the joint axis of the third joint part 113 of the fourth link 104 and reduce an output of the actuator for driving the third joint part 113, it is preferable to dispose the motors in order of weight from the tip part side toward the root side.

Although it is possible to drive the endoscope 200 around the roll axis with low torque only by the rotation of the optical axis, high torque is required around the pitch axis in order to drive the entire tip part. Then, assuming that a relationship in which an output of the motor is substantially proportional to a weight of the motor (That is, the weight of the motor increases as the output of the motor increases.) is established, it is considered preferable to assign the motors in which the first motor 2301 performs the rotational drive around the roll axis 116 of the lens barrel 201, the second motor 2302 performs the rotational drive around the yaw axis 115 of the endoscope 200, and the third motor 2303 performs the rotational drive around the pitch axis 114 of the entire tip part.

Note that, since the structure of the tip part is as described in section C described above, the tip part is not illustrated in FIG. 23. Furthermore, in FIG. 23, for simplification of the drawing, illustration of a wire transmission mechanism including a wire for transmitting the rotation of each of the motors 2301 to 2303 to the tip part side and a pulley for changing the path of the wire and the like is also omitted. By using the wire transmission mechanism for transmitting the rotational force, there is an advantage that the driving force of the actuator can be transmitted with high efficiency and with high accuracy while suppressing the occurrence of backlash. Since the load torque of each rotation mechanism of three degrees of freedom of the tip part is relatively small, it is possible to cover low strength which is a disadvantage of the wire transmission mechanism. Furthermore, it is possible to maximally utilize small and lightweight drive transmission which is an advantage of the wire transmission mechanism. Since each of the motors 2301 to 2303 is disposed on the root side of the fourth link 104 while being separated from the actual joint position of the tip part, the tip part is reduced in weight, and the torque required to drive each joint can be reduced, which contributes to downsizing of the entire medical arm device 100.

O-2. Arrangement Example (2) of Actuators

FIGS. 24 and 25 illustrate an example in which, out of three motors 2401 to 2403 that drive the respective rotation mechanisms of the tip part having the three rotation mechanisms, the first motor 2401 and the second motor 2402 are disposed with the output axis direction aligned with the longitudinal direction of the fourth link 104, and the third motor 2403 on the root side is disposed with the output axis direction oriented in a direction orthogonal to the longitudinal direction of the fourth link 104. FIG. 24 illustrates a state viewed from a direction of a side surface of the third motor 2403, and FIG. 25 illustrates a state viewed from a direction of a rotation axis of the third motor 2403. However, all of the three motors 2401 to 2403 are cylindrical electromagnetic actuators elongated in the output axis direction as illustrated in FIG. 22.

According to the actuator arrangement example illustrated in FIGS. 24 and 25, a length of a section in which third motor 2403 is disposed is shortened to around a diameter of the motor 2403. That is, a link length of the fourth link 104 can be shortened. However, in the arrangement example of the actuators illustrated in FIG. 24, a diameter of a section in which the first motor 2401 and the second motor 2402 are disposed in the fourth link 104 can be reduced, but the diameter of the section in which the third motor 2403 is disposed needs to be increased. In a case where an increase in the diameter of the fourth link 104 is allowed, it is an effective design. On the other hand, in the case of the actuator arrangement example illustrated in FIG. 23, the link length of the fourth link 104 is longer than the sum of the dimensions of the motors 2301 to 2303 in the output axis direction at the shortest. In short, according to the arrangement example of the actuators illustrated in FIGS. 24 and 25, it is possible to balance the reduction in the diameter of the fourth link 104 and the reduction in the link length.

Also in the arrangement example of the actuators illustrated in FIGS. 24 and 25, in order to reduce the inertia moment around the joint axis of the third joint part 113 of the fourth link 104 and reduce the output of the actuator for driving the third joint part 113, it is preferable to dispose the motors in ascending order of weight from the tip part side toward the root side. Specifically, it is considered preferable to assign the motors in which the first motor 2401 performs the rotational drive around the roll axis 116 of the lens barrel 201, the second motor 2402 performs the rotational drive around the yaw axis 115 of the endoscope 200, and the third motor 2403 performs the rotational drive around the pitch axis 114 of the entire tip part.

Note that, since the structure of the tip part is as described in section C described above, illustration of the tip part is omitted in FIGS. 24 and 25. Furthermore, although a wire transmission mechanism is used to transmit the rotation of each of the motors 2401 to 2403 to the tip part side, the wire transmission mechanism is not illustrated in FIGS. 24 and 25 for simplification of the drawings. By using the wire transmission mechanism, it is possible to transmit the rotation of each of the motors 2401 to 2403 with high accuracy by suppressing the occurrence of backlash with high efficiency of the driving force of the actuator. Since the load torque of each rotation mechanism of three degrees of freedom of the tip part is relatively small, it is possible to cover low strength which is a disadvantage of the wire transmission mechanism. Furthermore, it is possible to maximally utilize small and lightweight drive transmission which is an advantage of the wire transmission mechanism. Since each of the motors 2401 to 2403 is disposed on the root side of the fourth link 104 while being separated from the actual joint position of the tip part, the tip part is reduced in weight, and the torque required for the rotational drive of the fourth link 104 can be reduced, which contributes to downsizing of the entire medical arm device 100.

O-3. Arrangement Example (3) of Actuators

FIGS. 26 and 27 illustrate an example in which, among three motors 2601 to 2603 that drive the respective rotation mechanisms at the tip part having the three rotation mechanisms, the motor 2601 is disposed with the output axis direction aligned with the longitudinal direction of the fourth link 104, while the second motor 2602 and the third motor 2603 are disposed with the output axis direction oriented in a direction orthogonal to the longitudinal direction of the fourth link 104. FIG. 26 illustrates a state viewed from a direction of side surfaces of the second motor 2602 and the third motor 2603, and FIG. 27 illustrates a state viewed from a direction of rotation axes of the second motor 2602 and the third motor 2603. However, all of the three motors 2601 to 2603 are cylindrical electromagnetic actuators elongated in the output axis direction as illustrated in FIG. 22.

According to the arrangement example of the actuators illustrated in FIGS. 26 and 27, since a length of a section in which the second motor 2602 and the third motor 2603 are disposed is shortened to about a diameter of each of the motors 2602 and 2603, it is possible to further shorten the link length of the fourth link 104 as compared with the arrangement example of the actuators illustrated in FIGS. 24 and 25 while forming a reduced diameter part of the fourth link 104. In a case where an increase in the diameter of the fourth link 104 is allowed, it is an effective design. In short, according to the arrangement example of the actuators illustrated in FIGS. 26 and 27, it is possible to balance the reduction in the diameter of the fourth link 104 and the reduction in the link length.

Note that, also in the arrangement example of the actuators illustrated in FIGS. 26 and 27, in order to reduce the moment of inertia around the joint axis of the third joint part 113 of the fourth link 104 and reduce the output of the actuator for driving the third joint part 113, it is preferable to dispose the motors in ascending order of weight from the tip part side toward the root side. Specifically, it is considered preferable to assign the motors in which the first motor 2601 performs the rotational drive around the roll axis 116 of the lens barrel 201, the second motor 2602 performs the rotational drive around the yaw axis 115 of the endoscope 200, and the third motor 2603 performs the rotational drive around the pitch axis 114 of the entire tip part.

Note that, since the structure of the tip part is as described in section C described above, illustration of the tip part is omitted in FIGS. 26 and 27. Furthermore, although a wire transmission mechanism is used to transmit the rotation of each of the motors 2601 to 2603 to the tip part side, the wire transmission mechanism is not illustrated in FIGS. 26 and 27 for simplification of the drawings. By using the wire transmission mechanism, it is possible to transmit the rotation of each of the motors 2601 to 2603 with high accuracy by suppressing the occurrence of backlash with high efficiency of the driving force of the actuator. Since the load torque of each rotation mechanism of three degrees of freedom of the tip part is relatively small, it is possible to cover low strength which is a disadvantage of the wire transmission mechanism. Furthermore, it is possible to maximally utilize small and lightweight drive transmission which is an advantage of the wire transmission mechanism. Since each of the motors 2601 to 2603 is disposed on the root side of the fourth link 104 while being separated from the actual joint position of the tip part, the tip part is reduced in weight, and the torque required for the rotational drive of the fourth link 104 can be reduced, which contributes to downsizing of the entire medical arm device 100.

O-4. Arrangement Example (4) of Actuators

FIGS. 28 and 29 illustrate an example in which all three motors 2801 to 2803 that drive the respective rotation mechanisms at the tip part having the three rotation mechanisms are disposed with the output axis direction aligned with the longitudinal direction of the fourth link 104. FIG. 28 illustrates a state viewed from a direction of side surfaces of the motors 2801 to 2803, and FIG. 29 illustrates a state viewed from a direction of rotation axes of the motors 2801 to 2803. However, all of the three motors 2801 to 2803 are cylindrical electromagnetic actuators elongated in the output axis direction as illustrated in FIG. 22.

A difference between the arrangement example of the actuators illustrated in FIGS. 28 and 29 and the arrangement example of the actuators illustrated in FIG. 6 is that a part of a section on the tip part side where the three motors 2801 to 2803 are not disposed in the fourth link 104 is reduced in diameter.

Note that, since the structure of the tip part is as described in section C described above, illustration of the tip part is omitted in FIGS. 28 and 29. Furthermore, although a wire transmission mechanism is used to transmit the rotation of each of the motors 2801 to 2803 to the tip part side, the wire transmission mechanism is not illustrated in FIGS. 28 and 29 for simplification of the drawings.

O-5. Arrangement Example (5) of Actuators

Figure 30:
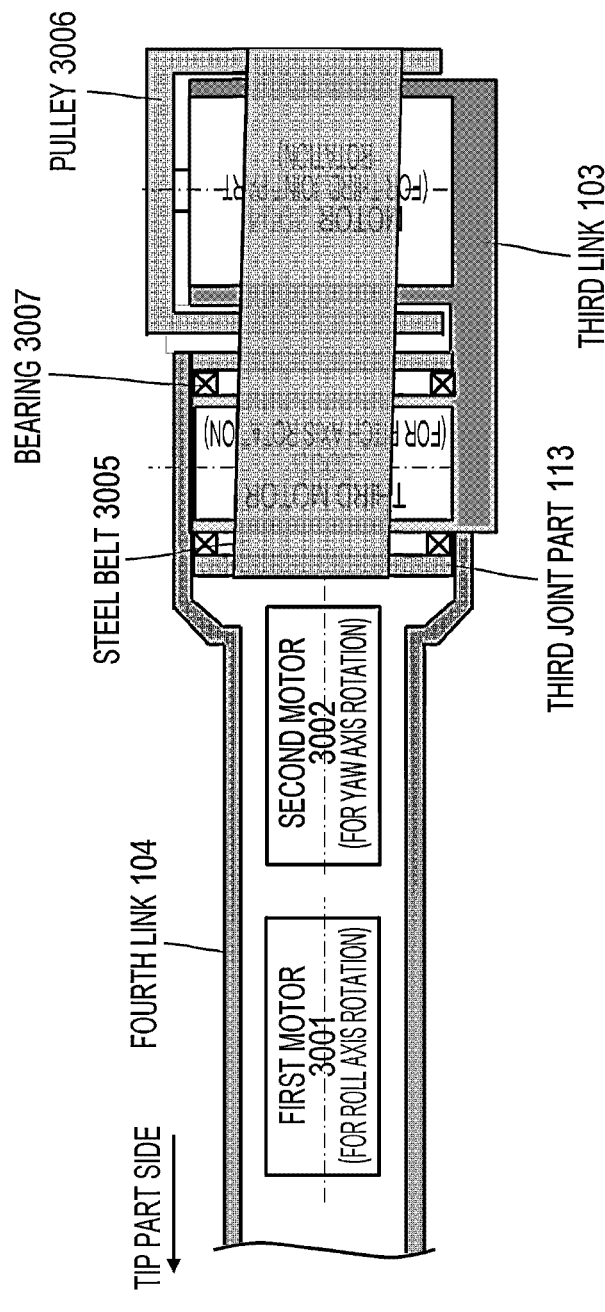
FIG. 30 is a diagram illustrating an arrangement example (5) of each motor that drives each rotation mechanism of the arm tip part.
Figure 31:
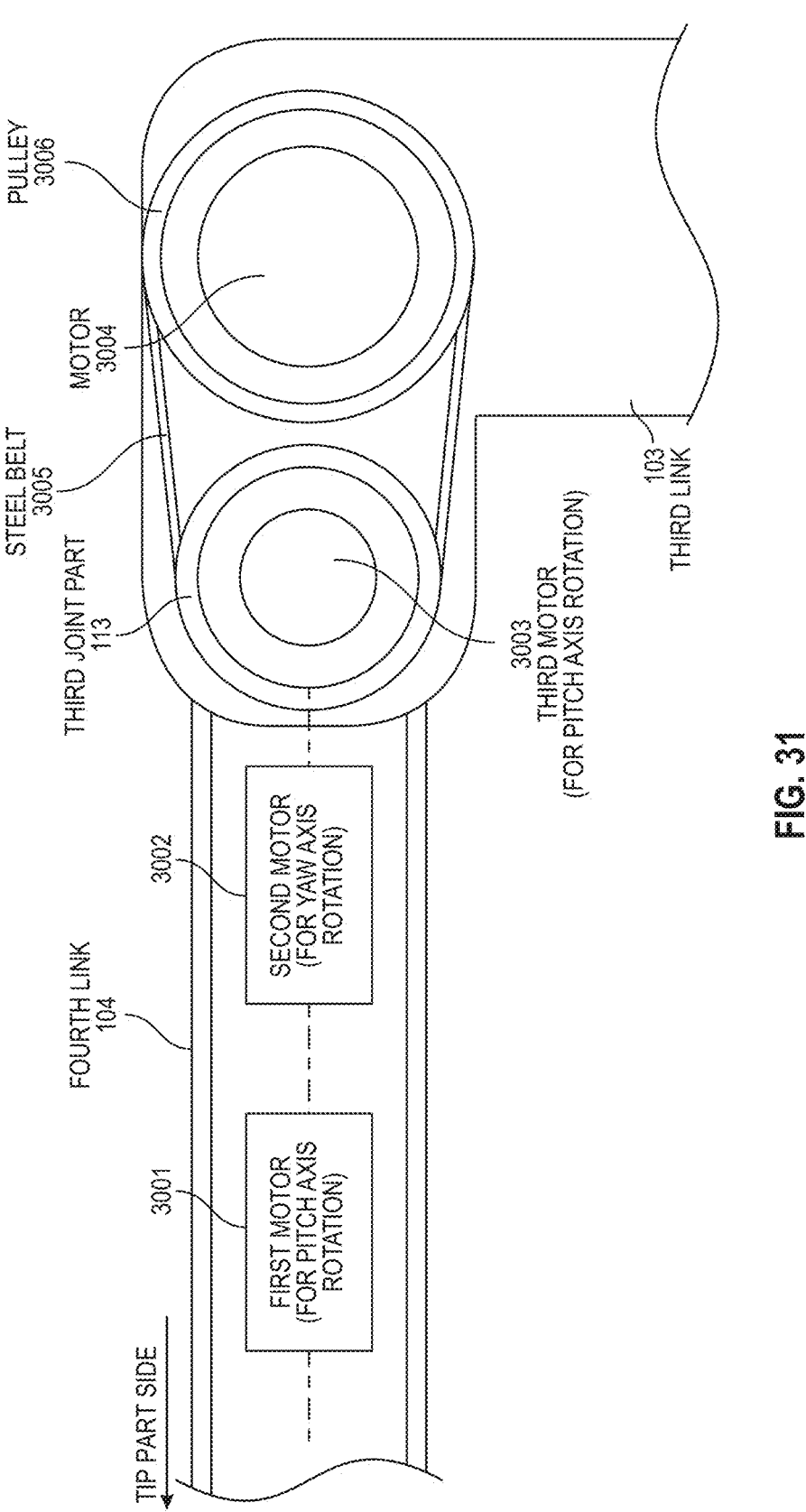
FIG. 31 is a diagram illustrating an arrangement example (5) of each motor that drives each rotation mechanism of the arm tip part.

FIGS. 30 and 31 illustrate an example in which, out of three motors 3001 to 3003 that drive the respective rotation mechanisms at the tip part having the three rotation mechanisms, the first motor 3001 and the second motor 3002 are disposed on the fourth link 104 with the output axis direction aligned with the longitudinal direction of the fourth link 104, while the third motor 3003 is disposed in an outside (on the root side) of the fourth link 104 with the output axis direction oriented in a direction orthogonal to the longitudinal direction of the fourth link 104. FIG. 30 illustrates a state viewed from a direction of a side surface of the third motor 3003, and FIG. 31 illustrates a state viewed from a direction of a rotation axis of the third motor 3003. However, all of the three motors 3001 to 3003 are cylindrical electromagnetic actuators elongated in the output axis direction as illustrated in FIG. 22.

Note that, since the structure of the tip part is as described in section C described above, illustration of the tip part is omitted in FIGS. 30 and 31. Furthermore, although a wire transmission mechanism is used to transmit the rotation of each of the motors 3001 to 3003 to the tip part side, the wire transmission mechanism is not illustrated in FIGS. 30 and 31 for simplification of the drawings.

The arrangement example of the actuators illustrated in FIGS. 30 and 31 is common to the arrangement example of the actuators illustrated in FIGS. 24 and 25 in that the first motor 3001 and the second motor 3002 are disposed with the output axis direction aligned with the longitudinal direction of the fourth link 104, while the third motor 3003 on the root side is disposed with the output axis direction oriented in a direction orthogonal to the longitudinal direction of the fourth link 104. However, the actuator arrangement example illustrated in FIGS. 30 and 31 is different from the example illustrated in FIGS. 24 and 25 in that the third motor 3003 is disposed outside the fourth link 104. In the arrangement example of the actuators illustrated in FIGS. 24 and 25, the third motor 2403 is disposed in the fourth link 104. By disposing the third motor 3003 outside the fourth link 104, compactness of the fourth link 104 can be realized.

Specifically, the third motor 3003 is disposed in a rotation mechanism unit on the root side of the fourth link 104. Here, the rotation mechanism unit on the root side of the fourth link 104 corresponds to the third joint part 113 in FIG. 1. The third joint part 113 is a rotation mechanism that rotates the fourth link 104 around the vertical rotation axis (alternatively, the pitch axis) on the root side. By disposing the third motor 3003 outward from the root side of the fourth link 104, the torque required for the rotational drive of the fourth link 104 is further reduced, which contributes to further downsizing of the entire medical arm device 100.

In a case where the third motor 3003 is disposed in the third joint part 113, a motor 3004 for rotating the fourth link 104 around the pitch axis cannot be disposed in the third joint part 113. Therefore, in the arrangement example of the actuators illustrated in FIGS. 30 and 31, the motor 3004 for driving the third joint part 113 is disposed outside the third joint part 113 (on an opposite side of the fourth link 104). Then, a rotational force of the motor 3004 is transmitted to the third joint part 113 accommodating the third motor 3003 using a steel belt 3005 to realize the rotation of the fourth link 104 around the pitch axis.

Referring to FIGS. 30 and 31, the third joint part 113 has a hollow cylindrical structure having a central axis in the pitch axis direction, and is joined and integrated with an inner wall of the fourth link 104. On the other hand, the third motor 3003 and the motor 3004 are fixed to a frame of the third link 103. The third motor 3003 is disposed in the hollow cylinder of the third joint part 113 such that the rotation axis coincides with a joint axis of the third joint part 113, and is rotatably supported around the joint axis via a bearing.

An output axis pulley 3006 of the motor 3004 includes a hollow cylinder that covers an outer periphery of the motor 3004. Then, the steel belt 3005 is wound around the third joint part 113 and the output axis pulley 3006. Therefore, the rotation of the motor 3004 is transmitted to the third joint axis 113 via the steel belt 3005, and the fourth link 104 can be rotated around the joint axis of the third joint part 113 (around the pitch axis or around the vertical rotation axis). At this time, since the third motor 3003 is rotatably supported in the hollow cylinder of the third joint part 113 via a bearing, the rotational operation of the motor 3004 is not transmitted to the third motor 3003. Furthermore, by using the steel belt 3005 including a metal plate such as stainless steel for the transmission mechanism of the rotation of the motor 3004, it is possible to perform drive transmission with high strength, wide movable range, high efficiency, and high accuracy without rattling.

O-6. Arrangement Example (6) of Actuators

Figure 32:
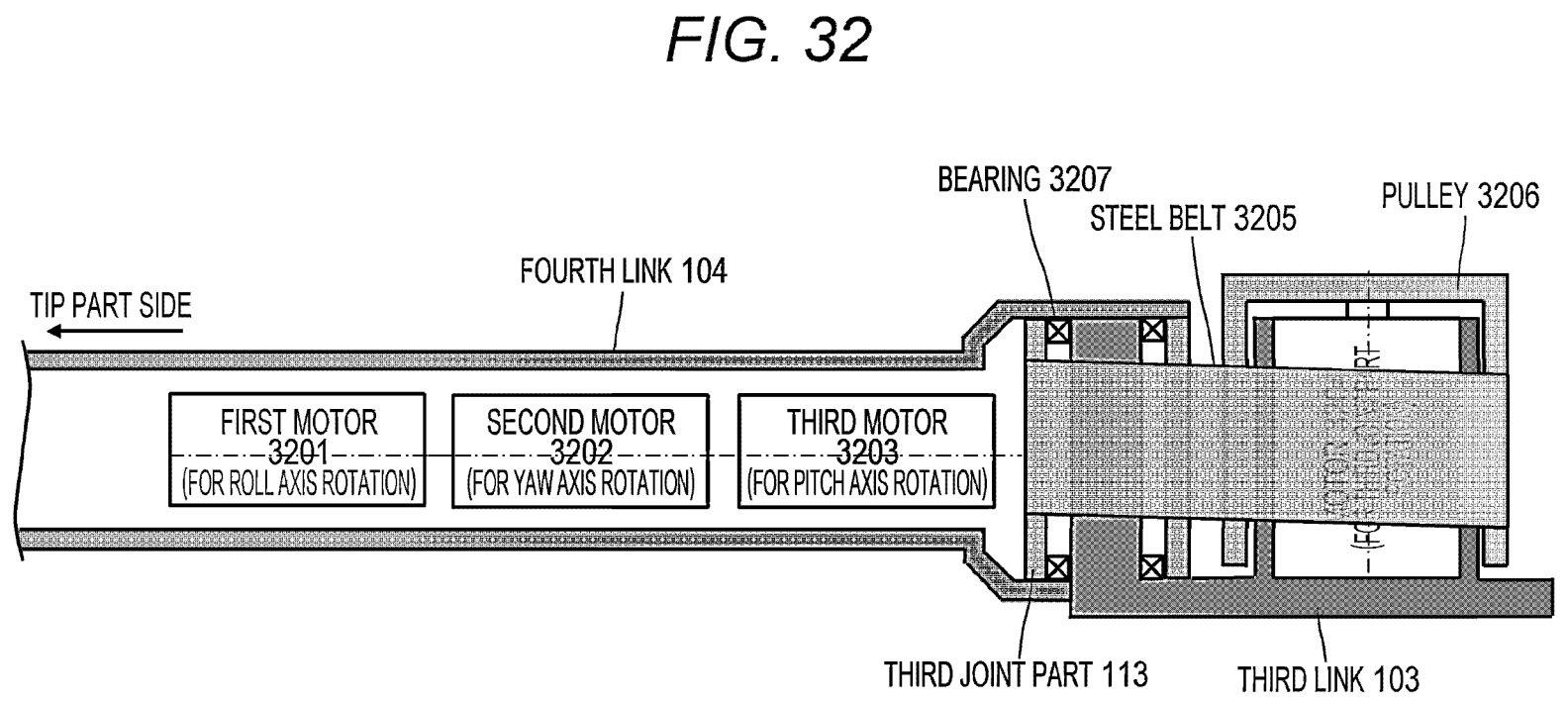
Figure 33:
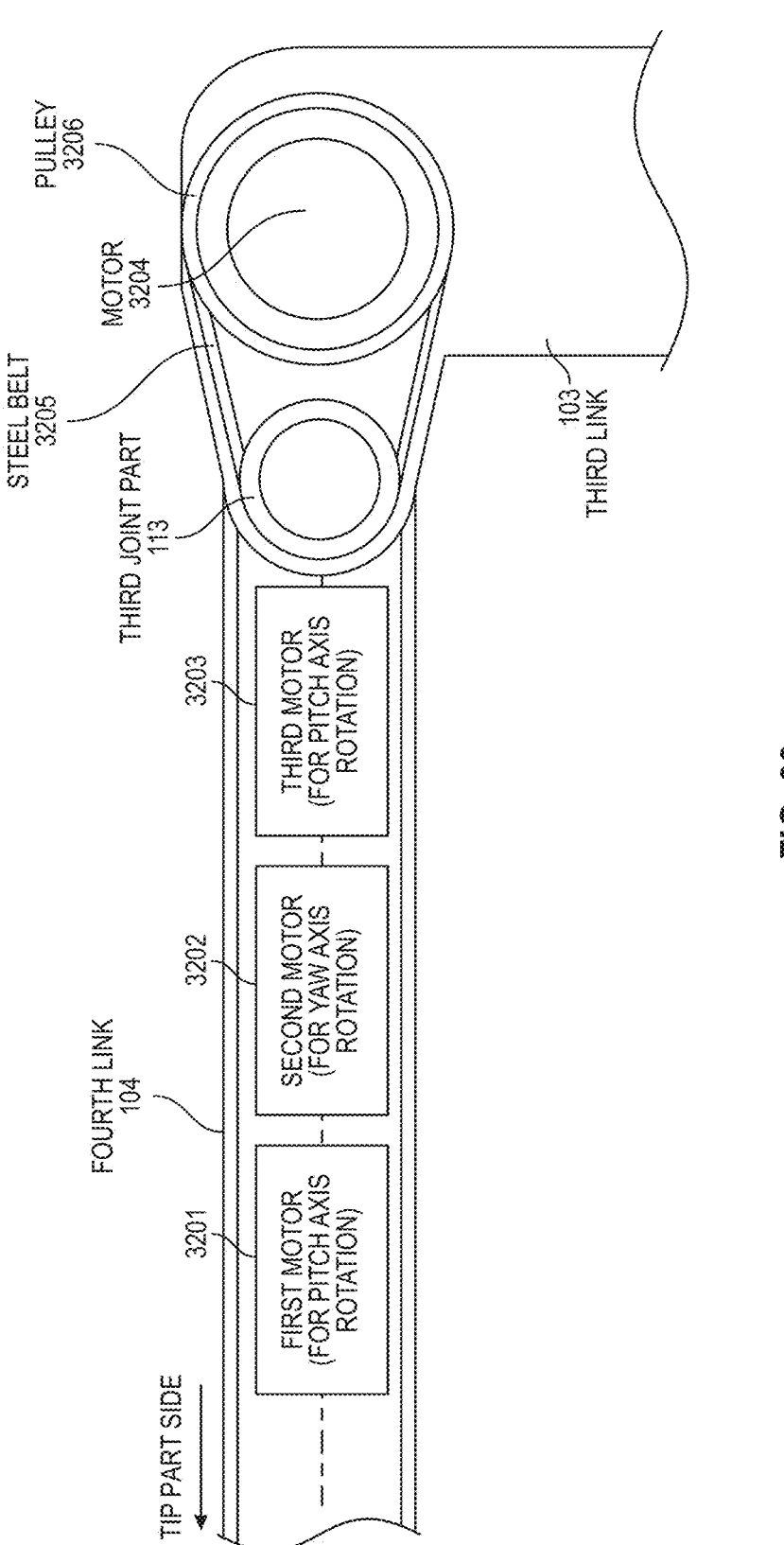
FIG. 33 is a diagram illustrating an arrangement example (6) of each motor that drives each rotation mechanism of the arm tip part.

FIGS. 32 and 33 illustrate an example in which all three motors 3201 to 3203 that drive the respective rotation mechanisms of the tip part having the three rotation mechanisms are disposed on the fourth link 104 with the output axis direction aligned with the longitudinal direction of the fourth link 104, and a motor 3204 for driving the third joint part 113 is disposed outside the third joint part 113 (on an opposite side of the fourth link 104). FIG. 32 illustrates a state viewed from a direction of a side surface of the motor 3204, and FIG. 33 illustrates a state viewed from a direction of a rotation axis of the motor 3204. However, all of the three motors 3201 to 3203 are cylindrical electromagnetic actuators elongated in the output axis direction as illustrated in FIG. 22.

Note that, since the structure of the tip part is as described in section C described above, illustration of the tip part is omitted in FIGS. 32 and 33. Furthermore, although a wire transmission mechanism is used to transmit the rotation of each of the motors 3201 to 3203 to the tip part side, the wire transmission mechanism is not illustrated in FIGS. 32 and 33 for simplification of the drawings.

The arrangement example of the actuators illustrated in FIGS. 32 and 33 is common to the arrangement example of the actuators illustrated in FIGS. 30 and 31 in that the motor 3204 for driving the third joint part 113 is disposed outside the third joint part 113 (on an opposite side of the fourth link 104). However, the arrangement example of the actuators illustrated in FIGS. 32 and 33 is different from the example illustrated in FIGS. 30 and 31 in that the first to third motors 3201 to 3201 are disposed in the fourth link 104 and none of the actuators is disposed in the third joint part 113. In the actuator arrangement example illustrated in FIGS. 32 and 33, the entire fourth link 104 can be reduced in diameter by disposing all the motors 3201 to 3203 on the fourth link 104 with the output axis direction aligned with the longitudinal direction of the fourth link 104. Furthermore, by not disposing any motor in the third joint part 113, the third joint part 113 is downsized, so that a small diameter part of the fourth link 104 can be secured in a long section.

The third joint part 113 is a rotation mechanism that rotates the fourth link 104 around the vertical rotation axis (alternatively, the pitch axis) on the root side (described above). Referring to FIGS. 32 and 33, the third joint part 113 has a hollow cylindrical structure having a central axis in the pitch axis direction, and is joined and integrated with an inner wall of the fourth link 104. Furthermore, the third joint part 113 is supported by the third link 103 via a bearing disposed in the hollow cylinder so as to be rotatable around the joint axis.

An output axis pulley 3206 of the motor 3204 includes a hollow cylinder that covers an outer periphery of the motor 3204. Then, a steel belt 3205 is wound around the third joint part 113 and the output axis pulley 3206. Therefore, the rotation of the motor 3204 is transmitted to the third joint axis 113 via the steel belt 3205, and the fourth link 104 can be rotated around the joint axis of the third joint part 113 (around the pitch axis or around the vertical rotation axis). Furthermore, by using the steel belt 3205 including a metal plate such as stainless steel for the transmission mechanism of the rotation of the motor 3204, it is possible to perform drive transmission with high strength, wide movable range, high efficiency, and high accuracy without rattling.

O-7. Arrangement of Wire Transmission Mechanism

As described in sections O-1 to O-6 described above, in a case where the motors for each axis are disposed on the root side of the fourth link 104 apart from the roll axis, the yaw axis, and the peach axis of the tip part, a transmission mechanism for transmitting a rotational force of each of the motors to the tip part is required. In the present disclosure, by using a wire transmission mechanism for transmitting the rotational force, a driving force of the actuator is transmitted with high efficiency and with high accuracy while suppressing the occurrence of backlash. Since the load torque of each rotation mechanism of three degrees of freedom of the tip part is relatively small, it is possible to cover low strength which is a disadvantage of the wire transmission mechanism. Furthermore, it is possible to maximally utilize small and lightweight drive transmission which is an advantage of the wire transmission mechanism.

In this section O-7, an arrangement example of a wire drive mechanism that transmits the rotational force of each of the motors to the tip part in the fourth link 104 in the arrangements of each of the motors described in sections O-1 to O-6 described above will be described. Basically, a rotational force of the motor is extracted using a wire wound around the output axis pulley attached to an output axis of the motor. Then, the position and direction of the pitch axis or the roll axis of the wire are changed appropriately using the rerouting pulley to avoid interference with other motors and other components existing between the output axis pulley and the tip part, and the motor and the target component are connected by the wire.

Figure 34:
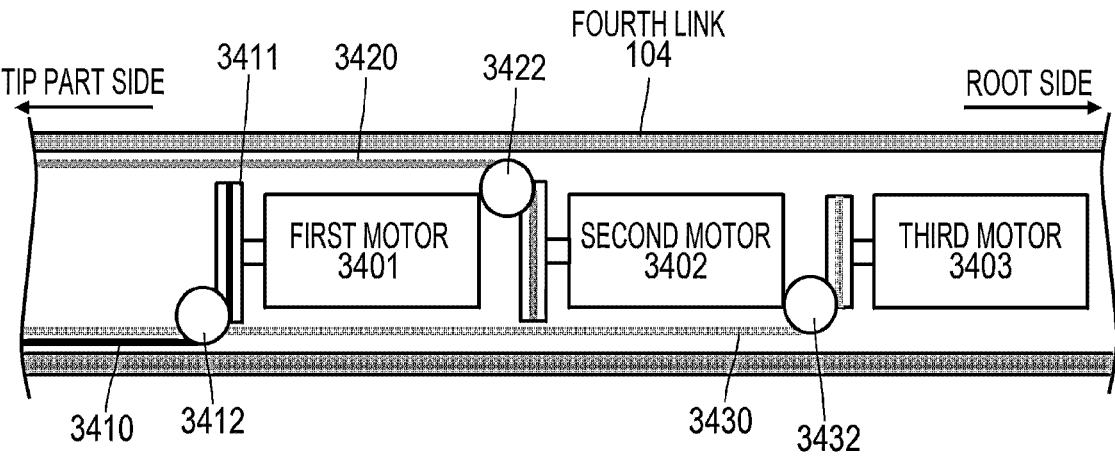
FIG. 34 is a diagram illustrating a configuration example of a wire transmission mechanism corresponding to the arrangement example (1) of the motor.
Figure 35:
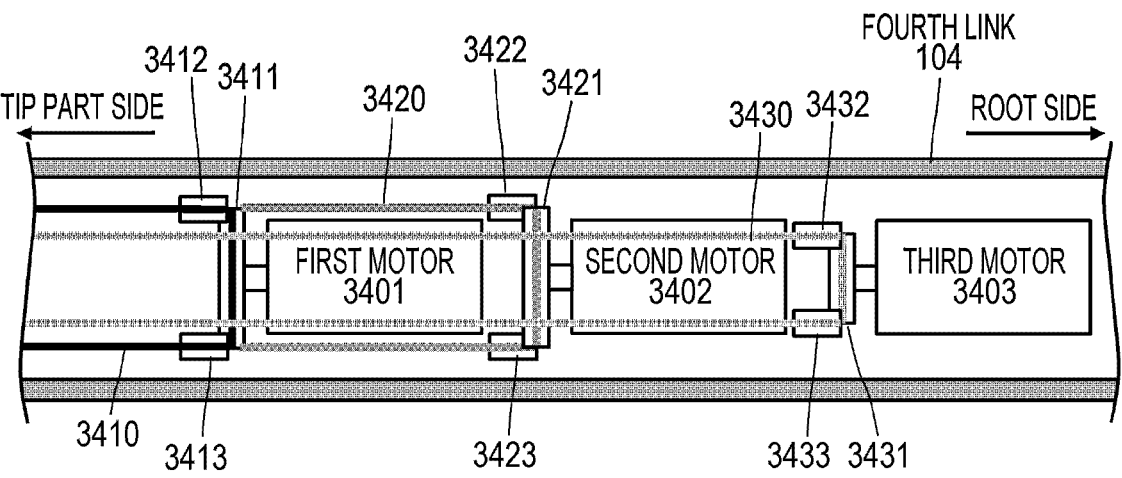
FIG. 35 is a diagram illustrating a configuration example of the wire transmission mechanism corresponding to the arrangement example (1) of the motor.

FIGS. 34 and 35 illustrate a configuration example of a wire transmission mechanism in a case where all three motors 3401 to 3403 described in section O-1 described above are disposed with the output axis direction aligned with the longitudinal direction of the fourth link 104. However, in FIGS. 34 and 35, a rotational position of the fourth link 104 around the longitudinal axis is changed by 90 degrees.

A position of a wire 3410 wound around an output axis pulley 3411 of the first motor 3401 in the fourth link 104 is adjusted via a rerouting pulley 3412 on a forward path side and a rerouting pulley 3413 on a backward path side, and is directed toward the tip part side. Furthermore, a position of a wire 3420 wound around an output axis pulley 3421 of the second motor 3402 in the fourth link 104 is adjusted via a rerouting pulley 3422 on a forward path side and a rerouting pulley 3423 on a backward path side. Here, the wire 3420 is disposed so as not to interfere with the wire 3410 by changing the rotational position of the rerouting pulleys 3422 and 3423 around the longitudinal axis only by 180 degrees with respect to the rerouting pulleys 3412 and 3413. Furthermore, a position of a wire 3430 wound around an output axis pulley 3431 of the third motor 3403 in the fourth link 104 is adjusted via a rerouting pulley 3432 on a forward path side and a rerouting pulley 3433 on a backward path side. Here, the rerouting pulleys 3432 and 3433 are disposed at the same rotational position around the longitudinal axis as the rerouting pulleys 3412 and 3413, and at different positions in a radial direction (or width direction) the wire 3430 is disposed so as not to interfere with the wire 3410.

Note that, although the configuration of the tip part side of each of the wires 3410, 3420, and 3430 is not illustrated, it is assumed that a rerouting pulley or the like is appropriately used to match the arrangements of the wires illustrated in FIGS. 7 to 12, for example.

FIGS. 36 and 37 illustrate a configuration example of a wire transmission mechanism in a case where, out of three motors 3601 to 3603 described in section O-2 described above, the first motor 3601 and the second motor 3602 are disposed with the output axis direction aligned with the longitudinal direction of the fourth link 04, and the third motor 3603 on the root side is disposed with the output axis direction oriented in a direction orthogonal to the longitudinal direction of the fourth link 104. However, in FIGS. 36 and 37, a rotational position of the fourth link 104 around the longitudinal axis is changed by 90 degrees.

A position of a wire 3610 wound around an output axis pulley 3611 of the first motor 3601 in the fourth link 104 is adjusted via a rerouting pulley 3612 on a forward path side and a rerouting pulley 3613 on a backward path side, and is directed toward the tip part side. Furthermore, a position of a wire 3620 wound around an output axis pulley 3621 of the second motor 3602 in the fourth link 104 is adjusted via a rerouting pulley 3622 on a forward path side and a rerouting pulley 3623 on a backward path side. Similarly to the example illustrated in FIGS. 34 and 35, the wire 3620 is disposed so as not to interfere with the wire 3610 by changing the rotational position of the rerouting pulleys 3622 and 3623 around the longitudinal axis only by 180 degrees with respect to the rerouting pulleys 3612 and 3613. Furthermore, a wire 3630 wound around an output axis pulley 3631 of the third motor 3603 can be wired in the fourth link 104 so as to avoid interference with the first motor 3601 disposed on the tip side, the second motor 3602, each of the wires 3610 and 3620, and the like. Of course, a pulley (not illustrated) for changing the path or adjusting the position may be further disposed on at least one of a forward path side or a backward path side of the wire 3630.

Note that, although a configuration of the tip part side of each of the wires 3610, 3620, and 3630 is not illustrated, it is assumed that a rerouting pulley or the like is appropriately used to match the arrangements of the wires illustrated in FIGS. 7 to 12, for example.

FIGS. 38 and 39 illustrate a configuration example of a wire transmission mechanism in a case where, out of three motors 3801 to 3803 described in section O-3 described above, the first motor 3801 is disposed with the output axis direction aligned with the longitudinal direction of the fourth link 104, and the second motor 3802 and the third motor 3803 are disposed with the output axis direction oriented in a direction orthogonal to the longitudinal direction of the fourth link 104. However, in FIGS. 38 and 39, a rotational position of the fourth link 104 around the longitudinal axis is changed by 90 degrees.

A position of a wire 3810 wound around an output axis pulley 3811 of the first motor 3801 in the fourth link 104 is adjusted via a rerouting pulley 3812 on a forward path side and a rerouting pulley 3813 on a backward path side, and is directed toward the tip part side. Furthermore, an output axis of the second motor 3802 is orthogonal to the longitudinal direction of the fourth link 104, and an output axis pulley 3821 of the second motor 3802 is disposed in a direction opposite to the wire 3810. Therefore, a wire 3820 wound around the output axis pulley 3821 can be wired in the fourth link 104 so as to avoid interference with the first motor 3801, the wire 3810, and the like disposed on the tip side. Of course, a pulley (not illustrated) for changing the path or adjusting the position may be further disposed on at least one of a forward path side or a backward path side of the wire 3820. Furthermore, similarly to the second motor 3802, an output axis of the third motor 3803 is orthogonal to the longitudinal direction of the fourth link 104, and an output axis pulley 3831 of the third motor 3803 is disposed in the same direction as the output axis pulley 3821 of the second motor 3802. As can be seen from FIG. 38, a position of the output axis pulley 3831 is shifted in a direction orthogonal to the longitudinal direction of the fourth link 104 so as not to overlap with the output axis pulley 3821. Therefore, the wire 3830 wound around the output axis pulley 3831 can be wired in the fourth link 104 so as to avoid interference with the first motor 3801 disposed on the tip side, the second motor 3802, each of the wires 3810 and 3820, and the like. Of course, a pulley (not illustrated) for changing the path or adjusting the position may be further disposed on at least one of a forward path side or a backward path side of the wire 3830.

Note that, although a configuration of the tip part side of each of the wires 3810, 3820, and 3830 is not illustrated, it is assumed that a rerouting pulley or the like is appropriately used to match the arrangements of the wires illustrated in FIGS. 7 to 12, for example.

INDUSTRIAL APPLICABILITY

The present disclosure has been described in detail above with reference to specific embodiments. However, it is obvious that those skilled in the art can make modifications and substitutions of the embodiments without departing from the gist of the present disclosure.

In the present specification, the embodiments in which the present disclosure is applied to a medical arm device that supports an endoscope have been mainly described, but the gist of the present disclosure is not limited thereto. The present disclosure can be similarly applied to a medical arm device that supports a medical instrument other than the endoscope, for example, forceps, a pneumoperitoneum tube, an energy treatment tool, tweezers, a retractor, or the like at the tip, and the attitude of the medical instrument to be supported can be determined without backlash in three orthogonal degrees of freedom.

In short, the present disclosure has been described in the form of exemplification, and the contents described in the present specification should not be interpreted in a limited manner. In order to determine the gist of the present disclosure, the claims should be taken into consideration.

Note that the present disclosure can have the following configurations.

(1) A medical arm device including:
a first arm part including a tip part that holds a medical instrument and a link that supports the tip part; and
a second arm part that supports the first arm part, in which
the tip part includes
a structure in which three rotation axes are disposed in order of a rotation axis around a longitudinal axis of the medical instrument, a yaw axis that rotates the medical instrument left and right with respect to a tip of the link, and a pitch axis that rotates the medical instrument up and down with respect to the tip of the link in order from a most tip part, and
a first wire for rotation transmission of the yaw axis, a second wire for rotation transmission of the roll axis, a first rerouting pulley that reroutes the first wire between the pitch axis and the yaw axis, a second rerouting pulley that reroutes the second wire between the pitch axis and the yaw axis, and a third rerouting pulley that reroutes the second wire between the yaw axis and the roll axis are disposed on the link.

(2) The medical arm device recited in (1) described above, in which
the tip part includes a structure in which each of joint members corresponding to the three rotation axes is directly connected.

(3) The medical arm device recited in (2) described above, in which
the tip part includes a structure in which a distance between a joint corresponding to the roll axis and a joint corresponding to the pitch axis has a distance that does not cause interference when the tip part rotates around the pitch axis.

(4) The medical arm device recited in any one of (1) to (3) described above, in which
at least one of the first rerouting pulley or the second rerouting pulley includes a set of rerouting pulleys having different diameters disposed on an identical axis on an opposite side of a structure body rotating around the pitch axis.

(5) The medical arm device recited in (4) described above, in which
a shaft constituting an identical axis of the first rerouting pulley or the second rerouting pulley includes an interference avoidance part with a yaw axis pulley around which the first wire is wound to rotate around the yaw axis.

(6) The medical arm device recited in (5) described above, in which
the interference avoidance part includes a small diameter part or a D-cut structure part in a central part of the shaft.

(7) The medical arm device recited in any one of (1) to (6) described above, further including
an interference avoidance structure that avoids interference between the second rerouting pulley and the third rerouting pulley during rotation around the yaw axis.

(8) The medical arm device recited in (7) described above, in which
the interference avoidance structure includes a set of rerouting pulleys constituting the second rerouting pulley and disposed such that rotation axes of the set of rerouting pulleys cross each other.

(9) The medical arm device recited in (7) or (8) described above, in which
the interference avoidance structure includes a structure in which a plurality of pulleys constituting the third rerouting pulley is disposed in a predetermined region in a concentrated manner.

(10) The medical arm device recited in any one of (1) to (9) described above, further including
at least one of a third wire for rotation transmission of the pitch axis, a link mechanism, a gear mechanism, or a motor that directly rotates the pitch axis.

(11) The medical arm device recited in any one of (1) to (10) described above, further including
a pitch axis actuator that supplies a driving force around the pitch axis, a yaw axis actuator that supplies a driving force around the yaw axis, and a roll axis actuator that supplies a driving force around the roll axis.

(12) The medical arm device recited in (11) described above, in which
the pitch axis actuator, the yaw axis actuator, and the roll axis actuator are disposed in order from the tip part.

(13) The medical arm device recited in (11) or (12) described above, further including
a one-rotation absolute encoder used for each of the pitch axis actuator, the yaw axis actuator, and the roll axis actuator.

(14) The medical arm device recited in (13) described above, in which
the roll axis has a rotation movable range larger than one rotation, and
an attitude of the tip part is uniquely derived from a measurement value of the absolute encoder using a correction formula based on forward kinematics.

(15) The medical arm device recited in (14) described above, in which
a diameter of an output axis pulley of the roll axis actuator is larger than or equal to a diameter of a roll axis pulley around which the second wire for rotation transmission of the roll axis is wound to rotate around the roll axis.

(16) The medical arm device recited in any one of (1) to (15) described above, further including:
a first two-groove pulley that changes a path of the first wire along the pitch axis; and

a second two-groove pulley that changes a path of the second wire along the pitch axis.

(17) The medical arm device recited in (16) described above, in which the first two-groove pulley and the second two-groove pulley are supported by an identical shaft.

(18) The medical arm device recited in (16) described above, in which the first two-groove pulley and the second two-groove pulley are supported by shafts different from each other.

(19) The medical arm device recited in (18) described above, in which the first two-groove pulley and the second two-groove pulley are not coaxial.

(20) The medical arm device recited in any one of (1) to (19) described above, in which the medical instrument is a medical observation device, and the tip part includes a structure in which an optical axis rotation axis (roll axis) of the medical observation device, a pan axis (yaw axis) for changing an observation direction of the medical observation device, and a tilt axis (pitch axis) are arranged in this order from a most tip part.

(21) The medical arm device recited in (1) described above, in which an output axis direction of at least one actuator among a plurality of actuators that drives the tip part having a plurality of degrees of freedom is disposed on a root side of the link so as to be aligned with a longitudinal direction of the link.

(21-1) The medical arm device recited in (21) described above, in which all output axis directions of the plurality of actuators are disposed on a root side of the link so as to be aligned with the longitudinal direction of the link.

(21-2) The medical arm device recited in (21) described above, in which output axis directions of some of the plurality of actuators are disposed on a root side of the link so as to be different from the longitudinal direction of the link, and output axis directions of other actuators are disposed so as to be aligned with the longitudinal direction of the link.

(22) The medical arm device recited in (21) described above, in which the link includes a reduced diameter part including a section in which an output axis direction of the at least one actuator is aligned with a longitudinal direction of the link.

(23) The medical arm device recited in (21) or (22) described above, in which a link rotating actuator that rotates the link with respect to another link is disposed such that a rotation axis of a rotation mechanism unit that rotatably couples a root side of the link with another link does not coincide with an output axis of the link rotating actuator.

(24) The medical arm device recited in (23) described above, in which any one of the plurality of actuators is disposed in the rotation mechanism unit.

(24-1) The medical arm device recited in (24) described above, in which

36 the rotation mechanism unit is a joint part that couples the link to the another link so as to rotate the link around the pitch axis.

(25) The medical arm device recited in (23) or (24) described above, further including a steel belt mechanism that transmits a rotational force of the link rotating actuator to the rotation mechanism unit.

REFERENCE SIGNS LIST

100 Medical arm device
101 First link
102 Second link
103 Third link
104 Fourth link
111 First joint part
112 Second joint part
113 Third joint part
114 Vertical rotation axis part (Tilt axis, Pitch axis)
115 Left-right rotation axis part (Pan axis, Yaw axis)
116 Optical axis rotation axis part (Roll axis)
200 Endoscope
201 Lens barrel
202 Camera head
501 Pitch axis wire
502 Yaw axis wire
503 Roll axis wire
601 Pitch axis motor
602 Yaw axis motor
603 Roll axis motor
701 Pitch axis component
702 Pitch axis driving pulley
703 Shaft
704 Shaft
801 Yaw axis pulley
901 Two-groove pulley
902 Two-groove pulley
903 Rerouting pulley
904 Rerouting pulley
1001 First connection part
1002 Second connection part
1101 Roll axis pulley
1102 Two-groove pulley
1103 Two-groove pulley
1104 Rerouting pulley
1105 Rerouting pulley
1106 Two-groove pulley
1107 Rerouting pulley
1108 Rerouting pulley
1801 Rerouting pulley
2001 Shaft
2200 Motor
2201 Motor body
2202 Brake
2203 Speed reducer
2204 Encoder
2205 Torque sensor
2206 Circuit unit
2301 First motor
2302 Second motor
2303 Third motor
2401 First motor
2402 Second motor
2403 Third motor
2601 First motor
2602 Second motor

2603 Third motor
2801 First motor
2802 Second motor
2803 Third motor
3001 First motor
3002 Second motor
3003 Third motor
3004 Motor
3005 Steel belt
3006 Pulley (Output axis pulley of motor 3004)

The invention claimed is:

1. A medical arm device comprising:
a first arm part including a tip part that holds a medical instrument and a link that supports the tip part; and
a second arm part that supports the first arm part, wherein the tip part includes:
   a structure in which three rotation axes are disposed in order of a roll axis around a longitudinal axis of the medical instrument, a yaw axis that rotates the medical instrument left and right with respect to a tip of the link, and a pitch axis that rotates the medical instrument up and down with respect to the tip of the link; and
   a first wire for rotation transmission of the yaw axis, a second wire for rotation transmission of the roll axis, a first rerouting pulley that reroutes the first wire between the pitch axis and the yaw axis, a second rerouting pulley that reroutes the second wire between the pitch axis and the yaw axis, and a third rerouting pulley that reroutes the second wire between the yaw axis and the roll axis,
wherein the first wire, the second wire, the first rerouting pulley, the second rerouting pulley, and the third rerouting pulley are disposed on the link, and
wherein the medical arm device further includes a plurality of motors disposed on a root side of the link of the first arm part, each of the plurality of motors is fixed such that its rotation axis is parallel to the pitch axis.

2. The medical arm device according to claim 1, wherein the tip part includes a structure in which respective joint members corresponding to the three rotation axes is directly connected.

3. The medical arm device according to claim 2, wherein the tip part includes a structure in which a distance between the joint member corresponding to the roll axis and the joint member corresponding to the pitch axis does not cause interference when the tip part rotates around the pitch axis.

4. The medical arm device according to claim 1, wherein at least one of the first rerouting pulley or the second rerouting pulley includes a set of rerouting pulleys having different diameters disposed on an identical axis on an opposite side of a structure body rotating around the pitch axis.

5. The medical arm device according to claim 4, wherein a shaft constituting an identical axis of the first rerouting pulley or the second rerouting pulley includes an interference avoidance part with a yaw axis pulley around which the first wire is wound to rotate around the yaw axis.

6. The medical arm device according to claim 5, wherein the interference avoidance part includes a D-cut structure part in a central part of the shaft.

7. The medical arm device according to claim 1, further comprising an interference avoidance structure that avoids interference between the second rerouting pulley and the third rerouting pulley during rotation around the yaw axis.

8. The medical arm device according to claim 7, wherein the interference avoidance structure includes a set of rerouting pulleys constituting the second rerouting pulley and disposed such that rotation axes of the set of rerouting pulleys cross each other.

9. The medical arm device according to claim 7, wherein the interference avoidance structure includes a structure in which a plurality of pulleys constituting the third rerouting pulley is disposed in a predetermined region.

10. The medical arm device according to claim 1, further comprising:
at least one of a third wire for rotation transmission of the pitch axis, a link mechanism, a gear mechanism, or a motor that directly rotates the pitch axis.

11. The medical arm device according to claim 1, wherein the plurality of motors include:
   a pitch axis actuator that supplies a driving force around the pitch axis;
   a yaw axis actuator that supplies a driving force around the yaw axis; and
   a roll axis actuator that supplies a driving force around the roll axis.

12. The medical arm device according to claim 11, further comprising
   a one-rotation absolute encoder used for each of the pitch axis actuator, the yaw axis actuator, and the roll axis actuator to detect a rotation angle of each of the actuators.

13. The medical arm device according to claim 12, wherein
   the roll axis has a rotation movable range larger than one rotation, and
   an attitude of the tip part is derived from a measurement value of the absolute encoder using a correction formula based on forward kinematics.

14. The medical arm device according to claim 13, wherein
   a diameter of an output axis pulley of the roll axis actuator is larger than or equal to a diameter of a roll axis pulley around which the second wire is wound to rotate around the roll axis.

15. The medical arm device according to claim 1, further comprising:
   a first two-groove pulley that changes a path of the first wire along the pitch axis; and
   a second two-groove pulley that changes a path of the second wire along the pitch axis.

16. The medical arm device according to claim 1, wherein
   an output axis direction of at least one of the plurality of motors drives the tip part having a plurality of degrees of freedom and is disposed on the root side of the link so as to be aligned with a longitudinal direction of the link.

17. The medical arm device according to claim 16, wherein
   the link includes a section in which the output axis direction of the at least one of the plurality of motors is aligned with the longitudinal direction of the link.

18. The medical arm device according to claim 16, wherein
   a link rotating actuator that rotates the link with respect to another link is disposed such that a rotation axis of a joint part that rotatably couples the root side a of the link with the another link does not coincide with an output axis of the link rotating actuator.

19. The medical arm device according to claim 18, wherein any one of the plurality of motors is disposed in the joint part.

20. The medical arm device according to claim 18, further comprising a steel belt mechanism that transmits a rotational force of the link rotating actuator to the joint part.

\* \* \* \* \*